US012295839B2

(12) United States Patent
Becerra et al.

(10) Patent No.: US 12,295,839 B2
(45) Date of Patent: May 13, 2025

(54) MOTORIZED IMPLANT DELIVERY SYSTEM

(71) Applicant: Edwards Lifesciences Corporation, Irvine, CA (US)

(72) Inventors: Matthew Michael Becerra, Lake Forest, CA (US); David Robert Landon, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 674 days.

(21) Appl. No.: 17/156,370

(22) Filed: Jan. 22, 2021

(65) Prior Publication Data
US 2021/0145576 A1    May 20, 2021

Related U.S. Application Data

(63) Continuation of application No. PCT/US2020/029138, filed on Apr. 21, 2020.
(Continued)

(51) Int. Cl.
A61F 2/24 (2006.01)
A61B 90/00 (2016.01)
(Continued)

(52) U.S. Cl.
CPC ............ *A61F 2/2427* (2013.01); *A61B 90/06* (2016.02); *A61B 90/37* (2016.02); *A61F 2/9517* (2020.05);
(Continued)

(58) Field of Classification Search
CPC ...... A61F 2/2427; A61F 2/9517; A61B 90/06; A61B 90/37; A61B 2090/065
See application file for complete search history.

(56) References Cited

U.S. PATENT DOCUMENTS 3,409,013 A   11/1968   Berry
3,472,230 A   10/1969   Fogarty
(Continued)

FOREIGN PATENT DOCUMENTS

CA   2304325 A1   10/2000
DE   2246526 A1   3/1973
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Sarah A Long
*Assistant Examiner* — Raihan R Khandker
(74) *Attorney, Agent, or Firm* — Thomas C. Richardson

(57) ABSTRACT

Systems, apparatuses, and methods disclosed herein are provided for a motorized implant delivery system. The delivery system may utilize a processor for control of at least one motor for actuating a delivery apparatus. The delivery system may include sensors configured sense one or more of a condition of the patient's body or a condition of the delivery apparatus. The processor may process the signals provided by the sensors, which may comprise feedback signals to the processor.

22 Claims, 44 Drawing Sheets

Related U.S. Application Data

(60) Provisional application No. 62/837,641, filed on Apr. 23, 2019.

(51) Int. Cl.
    *A61F 2/95*     (2013.01)
    *G16H 10/60*     (2018.01)
    *G16H 40/63*     (2018.01)

(52) U.S. Cl.
    CPC ............ *G16H 10/60* (2018.01); *G16H 40/63* (2018.01); *A61B 2090/065* (2016.02)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |

(56) References Cited

U.S. PATENT DOCUMENTS

| | | |
|---|---|---|
| 6,527,800 B1 | 3/2003 | McGuckin, Jr. et al. |
| 6,527,979 B2 | 3/2003 | Constantz |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,629,534 B1 | 10/2003 | St. Goar et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,806,919 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang et al. |
| 8,167,934 B2 | 5/2012 | Styrc et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |

(56) References Cited

U.S. PATENT DOCUMENTS

| | | |
|---|---|---|
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0149159 A1 | 7/2005 | Andreas et al. |
| 2005/0159811 A1 | 7/2005 | Lane |
| 2005/0182486 A1 | 8/2005 | Gabbay |
| 2005/0197557 A1* | 9/2005 | Strommer ............ A61B 34/20 600/407 |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |

(56) References Cited

U.S. PATENT DOCUMENTS

| | | |
|---|---|---|
| 2007/0213813 A1 | 9/2007 | Von Segesser et al. |
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054969 A1 * | 2/2009 | Salahieh ................ A61F 2/013 |
| | | 623/2.11 |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0158011 A1 * | 6/2012 | Sandhu ................ A61B 34/30 |
| | | 606/130 |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0325035 A1 | 12/2013 | Hauck et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052241 A1 * | 2/2014 | Harks ................ A61B 34/20 |
| | | 623/2.11 |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Bortlein et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277412 A1 | 9/2014 | Bortlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |

(56) References Cited

U.S. PATENT DOCUMENTS

| | | |
|---|---|---|
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | McNamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0079785 A1 | 3/2017 | Li |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0085559 A1* | 3/2018 | Laby ............... A61F 2/2427 |
| 2018/0104077 A1* | 4/2018 | Cartledge ............... A61F 2/93 |
| 2018/0110534 A1 | 4/2018 | Gavala et al. |
| 2018/0110622 A1* | 4/2018 | Gregg ............... A61F 2/9522 |
| 2018/0116790 A1 | 5/2018 | Ratz et al. |
| 2018/0263714 A1* | 9/2018 | Kostrzewski ...... A61B 17/1703 |
| 2018/0311473 A1 | 11/2018 | Laby et al. |
| 2019/0008639 A1 | 1/2019 | Landon et al. |
| 2019/0008640 A1 | 1/2019 | Cooper et al. |
| 2019/0060057 A1 | 2/2019 | Cohen et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0214767 A1* | 7/2020 | Lonkadi ............... G16H 30/20 |
| 2020/0229920 A1* | 7/2020 | Wallace ............... A61B 6/4014 |
| 2020/0345494 A1 | 11/2020 | Srinimukesh et al. |
| 2020/0352718 A1 | 11/2020 | Rowe et al. |
| 2020/0383782 A1* | 12/2020 | Basude ............... A61F 2/246 |
| 2021/0145576 A1 | 5/2021 | Becerra et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1171059 A1 | 1/2002 |
| EP | 1239901 A1 | 9/2002 |
| EP | 1255510 A1 | 11/2002 |
| EP | 1259194 A1 | 11/2002 |
| EP | 1369098 A1 | 12/2003 |
| EP | 1469797 A1 | 10/2004 |
| EP | 1472996 A1 | 11/2004 |
| EP | 1570809 A1 | 9/2005 |
| EP | 1653888 A2 | 5/2006 |
| EP | 1849440 A1 | 10/2007 |
| EP | 1935377 A1 | 6/2008 |
| EP | 2124826 A1 | 12/2009 |
| EP | 2168536 A1 | 3/2010 |
| EP | 2413842 A1 | 2/2012 |
| EP | 2446915 A1 | 5/2012 |
| EP | 2745805 A1 | 6/2014 |
| EP | 2749254 A1 | 7/2014 |
| EP | 2750630 A1 | 7/2014 |
| EP | 2777616 A1 | 9/2014 |
| EP | 2777617 A1 | 9/2014 |
| EP | 2918249 A2 | 9/2015 |
| EP | 2948103 A2 | 12/2015 |
| EP | 2967858 A2 | 1/2016 |
| EP | 3037064 A1 | 6/2016 |
| EP | 3046511 A2 | 7/2016 |
| EP | 3057541 A1 | 8/2016 |
| EP | 3075354 A2 | 10/2016 |
| EP | 3139864 A1 | 3/2017 |
| EP | 3142603 A1 | 3/2017 |
| EP | 3184083 A1 | 6/2017 |
| EP | 3294220 A1 | 3/2018 |

(56) References Cited

FOREIGN PATENT DOCUMENTS

| | | |
|---|---|---|
| EP | 3417813 A1 | 12/2018 |
| EP | 3424469 A1 | 1/2019 |
| EP | 3570779 A1 | 11/2019 |
| FR | 2788217 A1 | 7/2000 |
| GB | 1264471 A | 2/1972 |
| GB | 1315844 A | 5/1973 |
| GB | 2056023 A | 3/1981 |
| GB | 2398245 A | 8/2004 |
| JP | 2012232134 A | 11/2012 |
| SU | 1271508 A1 | 11/1986 |
| WO | 9116041 A1 | 10/1991 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9933414 A1 | 7/1999 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0061034 A1 | 10/2000 |
| WO | 0236048 A1 | 5/2002 |
| WO | 03047468 A1 | 6/2003 |
| WO | 03092554 A1 | 11/2003 |
| WO | 2004030569 A2 | 4/2004 |
| WO | 2005011534 A1 | 2/2005 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006085225 A1 | 8/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008035337 A2 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011081997 A1 | 7/2011 |
| WO | 2012008459 A1 | 1/2012 |
| WO | 2012032187 A1 | 3/2012 |
| WO | 2012095455 A2 | 7/2012 |
| WO | 2013005878 A1 | 1/2013 |
| WO | 2013028387 A2 | 2/2013 |
| WO | 2013106585 A1 | 7/2013 |
| WO | 2014009213 A1 | 1/2014 |
| WO | 2014018432 A2 | 1/2014 |
| WO | 2014079291 A1 | 5/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015004624 A1 | 1/2015 |
| WO | 2015004625 A1 | 1/2015 |
| WO | 2015057407 A1 | 4/2015 |
| WO | 2015077274 A1 | 5/2015 |
| WO | 2016002189 A1 | 1/2016 |
| WO | 2016004137 A1 | 1/2016 |
| WO | 2016016899 A1 | 2/2016 |
| WO | 2016100799 A1 | 6/2016 |
| WO | 2017006510 A1 | 1/2017 |
| WO | 2017035487 A1 | 3/2017 |
| WO | 2018000333 A1 | 1/2018 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Pavcnik, M.D., Ph.D., Dusan, et al. "Development and Initial Experimental Evaluation of a Prosthetic Aortic Valve for Transcatheter Placement," Cardiovascular Radiology 1992; 183: 151-154.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Wheatley, M.D., David J., "Valve Prostheses," Rob & Smith's Operative Surgery, Fourth Edition, pp. 415-424, Butterworths 1986.

Bavaria, Joseph E. M.D. et al.: "Transcatheter Mitral Valve Implantation: The Future Gold Standard for MR?," Applicant requests the Examiner to consider this reference to be prior art as of December of 2010.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

(56) References Cited

OTHER PUBLICATIONS

Condado, Jose Antonio, et al., "Percutaneous Treatment of Heart Valves," Rev Esp Cardio. 2006;59(12):1225-31, Applicant believes this may have been available as early as December of 2006.
Feldman, Ted, MD. "Prospects for Percutaneous Valve Therapies," Circulation 2007; 116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Fornell, Dave, ""Transcatheter Mitral Valve replacement Devices in Development,"" Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, ""CardiAQ Valve Technologies: Percutaneous Mitral Valve Replacement,"" Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "'Double-Crowned Valved Stents For Off-Pump Mitral Valve Replacement," European Journal of Cardio-thoracic Surgery 28 (2005) 194-199, Applicant believes this may have been available as early as August of 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on November of 2011 at TCT.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"Company Overview," at TVT on Jun. 25, 2009.
Biospace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
Biospace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.

* cited by examiner

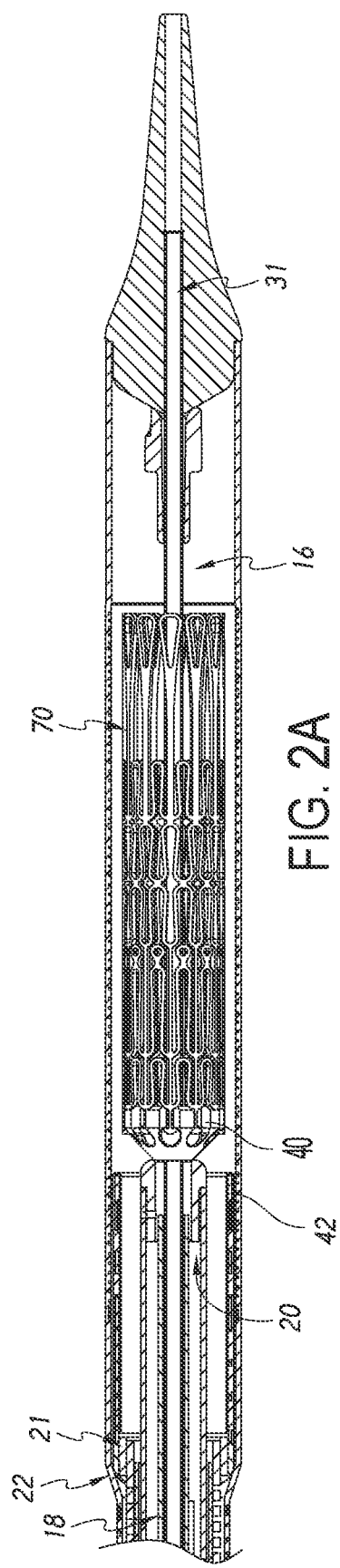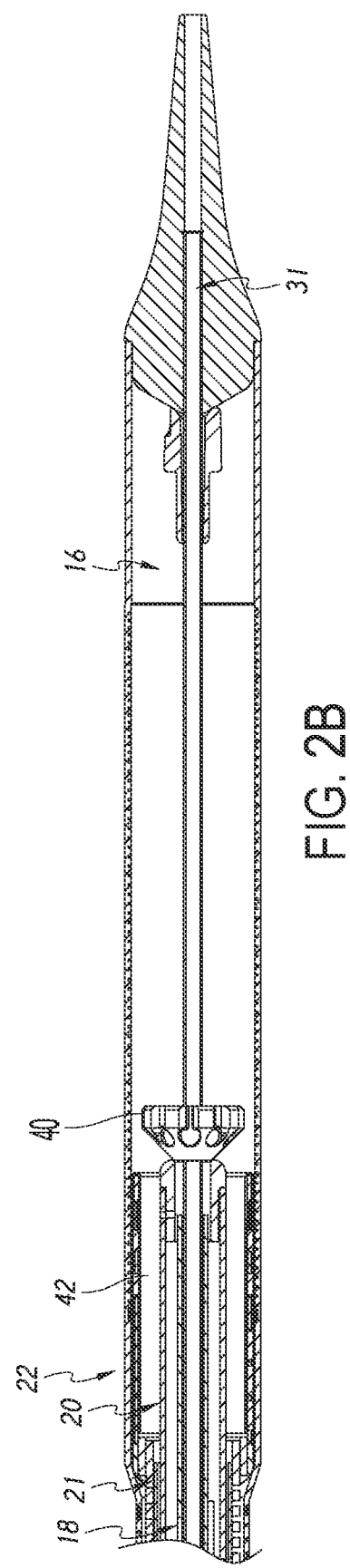

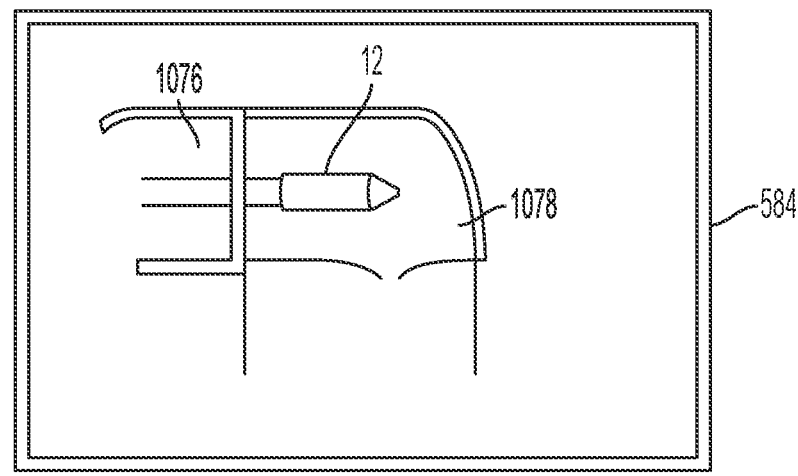
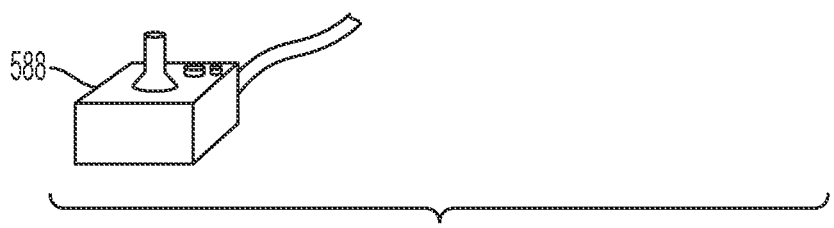
FIG. 37
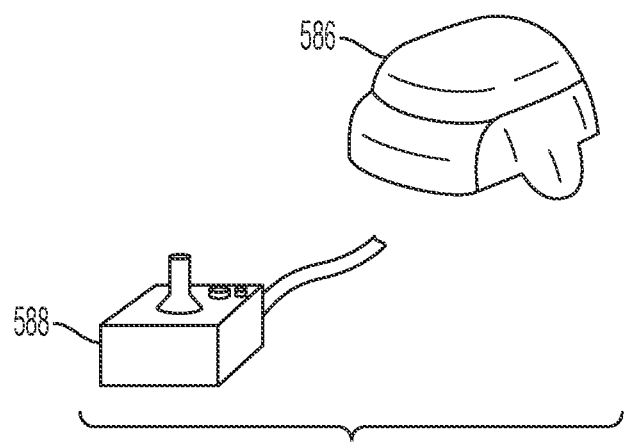
FIG. 38

MOTORIZED IMPLANT DELIVERY SYSTEM

CROSS REFERENCE TO RELATED APPLICATIONS

This application is a continuation of International Application No. PCT/US2020/029138, filed Apr. 21, 2020, which designates the United States and was published in English by the International Bureau on Oct. 29, 2020 as WO 2020/219459, which claims priority to U.S. Provisional App. No. 62/837,641, filed Apr. 23, 2019, the entirety of which is hereby incorporated by reference.

BACKGROUND

Field

Various embodiments disclosed herein relate generally to delivery systems for implants. Some embodiments relate to delivery systems and implants for replacing diseased heart valves.

The four human heart valves are the aortic valve, mitral valve, tricuspid valve and pulmonary valve. These heart valves function essentially as one-way valves operating in synchronization with the pumping heart to ensure that blood flows downstream, while blocking blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life-threatening condition. For example, valve insufficiency can lead to conditions such as heart hypertrophy and dilation of the ventricle. Thus, extensive efforts have been made to develop methods and apparatuses to repair or replace impaired heart valves.

Prosthetic implants exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prosthetic implants including but not limited to replacement heart valves and other types of implants that may be utilized for heart valve repair can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering an implant to a desired location in the human body, for example delivering a replacement heart valve or other form of implant for heart valve repair via a catheter-based procedure, can also be challenging. Obtaining access to perform procedures in the heart or in other anatomical locations may require delivery of devices percutaneously through tortuous vasculature or through open or semi-open surgical procedures. The ability to control the deployment of the implant at the desired location can also be challenging.

SUMMARY

Embodiments of the present disclosure are directed to a motorized implant delivery system. Such a system may be used to deliver and/or controllably deploy an implant, such as but not limited to a replacement heart valve or an implant for repair of a heart valve, to a desired location within the body. In some embodiments, a replacement heart valve and methods for delivering a replacement heart valve to a native heart valve or repairing a heart valve, such as a mitral valve, are provided.

The delivery system may utilize a processor for control of at least one motor for actuating a delivery apparatus. The delivery system may include sensors configured to sense one or more of a condition of the patient's body or a condition of the delivery apparatus. The processor may process the signals provided by the sensors, which may take the form of feedback signals to the processor. The sensors may be located on a catheter. The sensors may also take the form of imaging devices that provide information regarding the patient's anatomy and/or the location of the catheter and implant in the patient's body.

Embodiments of the present disclosure include a delivery system for delivering an implant to a location within a patient's body. The system may include a delivery apparatus configured to deliver the implant to the location within the patient's body. The system may include at least one motor configured to actuate at least a portion of the delivery apparatus. The system may include a processor configured to operate the at least one motor to actuate at least the portion of the delivery apparatus.

Embodiments of the present disclosure include a delivery system for delivering an implant to a location within a patient's body. The system may include a delivery apparatus configured to deliver the implant to the location within the patient's body. The system may include one or more sensors coupled to the delivery apparatus and configured to sense one or more of a condition of the patient's body or a condition of the delivery apparatus. The system may include a processor configured to provide an output based on the one or more of a condition of the patient's body or a condition of the delivery apparatus sensed by the one or more sensors.

Embodiments of the present disclosure include a delivery system for delivering an implant to a location within a patient's body. The system may include an elongate shaft configured to pass within the patient's body. The elongate shaft may include an outer sheath having an outer lumen and a proximal end and a distal end, at least a portion of the outer sheath surrounding an implant retention area configured to retain the implant. The elongate shaft may include a rail shaft located within the outer lumen and having a proximal end and a distal end, the rail shaft configured to be steerable. The elongate shaft may include an inner shaft located within the outer lumen and having a proximal end and a distal end. The elongate shaft may include an inner retention member coupled to the inner shaft and configured to be releasably coupled to the implant, wherein the outer sheath and inner shaft are configured to move together relative to the rail shaft while the implant remains in the implant retention area, and wherein the outer sheath is configured to retract relative to the inner shaft in order to at least partially deploy the implant. The system may include at least one motor configured to actuate at least a portion of the elongate shaft.

Embodiments of the present disclosure include methods of using the systems. For example, a method may include extending a delivery apparatus within a portion of a patient's body to deliver an implant to a body location, wherein at least a portion of the delivery apparatus is actuated by at least one motor operated by a processor.

Another method may include extending a delivery apparatus within a portion of a patient's body to deliver an implant to a body location, the delivery apparatus including one or more sensors coupled to the delivery apparatus and configured to sense one or more of a condition of the patient's body or a condition of the delivery apparatus. The method may include providing, with a processor, an output based on the one or more of a condition of the patient's body or a condition of the delivery apparatus sensed by the one or more sensors.

Embodiments of the present disclosure include a delivery system for delivering an implant to a location within a patient's body. The system may include an elongate shaft having a proximal end and a distal end. The elongate shaft may include an implant retention area configured to retain the implant, a capsule configured to surround the implant retention area, and at least one electromagnet configured to attract or repel a portion of the capsule to vary a size of the capsule.

Another method may include deploying an elongate shaft to a location within a patient's body, the elongate shaft including a capsule surrounding an implant retention area retaining an implant for implantation within the patient's body. The method may include utilizing at least one electromagnet to attract or repel a portion of the capsule to vary a size of the capsule within the patient's body.

Embodiments of the present disclosure include a delivery system for delivering an implant to a location within a patient's body. The system may include an elongate shaft having a proximal end and a distal end. The elongate shaft may include an implant retention area configured to retain the implant and an electrically detachable coupler configured to couple to the implant and to detach from at least a portion of the implant.

Another method may include extending a delivery apparatus within a portion of a patient's body to deliver an implant to a body location. The method may include detaching at least a portion of the implant from an electrically detachable coupler within the patient's body.

BRIEF DESCRIPTION OF THE DRAWINGS

FIG. 2A shows a partial cross-sectional view of the distal end of the delivery system of FIG. 1 loaded with the implant of FIG. 3A.

FIG. 2B shows a partial cross-sectional view of the distal end of the delivery system of FIG. 1 without the implant of FIG. 3A.

FIG. 37 illustrates a perspective view of an embodiment of a control device and an output device.

FIG. 38 illustrates a perspective view of an embodiment of a control device and an output device.

DETAILED DESCRIPTION

The present specification and drawings provide aspects and features of the disclosure in the context of several embodiments of delivery systems and methods. The delivery systems and methods are preferably used for improving accuracy and ease of use during implantation of a medical device in a human body. Current medical device implantations are often performed using minimally invasive procedures, which typically involve flexible elongate catheters that are advanced through a patient's vasculature to a treatment site. Because there is no direct line of sight at the treatment site, the clinician must rely on fluoroscopy and other imaging, which can be challenging. Furthermore, the clinician is often required to manipulate buttons and knobs on a delivery system handle during the treatment procedure, which can further distract the clinician. Therefore, enhanced delivery systems that utilize sensors, motors and/or artificial intelligence have the potential to greatly enhance the quality and consistency of the outcome.

Embodiments of the delivery systems and methods described herein are configured for use in the vasculature of a patient, such as for replacement of natural heart valves in a patient or repair of the heart valves. These embodiments may be discussed in connection with replacing or repairing specific valves such as the patient's aortic, tricuspid, mitral, or pulmonary valve. However, it is to be understood that the features and concepts discussed herein can be applied to devices other than heart valve implants. For example, the delivery systems and methods can be applied to medical implants, for example other types of expandable prostheses, for use elsewhere in the body, such as within an artery, a vein, or other body cavities or locations. In addition, specific features of a valve, delivery system, method, etc. should not be taken as limiting, and features of any one embodiment discussed herein can be combined with features of other embodiments as desired and when appropriate. While certain of the embodiments described herein are described in connection with a transfemoral/transseptal delivery approach, the embodiments disclosed herein are also well-suited for other delivery approaches such as, for example, transapical, transatrial, or transjugular approaches. Moreover, the features described in connection with certain embodiments can be incorporated with other embodiments, including those that are described in connection with different delivery approaches.

Figure 1:
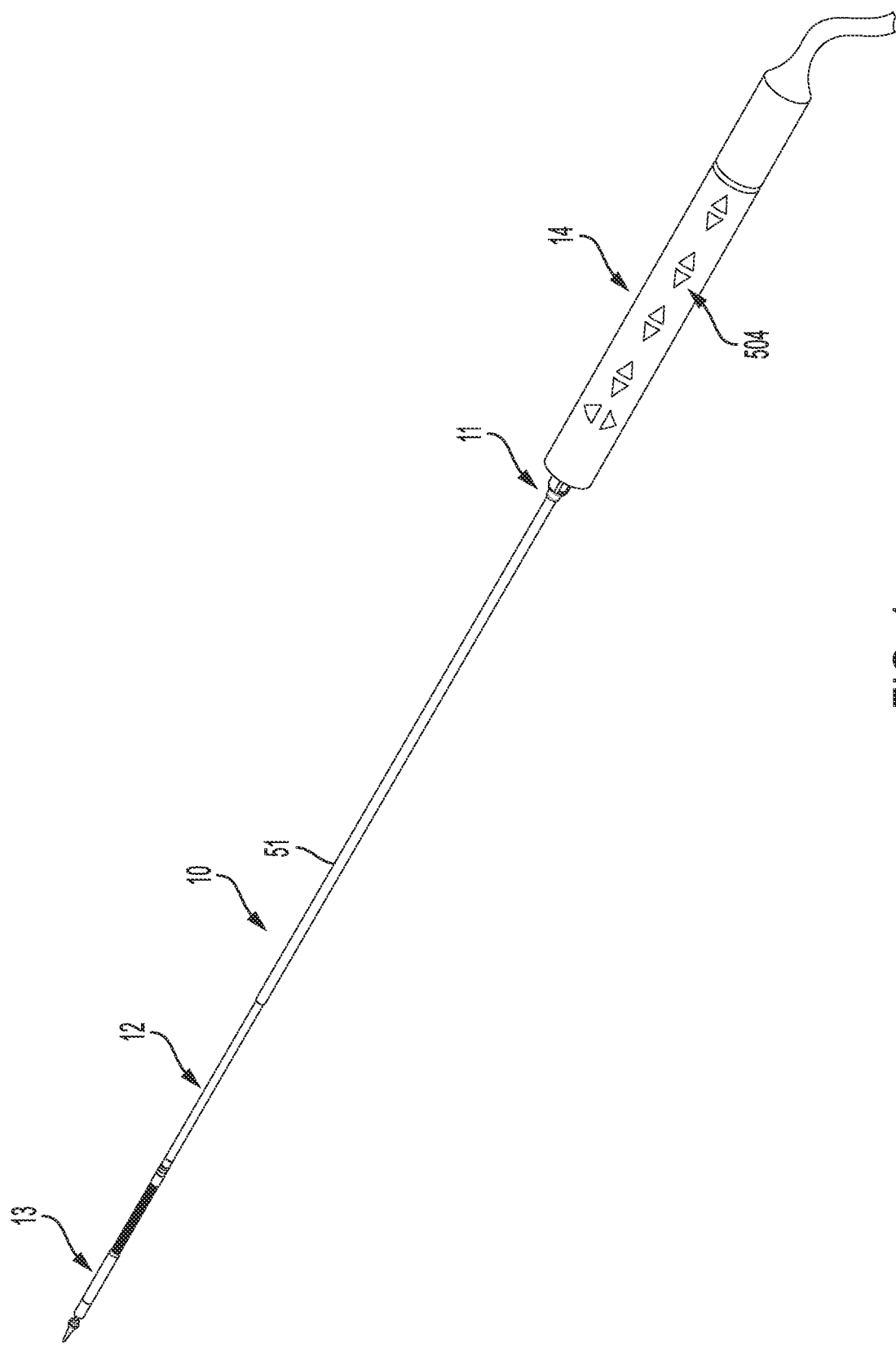
FIG. 1 shows an embodiment of a delivery system.

FIG. 1 illustrates an embodiment of a delivery system 10 according to an embodiment of the present disclosure. The delivery system 10 may be used to deploy an implant, such as a prosthetic replacement heart valve, to a location within a patient's body. In some embodiments, the delivery system 10 may provide multiple planes (e.g., two planes) of deflection for assisting with navigation through a patient's vascular and for enhanced precision during delivery of the implant. Replacement heart valves may be delivered to a patient's mitral (or tricuspid) valve annulus or other heart valve location (such as the aortic or pulmonary valve) in various manners, such as by open surgery, minimally-invasive surgery, and percutaneous or transcatheter delivery through the patient's vasculature. While the delivery system 10 may be described in certain embodiments in connection with a percutaneous delivery approach, and more specifically a transfemoral delivery approach, it should be understood that features of delivery system 10 can be applied to other delivery systems, including delivery systems for a transapical, transatrial, or transjugular delivery approach.

The delivery system 10 may be used to deploy an implant, such as a replacement heart valve that may be described elsewhere in this specification, within the body. The delivery system 10 may receive and/or cover portions of the implant such as a first end 301 and second end 303 of the implant 70, or prosthesis, illustrated in FIG. 3A. For example, the delivery system 10 may be used to deliver an expandable implant 70, where the implant 70 includes the first end 301 and the second end 303, and wherein the second end 303 is configured to be deployed or expanded before the first end 301.

FIG. 2A further shows an example of the implant 70 that can be inserted into a portion of the delivery system 10, specifically into an implant retention area 16. For ease of understanding, in FIG. 2A, the implant is shown with only the bare metal frame illustrated. The implant 70, or prosthesis, can take any number of different forms. One example of a frame for an implant is shown in FIG. 3A; however, other frame configurations may be utilized in other embodiments. The implant 70 may include one or more sets of anchors, such as distal (or ventricular) anchors 80 (marked in FIG. 3A), which are coupled to a distal end portion of the implant and extend in a generally proximal direction when the implant frame is in an expanded configuration. When the implant is used for mitral or tricuspid valve replacement, the distal anchors may be shaped to capture native leaflets between the anchors and the tubular main body of the implant. The implant may also include proximal (or atrial) anchors 82 for placement on an atrial side of an annulus, thereby further enhancing stability. The atrial anchors may extend radially and/or distally when the implant frame is in an expanded configuration. The implant may further include struts 72 on an atrial end, which may include tabs 74 at the first end 301 (marked in FIG. 3A). The tabs may provide an enlarged tip, such as a mushroom shape, sized for placement in a corresponding retention region, such as a slot or recess, along a distal end of a delivery system, thereby ensuring secure coupling of the implant to the delivery system.

Figure 3A:
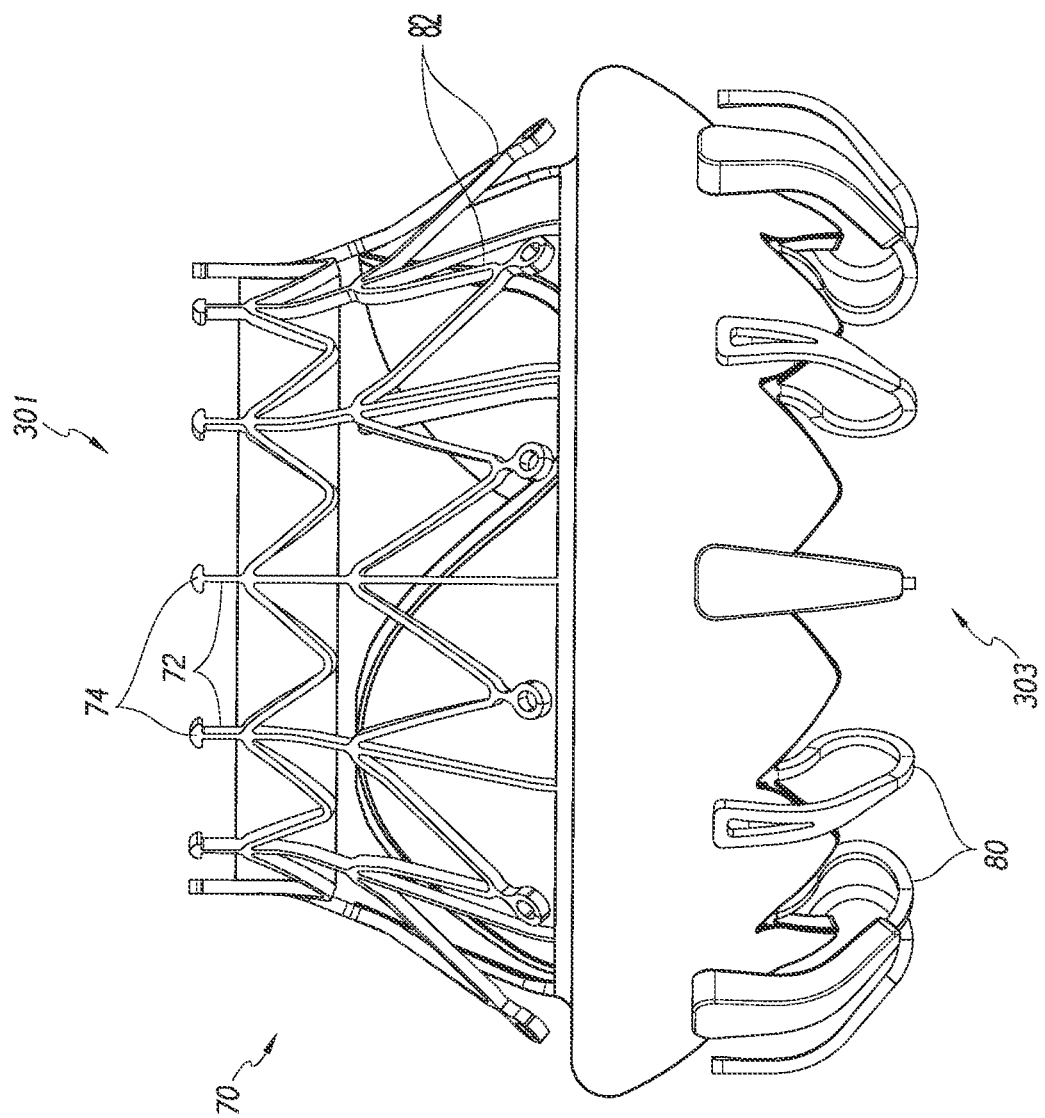
FIG. 3A shows a side view of an embodiment of an implant in the form of a valve prosthesis that may be delivered using the delivery systems described herein.
Figure 3B:
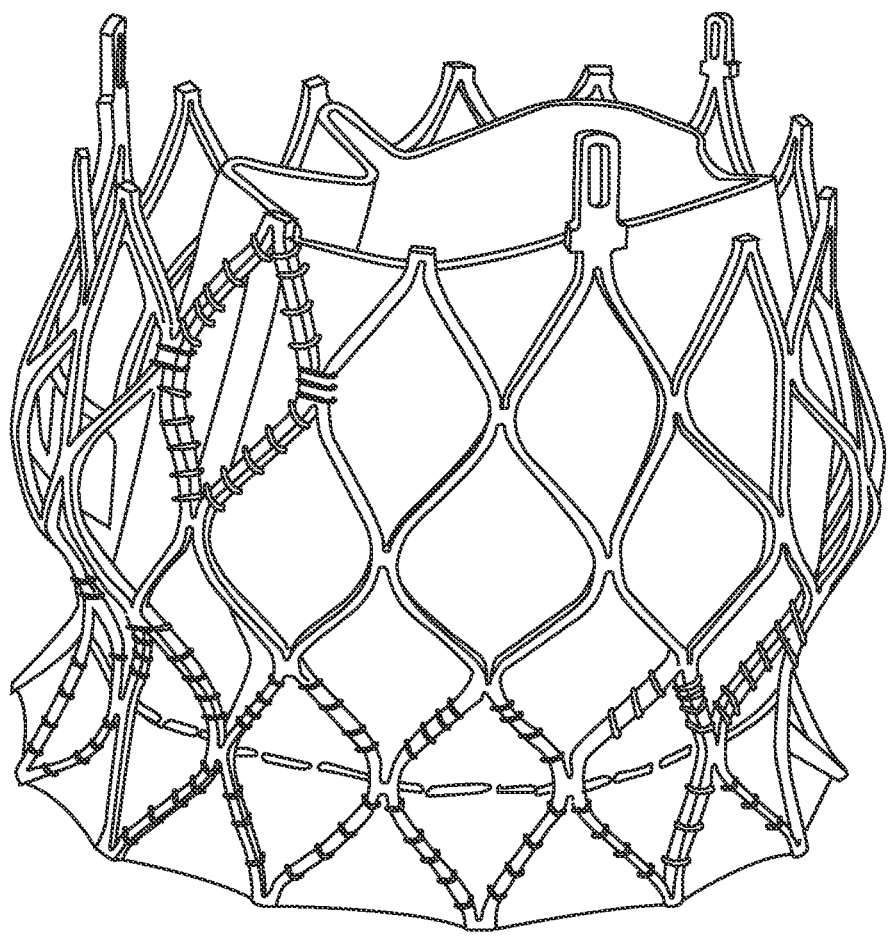
FIG. 3B shows a side perspective view of an embodiment of an aortic valve prosthesis that may be delivered using the delivery systems described herein.

In some embodiments, the delivery system 10 may be used in conjunction with a replacement aortic valve, such as shown in FIG. 3B. In some embodiments the delivery system 10 can be modified to support and deliver the replacement aortic valve. However, the procedures and structures discussed below can similarly be used for a replacing the function of a mitral, tricuspid, pulmonary or aortic valve, as well as other valves, such as a venous valve in the human body. The principles, procedures and structures of the disclosed embodiments are also fully applicable to other implants, which may be used for other medical treatments (unrelated to heart valves).

Referring again to FIG. 1, the delivery system 10 may be configured to deliver the implant to a location within the patient's body. The delivery system 10 may include an elongate shaft 12 that may comprise a shaft assembly and is configured to retain the implant. The elongate shaft 12 may include a proximal end 11 and a distal end 13, wherein a housing in the form of a handle 14 is coupled to the proximal end of the elongate shaft 12. The elongate shaft 12 may be used to hold the implant for advancement of the same through the vasculature to a treatment location. The elongate shaft 12 may further comprise a relatively rigid live-on (or integrated) sheath 51 surrounding an interior portion of the shaft 12 that may reduce unwanted motion of the interior portion of the shaft 12. The live-on sheath 51 can be attached at a proximal end of the shaft 12 proximal to the handle 14, for example at a sheath hub.

Referring to FIGS. 2A and 2B, the elongate shaft 12 may include an implant retention area 16 (shown in FIGS. 2A-B with FIG. 2A showing the implant 70 and FIG. 2B with the implant 70 removed) at its distal end that can be used for this purpose. In some embodiments, the elongate shaft 12 can hold an expandable implant in a compressed state at implant retention area 16 for advancement of the implant 70 within the body. The shaft 12 may then be used to allow controlled expansion of the implant 70 at the treatment location. In some embodiments, the shaft 12 may be used to allow for sequential controlled expansion of the implant 70, as discussed in more detail below. The implant retention area 16 is shown in FIGS. 2A-2B at the distal end of the delivery system 10 but may be in other positions. In some embodiments, the implant 70 may be rotated in the implant retention area 16, such as through the rotation of the inner shaft assembly 18 discussed herein.

As shown in the cross-sectional view of FIGS. 2A-2B, the distal end of the delivery system 10 can include one or more assemblies such as an outer sheath assembly 22, a mid shaft assembly 21, a rail assembly 20, an inner shaft assembly 18, and a nose cone assembly 31 as will be described in more detail below. In some embodiments, the delivery system 10 may not have all the assemblies disclosed herein. For example, in some embodiments a full mid shaft assembly may not be incorporated into the delivery system 10. In some embodiments, the assemblies may be in a different radial order than is discussed.

Embodiments of the disclosed delivery system 10 may utilize an inner steerable rail in the rail assembly 20 for steering/deflecting the distal end of the elongate shaft 12, thereby allowing the implant to be more easily and accurately positioned in a patient's body. As discussed in detail below, the steerable rail can be, for example, a rail shaft that extends through the elongate shaft 12 from the handle 14 generally to the distal end of the elongate shaft 12. In some embodiments, the steerable rail has a distal end that ends proximal to the implant retention area 16. A user can manipulate the bending of the distal end of the rail, thereby bending the rail in a desired direction. In preferred embodiments, the rail has more than one bend along its length, thereby providing multiple planes of deflection. The rail preferably deflects the elongate shaft 12 in at least two planes. As the rail is bent, it presses against the other assemblies to bend them as well, and thus the other assemblies of the elongate shaft 12 can be configured to steer along with the rail as a cooperating single unit, thus providing full steerability along the distal end of the elongate shaft 12.

Once the rail is steered into a desired location in a patient's body, the implant 70 can be advanced along or relative to the rail through the movement of the other sheaths/shafts relative to the rail and released into the body. For example, the rail can be bent into a desired position within the body, such as to direct the implant 70 towards the native mitral valve or other valve for implantation (e.g., aortic, tricuspid, pulmonary, etc.). The other assemblies (e.g., the outer sheath assembly 22, the mid shaft assembly 21, the inner assembly 18, and the nose cone assembly 31) can passively follow the bends of the rail. Further, the other assemblies (e.g., the outer sheath assembly 22, the mid shaft assembly 21, the inner assembly 18, and the nose cone assembly 31) can be advanced together (e.g., relatively together, sequentially, simultaneously, almost simultaneously, at the same time, closely at the same time) relative to the rail while maintaining the implant 70 in the compressed position without releasing or expanding the implant 70 (e.g., within the implant retention area 16). The other assemblies (e.g., the outer sheath assembly 22, the mid shaft assembly 21, the inner assembly 18, and the nose cone assembly 31) can be advanced distally or proximally together relative to the rail. In some embodiments, only the outer sheath assembly 22, mid shaft assembly 21, and inner assembly 18 are advanced together over the rail. Thus, the nose cone assembly 31 may remain in the same position. The assemblies can be individually, sequentially, or simultaneously, translated relative to the inner assembly 18 in order to release the implant 70 from the implant retention area 16.

Figure 2C:
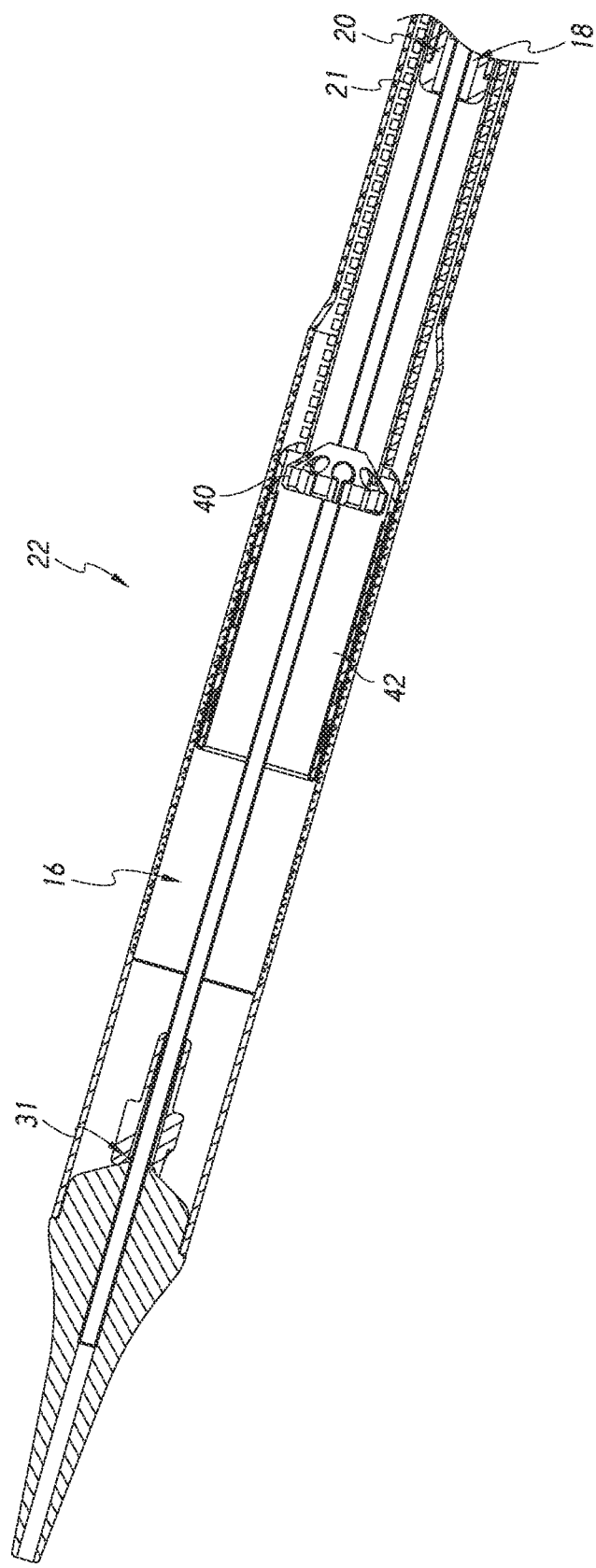
FIG. 2C shows a partial cross-sectional view of the distal end of the delivery system of FIG. 1 with certain shaft assemblies translated along the rail assembly.

FIG. 2C illustrates the sheath assemblies, specifically the outer sheath assembly 22, the mid shaft assembly 21, the inner shaft assembly 18, and the nose cone assembly 31 having translated distally together along the rail assembly 20. In some embodiments, the outer sheath assembly 22, the mid shaft assembly 21, the inner shaft assembly 18, and the nose cone assembly 31 translate together (e.g., relatively together, sequentially with one actuator, simultaneously, almost simultaneously, at the same time, closely at the same time). This distal translation can occur while the implant 70 remains in a compressed configuration within the implant retention area 16.

As shown in FIGS. 2A-2C and as further shown in FIGS. 4-8, starting with the outermost assembly, the delivery system may include an outer sheath assembly 22 forming a radially outer covering, or sheath, to surround an implant retention area 16 and prevent the implant from radially expanding. Specifically, the outer sheath assembly 22 may prevent radial expansion of the distal end of the implant from radially expanding. Moving radially inward and referring to FIG. 5, the mid shaft assembly 21 may be composed of a mid shaft hypotube 43 with its distal end attached to an outer retention member 42 or outer retention ring for radially retaining a portion of the implant in a compacted configuration, such as a proximal end of the implant 70. The mid shaft assembly 21 may be located within a lumen of the outer sheath assembly 22. Moving further inwards, and referring to FIG. 6A, the rail assembly 20 may be configured for steerability, as mentioned above and further described below. The rail assembly 20 may be located within a lumen of the mid shaft assembly 21. Moving further inwards and referring to FIG. 7, the inner shaft assembly 18 may be composed of an inner shaft with its distal end attached to inner retention member or inner retention ring 40 (such as a PEEK ring) for axially retaining the prosthesis, for example the proximal end of the prosthesis. The inner shaft assembly 18 may be located within a lumen of the rail assembly 20. Further, and referring to FIG. 8, the most radially-inward assembly may be the nose cone assembly 31 which includes the nose cone shaft 27 having its distal end connected to the nose cone 28. The nose cone 28 can have a tapered tip. The nose cone assembly 31 is preferably located within a lumen of the inner shaft assembly 18. The nose cone assembly 31 may include a lumen for a guide wire to pass therethrough.

The elongate shaft 12 and its assemblies, more specifically the nose cone assembly 31, inner assembly 18, rail assembly 20, mid shaft assembly 21, and outer sheath assembly 22, can be collectively configured to deliver an implant 70 positioned within the implant retention area 16 (shown in FIG. 2A) to a treatment location. One or more of the assemblies may then be moved to allow the implant 70 to be released at the treatment location. For example, one or more of the assemblies may be movable with respect to one or more of the other assemblies. The handle 14 may include one or more motors, or other components, that may be used to actuate the various assemblies. The implant 70 may be controllably loaded onto the delivery system 10 and then later deployed within the body. Further, the handle 14 can provide steering to the rail assembly 20, providing for bending/flexing/steering of the distal end of the elongate shaft 12.

Referring to FIGS. 2A-2C, the inner retention member 40, the outer retention member 42, and the outer sheath assembly 22 can cooperate to hold the implant 70 in a compacted configuration. In FIG. 2A, the inner retention member 40 is shown engaging struts 72 (marked in FIG. 3A) at the proximal end 301 of the implant 70. For example, slots located between radially extending teeth on the inner retention member 40 can receive and engage the struts 72 which may end in mushroom-shaped tabs 74 on the proximal end of the implant 70 (marked in FIG. 3A). The mid shaft assembly 21 can be positioned over the inner retention member 40 so that the first end 301 of the implant 70 (marked in FIG. 3A) is trapped between the inner retention member 40 and the outer retention member 42, thereby securely attaching it to the delivery system 10 between the mid shaft assembly 21 and the inner retention member 40. The outer sheath assembly 22 can be positioned to cover the second end 303 of the implant 70 (marked in FIG. 3A).

The outer retention member 42 may be attached to a distal end of the mid shaft hypotube 43 which can in turn be attached to a proximal tube 44 at a proximal end (marked in FIG. 5), which in turn can be attached at a proximal end to the handle 14. The outer retention member 42 can provide further stability to the implant 70 when in the compressed position. The outer retention member 42 can be positioned over the inner retention member 40 so that the proximal end of the implant 70 is trapped therebetween, securely attaching it to the delivery system 10. The outer retention member 42 can encircle a portion of the implant 70, preferably the first end 301, thus preventing the implant 70 from fully expanding. Further, the mid shaft assembly 21 can be translated proximally with respect to the inner assembly 18 into the outer sheath assembly 22, thus exposing a first end 301 of the implant 70 held within the outer retention member 42. In this way the outer retention member 42 can be used to help secure an implant 70 to or release it from the delivery system 10. The outer retention member 42 may have a cylindrical or elongate tubular shape and may be referred to as an outer retention ring, though the particular shape is not limiting.

As shown in FIG. 2A, the distal anchors 80 (marked in FIG. 3A) extend in a generally distal direction (as illustrated, axially away from the main body of the implant frame and away from the handle of the delivery system) when the implant is compressed for delivery. The distal anchors 80 can be restrained in this delivered configuration by the outer sheath assembly 22. Accordingly, when the outer sheath 22 is withdrawn proximally, the distal anchors 80 can flip positions (e.g., bend approximately 180 degrees) to a deployed configuration (e.g., pointing generally proximally). The flipping of the distal anchors occurs due to a bias or shape-memory preset, which causes the anchors to flip in the absence of external forces. FIG. 2A also shows the proximal anchors (see 82 in FIG. 3A) extending distally in their delivered configuration within the outer sheath assembly 22. In other embodiments, the distal anchors 80 can extend generally proximally while in the delivered configuration and compressed against the body of the implant frame, thereby eliminating the need to flip during deployment.

The delivery system 10 may be provided to users with an implant 70 preinstalled. In other embodiments, the implant 70 can be loaded onto the delivery system 10 shortly before use, such as by a physician or nurse.

FIGS. 4-8 illustrate further views of delivery system 10 with different assemblies translated proximally and described in detail.

Figure 4:
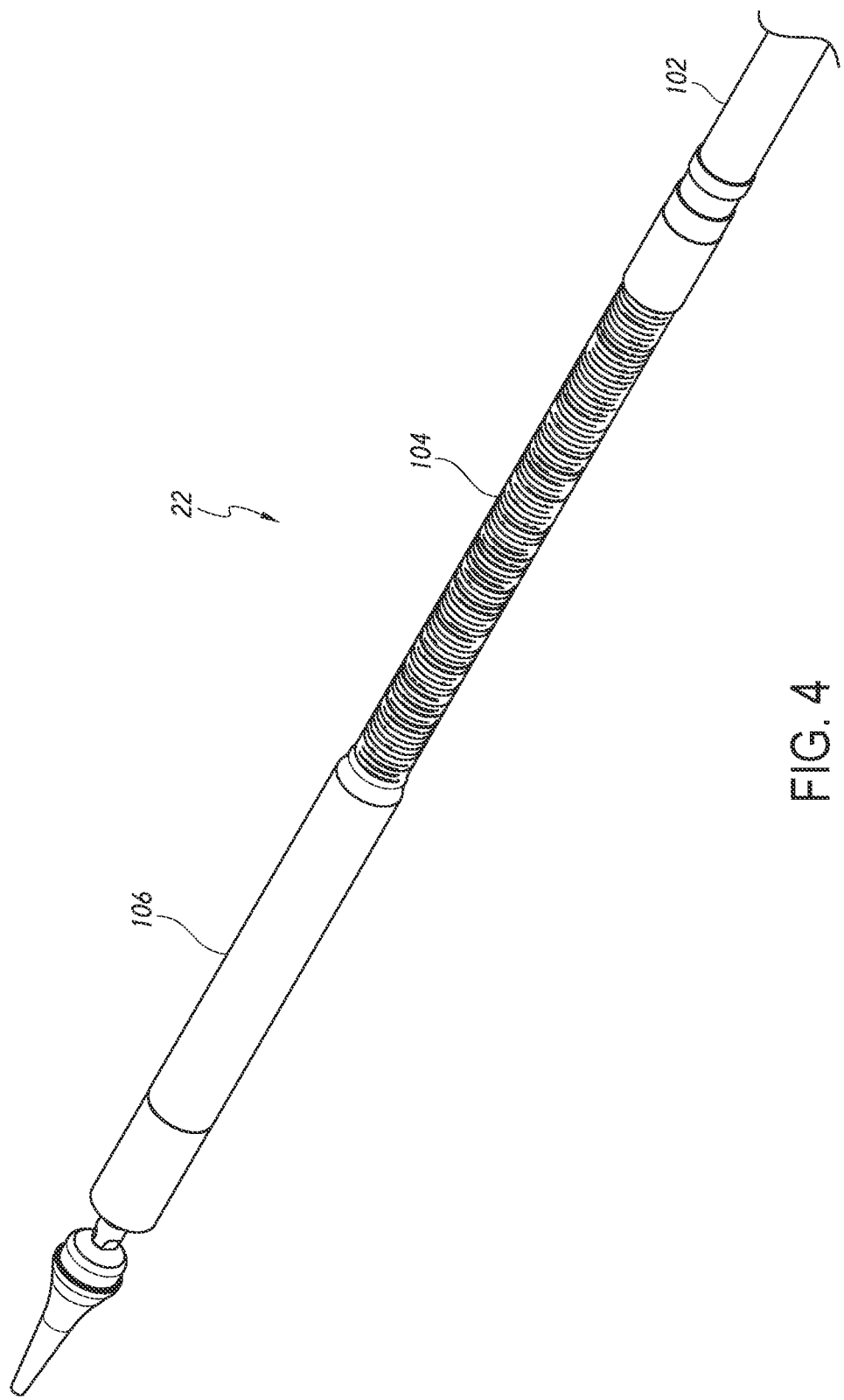
FIG. 4 shows a perspective view of the distal end of the delivery system of FIG. 1.

Starting with the outermost assembly shown in FIG. 4, the outer sheath assembly 22 can include an outer proximal shaft 102 directly attached to the handle 14 at its proximal end and an outer hypotube 104 attached at its distal end. A capsule 106 can then be attached generally at the distal end of the outer hypotube 104. In some embodiments, the capsule 106 can be 28 French or less in size. These components of the outer sheath assembly 22 can form a lumen for the other subassemblies to pass through.

A capsule 106 can be located at a distal end of the outer proximal shaft 102. The capsule 106 can be a tube formed of a plastic or metal material. In some embodiments, the capsule 106 is formed of ePTFE or PTFE. In some embodiments, this capsule 106 is relatively thick to prevent tearing and to help maintain a self-expanding implant in a compacted configuration. In some embodiments the material of the capsule 106 is the same material as the coating on the outer hypotube 104. As shown, the capsule 106 can have a diameter larger than the outer hypotube 104, though in some embodiments the capsule 106 may have a similar diameter as the hypotube 104. In some embodiments, the capsule 106 may include a larger diameter distal portion and a smaller diameter proximal portion. In some embodiments, there may be a step or a taper between the two portions. The capsule 106 can be configured to retain the implant 70 in the compressed position within the capsule 106. Further construction details of the capsule 106 are discussed below.

The outer sheath assembly 22 is configured to be individually slidable with respect to the other assemblies. Further, the outer sheath assembly 22 can slide distally and proximally relative to the rail assembly 20 together with the mid shaft assembly 21, inner assembly 18, and nose cone assembly 31.

Figure 5:
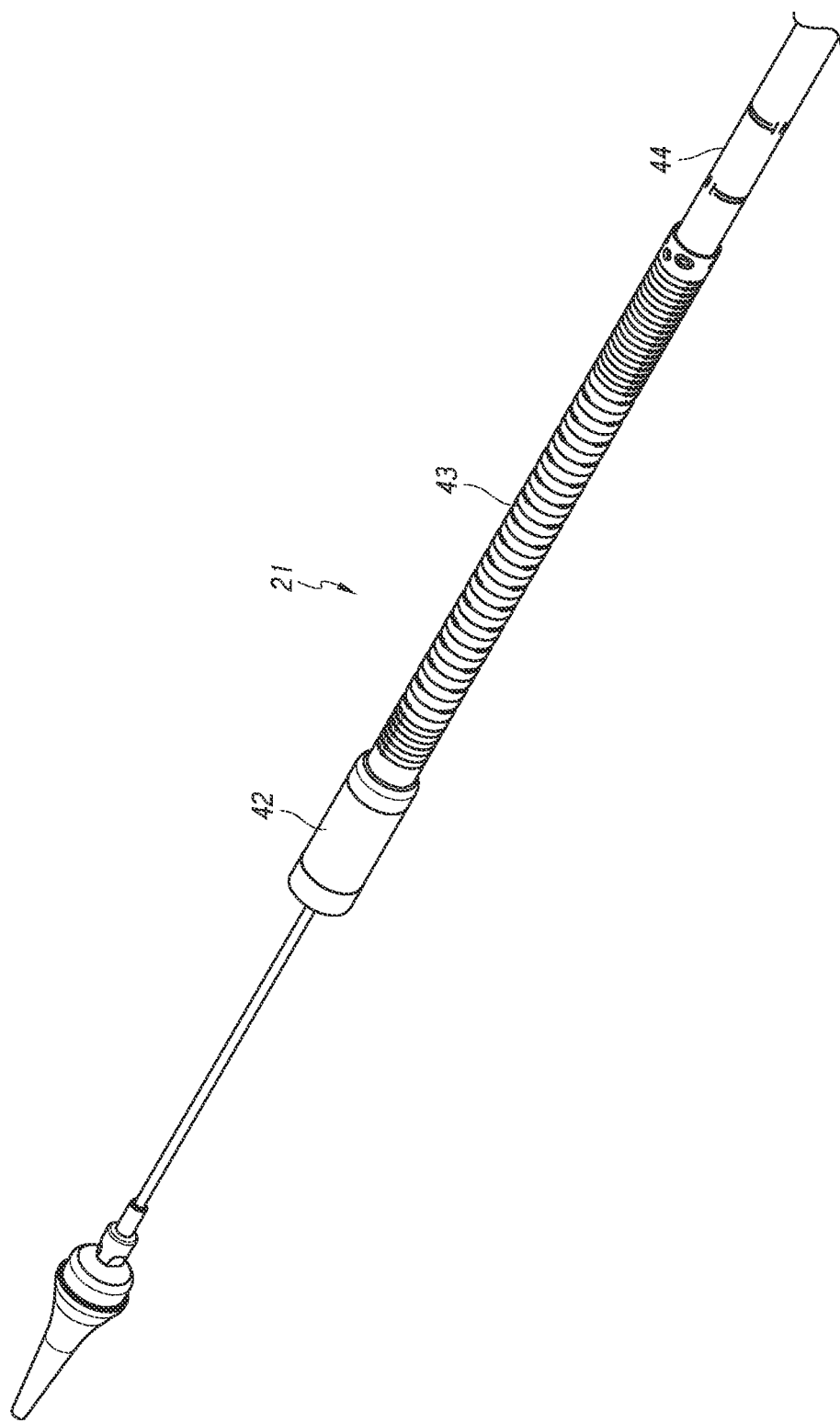
FIG. 5 show components of the delivery system of FIG. 4 with the outer sheath assembly moved proximally and out of view.

Moving radially inwardly, the next assembly is the mid shaft assembly 21. FIG. 5 shows a similar view as FIG. 4, but with the outer sheath assembly 22 removed, thereby exposing the mid shaft assembly 21.

The mid shaft assembly 21 can include a mid shaft hypotube 43 generally attached at its proximal end to a mid shaft proximal tube 44, which in turn can be attached at its proximal end to the handle 14, and an outer retention ring 42 located at the distal end of the mid shaft hypotube 43. Thus, the outer retention ring 42 can be attached generally at the distal end of the mid shaft hypotube 43. These components of the mid shaft assembly 21 can form a lumen for other subassemblies to pass through.

The outer retention member 42 can be configured as a prosthesis retention mechanism that can be used to engage with the implant 70, as discussed with respect to FIG. 2A. For example, the outer retention member 42 may be a ring or covering that is configured to radially cover the struts 72 on the implant 70 (marked in FIG. 3A). The outer retention member 42 can also be considered to be part of the implant retention area 16, and may be at the proximal end of the implant retention area 16. With struts or other parts of an implant 70 engaged with the inner retention member 40, the outer retention member 42 can cover both the implant 70 and the inner retention member 40 to secure the implant 70 on the delivery system 10. Thus, the implant 70 can be sandwiched between the inner retention member 40 of the inner shaft assembly 18 and the outer retention member 42 of the mid shaft assembly 21.

The mid shaft assembly 21 is disposed so as to be individually slidable with respect to the other assemblies. Further, the mid shaft assembly 21 can slide distally and proximally relative to the rail assembly 20 together with the outer sheath assembly 22, mid inner assembly 18, and nose cone assembly 31.

Figure 6A:
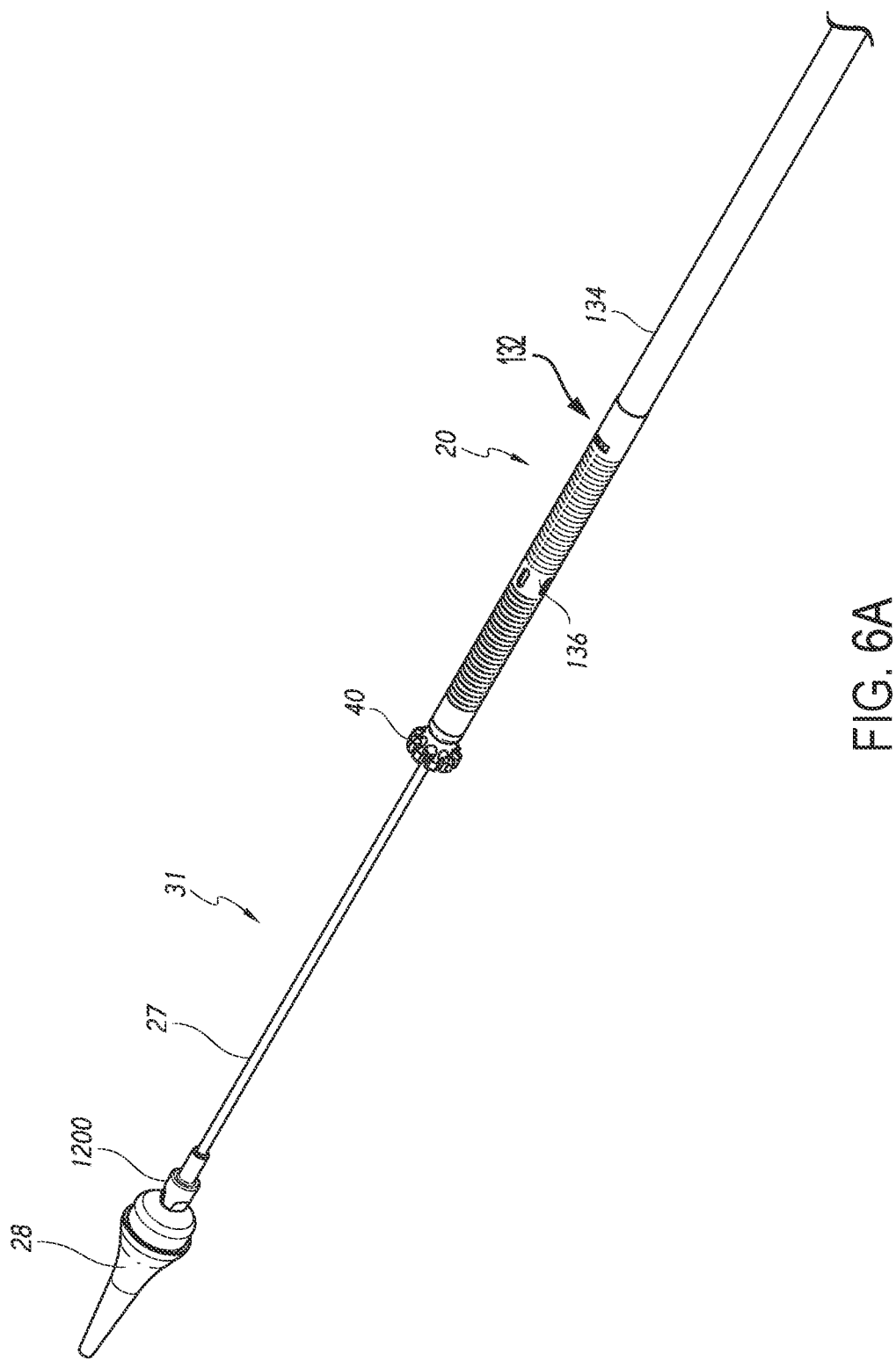
FIG. 6A show components of the delivery system of FIG. 5 with the mid shaft assembly moved proximally and out of view.
Figure 6B:
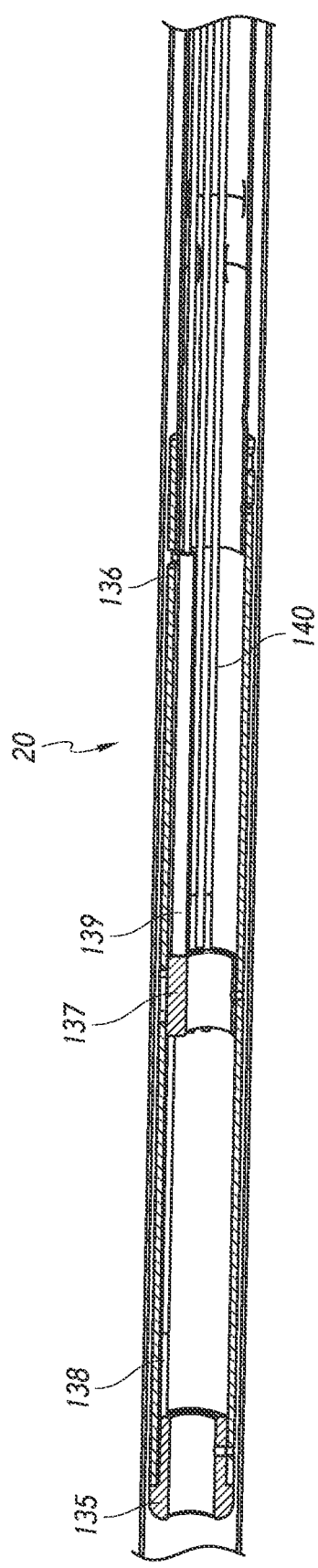
FIG. 6B illustrates a cross-section of the rail assembly.

Next, radially inwardly of the mid shaft assembly 21 is the rail assembly 20. FIG. 6A shows approximately the same view as FIG. 5, but with the mid shaft assembly 21 removed, thereby exposing the rail assembly 20. FIG. 6B further shows a cross-section of the rail assembly 20 to view the pull wires. The rail assembly 20 can include a rail shaft 132 (or rail) generally attached at its proximal end to the handle 14. The rail shaft 132 may be made up of a rail proximal shaft 134 directly attached to the handle at a proximal end and a rail hypotube 136 attached to the distal end of the rail proximal shaft 134. The rail hypotube 136 may further include an atraumatic rail tip at its distal end. Further, the distal end of the rail hypotube 136 can abut a proximal end of the inner retention member 40, as shown in FIG. 6A. In some embodiments, the distal end of the rail hypotube 136 can be spaced away from the inner retention member 40. These components of the rail shaft assembly 20 can form a lumen for the other subassemblies to pass through.

As shown in FIG. 6B, attached to an inner surface of the rail hypotube 136 are one or more pull wires which can be used apply forces to the rail hypotube 136 and steer the rail assembly 20. The pull wires can extend distally from the handle 14 to the rail hypotube 136. In some embodiments, pull wires can be attached at different longitudinal locations on the rail hypotube 136, thus providing for multiple bending locations in the rail hypotube 136, allowing for multi-dimensional steering. The rail hypotube 136 may allow for deflection of the elongate shaft 20 in at least two planes.

In some embodiments, a distal pull wire 138 can extend to a distal section of the rail hypotube 136 and two proximal pull wires 140 can extend to a proximal section of the rail hypotube 136, however, other numbers of pull wires can be used, and the particular amount of pull wires is not limiting. For example, two pull wires can extend to a distal location and a single pull wire can extend to a proximal location. In some embodiments, ring-like structures attached inside the rail hypotube 136, known as pull wire connectors, can be used as attachment locations for the pull wires, such as proximal ring 137 and distal ring 135. In some embodiments, the rail assembly 20 can include a distal pull wire connector in the form of distal ring 135 and a proximal pull wire connector in the form of proximal ring 137. In some embodiments, the pull wires can directly connect to an inner surface of the rail hypotube 136.

The distal pull wire 138 can be connected (either on its own or through a connector such as distal ring 135) generally at the distal end of the rail hypotube 136. The proximal pull wires 140 can connect (either on its own or through a connector such as proximal ring 137) at a location approximately one quarter, one third, or one half of the length up the rail hypotube 136 from the proximal end. In some embodiments, the distal pull wire 138 can pass through a small diameter pull wire lumen 139 (e.g., tube, hypotube, cylinder) attached on the inside of the rail hypotube 136. This can prevent the wires 138 from pulling on the rail hypotube 136 at a location proximal to the distal connection. Further, the lumen 139 can act as compression coils to strengthen the proximal portion of the rail hypotube 136 and prevent unwanted bending. Thus, in some embodiments the lumen 139 is only located on the proximal half of the rail hypotube 136. In some embodiments, multiple lumens 139, such as spaced longitudinally apart or adjacent, can be used per distal pull wire 138. In some embodiments, a single lumen 139 is used per distal pull wire 138. In some embodiments, the lumen 139 can extend into the distal half of the rail hypotube 136. In some embodiments, the lumen 139 is attached on an outer surface of the rail hypotube 136. In some embodiments, the lumen 139 is not used.

For the pair of proximal pull wires 140, the wires can be spaced approximately 180 degrees from one another to allow for steering in both directions. Similarly, if a pair of distal pull wires 138 is used, the wires can be spaced approximately 180 degrees from one another to allow for steering in both directions. In some embodiments, the pair of distal pull wires 138 and the pair of proximal pull wires 140 can be spaced approximately 90 degrees from each other. In some embodiments, the pair of distal pull wires 138 and the pair of proximal pull wires 140 can be spaced approximately 0 degrees from each other. However, other locations for the pull wires can be used as well and the illustrated location of the pull wires is not limiting. In some embodiments, the distal pull wire 138 can pass through a lumen 139 attached within the lumen of the rail hypotube 136. This can prevent an axial force on the distal pull wire 138 from creating a bend in a proximal section of the rail hypotube 136.

The rail assembly 20 is disposed so as to be slidable over the inner shaft assembly 18 and the nose cone assembly 31. In some embodiments, the outer sheath assembly 22, the mid shaft assembly 21, the inner shaft assembly 18, and the nose cone assembly 31 can be configured to slide together along or relative to the rail assembly 20, such as proximally and distally with or without any bending of the rail assembly 20. In some embodiments, the outer sheath assembly 22, the mid shaft assembly 21, the inner shaft assembly 18, and the nose cone assembly 31 can be configured to retain the implant 70 in a compressed position when they are simultaneously slid along or relative to the rail assembly 20.

Figure 7:
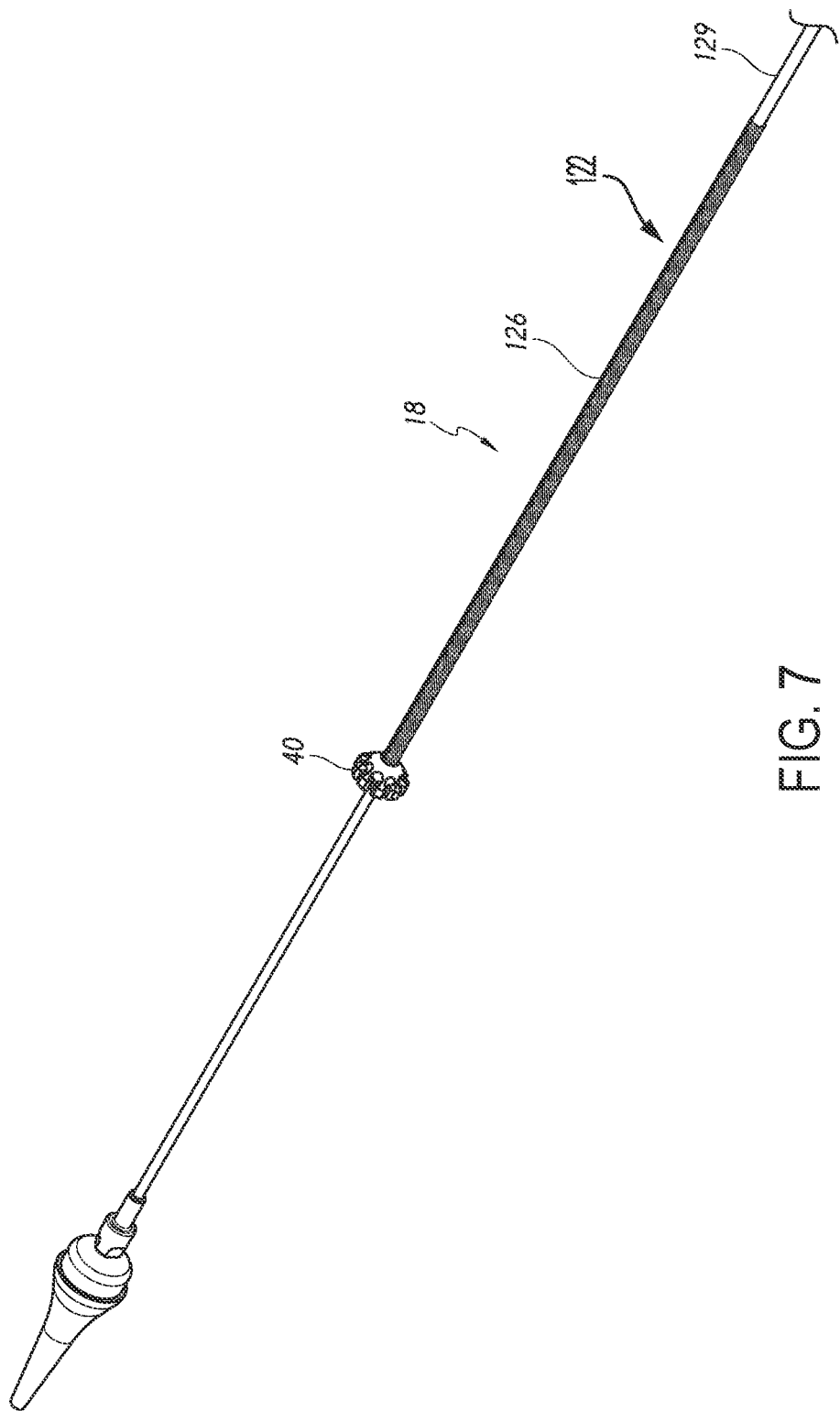
FIG. 7 show components of the delivery system of FIG. 6A with the rail assembly moved proximally and out of view.

Moving radially inwards, the next assembly is the inner shaft assembly 18. FIG. 7 shows approximately the same view as FIG. 6A, but with the rail assembly 20 removed, thereby exposing the inner shaft assembly 18.

The inner shaft assembly 18 can include an inner shaft 122 generally attached at its proximal end to the handle 14, and an inner retention member 40 located at the distal end of the inner shaft 122. The inner shaft 122 itself can be made up of an inner proximal shaft 129 directly attached to the handle 14 at a proximal end and a distal section 126 attached to the distal end of the inner proximal shaft 129. Thus, the inner retention member 40 can be attached generally at the distal end of the distal section 126. These components of the inner shaft assembly 18 can form a lumen for the other subassemblies to pass through.

The inner retention member 40 may be configured as an implant retention mechanism that can be used to engage with the implant 70, as discussed with respect to FIG. 2A. For example, the inner retention member 40 may be a ring and can include a plurality of slots configured to engage with struts 72 on the implant 70 (marked in FIG. 3A). The inner retention member 40 can also be considered to be part of the implant retention area 16 and may be at the proximal end of the implant retention area 16. With struts or other parts of an implant 70 engaged with the inner retention member 40, the outer retention ring 42 can cover both the implant and the inner retention member 40 to secure the prosthesis on the delivery system 10. Thus, the implant 70 can be sandwiched between the inner retention member 40 of the inner shaft assembly 18 and the outer retention member 42 of the mid shaft assembly 21.

The inner shaft assembly 18 is disposed so as to be individually slidable with respect to the other assemblies. Further, the inner assembly 18 can slide distally and proximally relative to the rail assembly 20 together with the outer sheath assembly 22, mid shaft assembly 21, and nose cone assembly 31.

Figure 8:
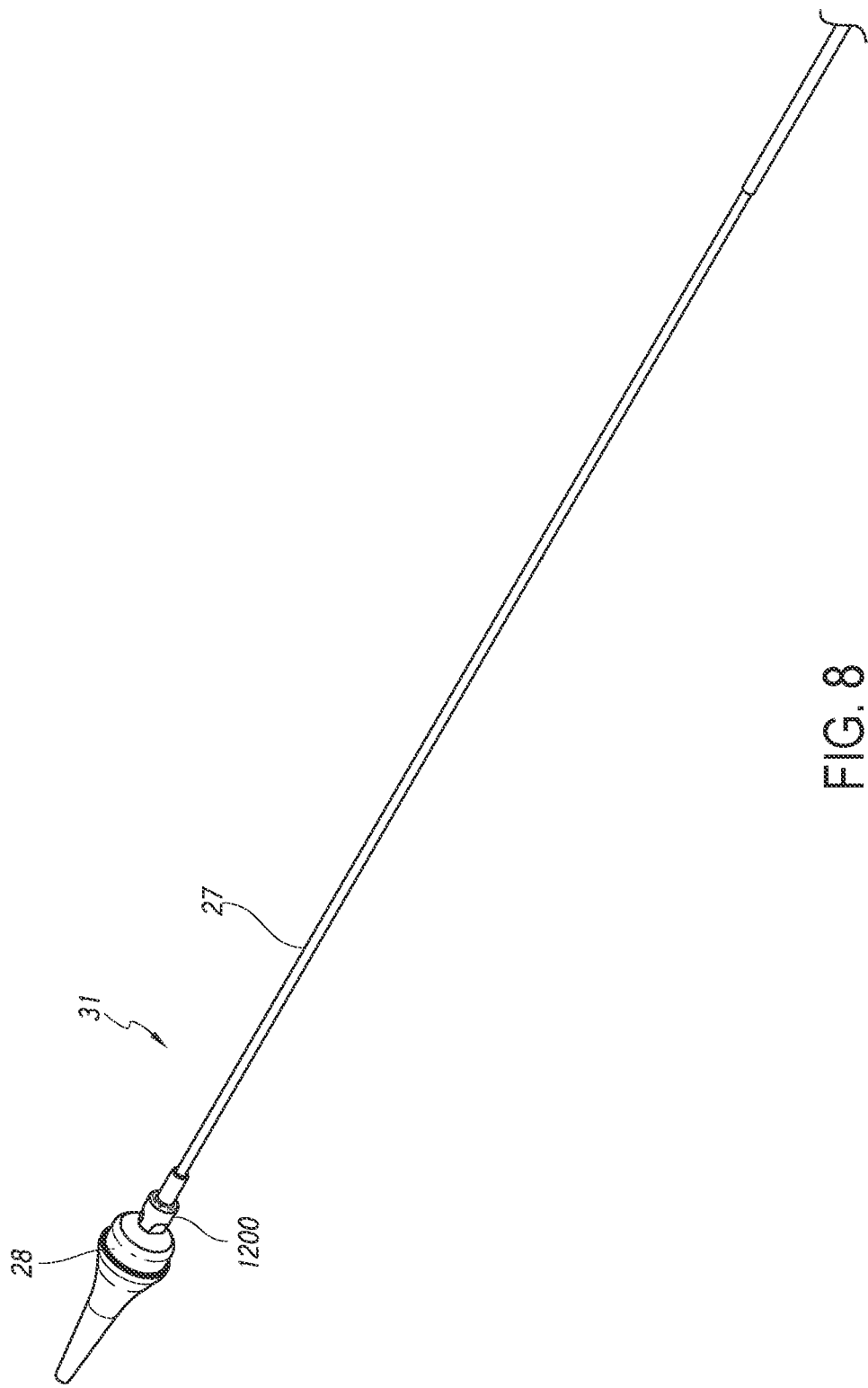
FIG. 8 show components of the delivery system of FIG. 7 with the inner assembly moved proximally and out of view.

Moving further inwardly from the inner shaft assembly 18 is the nose cone assembly 31 seen in FIG. 8. The nose cone assembly may include a nose cone shaft 27, and in some embodiments, may have a nose cone 28 on its distal end. The nose cone 28 may be made of polyurethane for atraumatic entry and to minimize injury to venous vasculature. The nose cone 28 may also be radiopaque to provide for visibility under fluoroscopy.

The nose cone shaft 27 may include a lumen sized and configured to slidably accommodate a guide wire so that the delivery system 10 can be advanced over the guide wire through the vasculature. However, embodiments of the system 10 discussed herein may not use a guide wire and thus the nose cone shaft 27 in certain embodiments may be solid. The nose cone shaft 27 may be connected from the nose cone 28 to the handle, or may be formed of different segments such as the other assemblies. Further, the nose cone shaft 27 may be formed of different materials, such as plastic or metal, similar to those described in detail above. In some embodiments, the nose cone shaft 27 includes a guide wire shield 1200 located on a portion of the nose cone shaft 27.

The nose cone assembly 31 may be disposed so as to be individually slidable with respect to the other assemblies. Further, the nose cone assembly 31 may slide distally and proximally relative to the rail assembly 20 together with the outer sheath assembly 22, mid shaft assembly 21, and inner assembly 18.

In some embodiments, one or more spacer sleeves (not shown) can be used between different assemblies of the delivery system 10. For example, a spacer sleeve can be located concentrically between the mid shaft assembly and the rail assembly 20, generally between the mid shaft hypotube 43 and rail hypotube 136. The spacer sleeve can be generally embedded in the hypotube 43 of the mid shaft assembly 21, such as on an inner surface of the mid shaft assembly 21. In some embodiments, a spacer sleeve can be located concentrically between the rail assembly 20 and the inner assembly 18, generally within the rail hypotube 136. In some embodiments, a spacer sleeve can be used between the outer sheath assembly 22 and the mid shaft assembly 21. In some embodiments, a spacer sleeve can be used between the inner assembly 18 and the nose cone assembly 31. In some embodiments, 4, 3, 2, or 1 of the above-mentioned spacer sleeves can be used. The spacer sleeves can be used in any of the above positions.

As discussed above, the outer sheath assembly 22, the mid shaft assembly 21, the inner assembly 18, and the rail assembly 20 may contain an outer hypotube 104, a mid shaft hypotube, a distal section 126, and a rail hypotube 136, respectively. Each of these hypotubes/sections/shafts can be laser cut to include a number of slots, thereby creating a bending pathway for the delivery system to follow.

Figure 9:
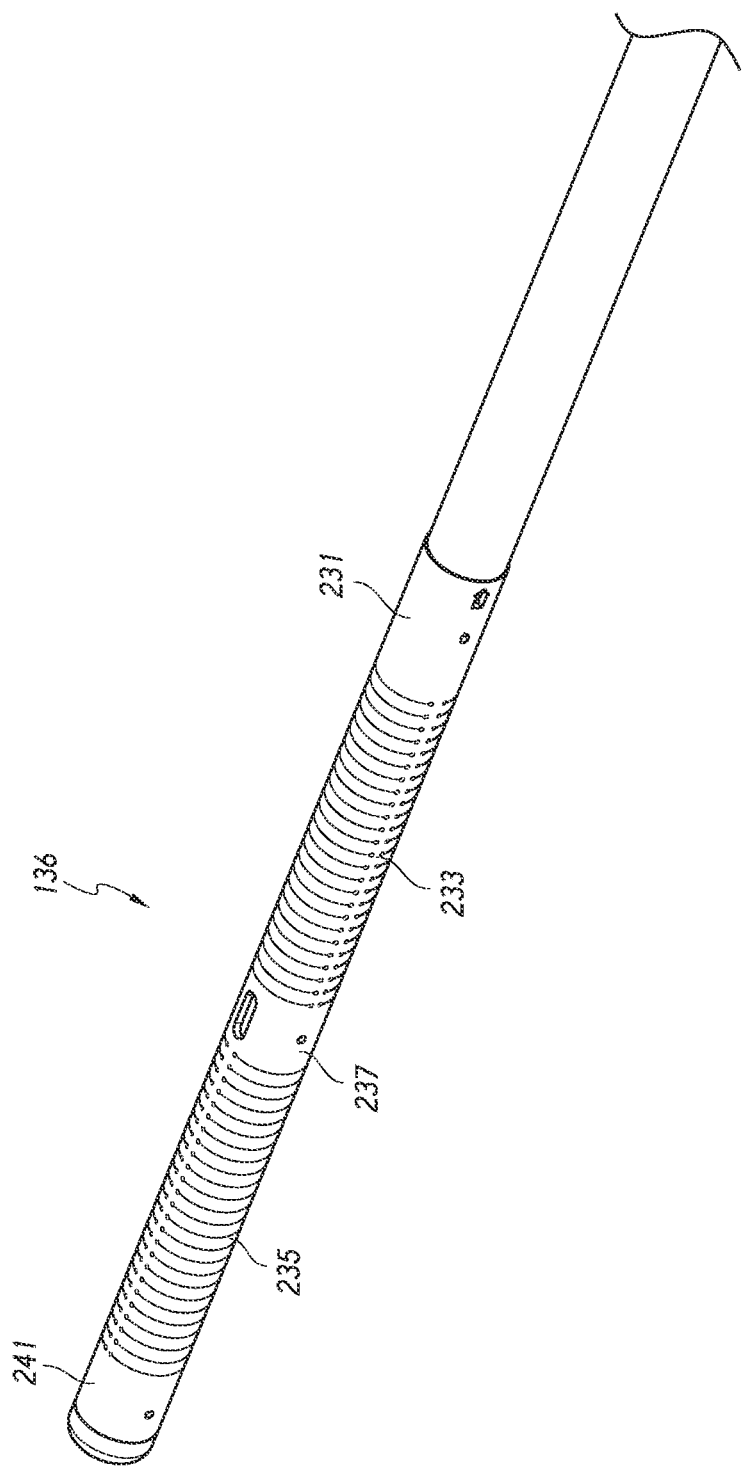
FIG. 9 illustrates an embodiment of a rail assembly.

For example, FIG. 9 shows an embodiment of the rail hypotube 136 (distal end towards the right). The rail hypotube 136 can also contain a number of circumferential slots. The rail hypotube 136 can generally be broken into a number of different sections. At the most proximal end is an uncut (or unslotted) hypotube section 231. Moving distally, the next section is the proximal slotted hypotube section 233. This section includes a number of circumferential slots cut into the rail hypotube 136. Generally, two slots are cut around each circumferential location forming almost half of the circumference. Accordingly, two backbones are formed between the slots extending up the length of the hypotube 136. This is the section that can be guided by the proximal pull wires 140. Moving further distally is the location 237 where the proximal pull wires 140 connect, and thus slots can be avoided. Thus section is just distal of the proximally slotted section.

Distally following the proximal pull wire connection area is the distal slotted hypotube section 235. This section is similar to the proximal slotted hypotube section 233, but has significantly more slots cut out in an equivalent length. Thus, the distally slotted hypotube section 235 provides easier bending than the proximally slotted hypotube section 233. In some embodiments, the proximal slotted section 233 can be configured to experience a bend of approximately 90 degrees with a half inch radius whereas the distal slotted section 235 can bend at approximately 180 degrees within a half inch. Further, as shown in FIG. 9, the spines of the distally slotted hypotube section 235 are offset from the spines of the proximally slotted hypotube section 233. Accordingly, the two sections will achieve different bend patterns, allowing for three-dimensional steering of the rail assembly 20. In some embodiments, the spines can be offset 30, 45, or 90 degrees, though the particular offset is not limiting. In some embodiments, the proximally slotted hypotube section 233 can include compression coils. This allows for the proximally slotted hypotube section 233 to retain rigidity for specific bending of the distally slotted hypotube section 235.

At the distalmost end of the distal slotted hypotube section 235 is the distal pull wire connection area 241 which is again a non-slotted section of the rail hypotube 136.

Referring again to FIG. 1, the elongate shaft 12 and housing in the form of a handle 14 may form a delivery apparatus that is configured to deliver the implant 70 to a location within a patient's body. The delivery system 10 may include at least one motor that is configured to actuate at least a portion of the delivery apparatus. The actuation of at least a portion of the delivery apparatus may include deflection of a portion of the delivery apparatus (including the elongate shaft) or other movement of the delivery apparatus and may include actuation of an operation of the delivery apparatus. The operation may include deployment (whether full or partial) of the implant 70 to the body location, among other operations of the delivery apparatus. The motor may comprise a motor 500 as shown in FIG. 10 or may comprise a plurality of motors 502 shown in FIG. 41 (i.e., at least one motor), among other forms of motors.

As shown in FIG. 1, the housing in the form of the handle 14 may be positioned at the proximal end 11 of the elongate shaft 12. The proximal end 11 of the elongate shaft 12 may be coupled to the handle 14. The handle 14 may include a control device 504 configured to control the at least one motor. The control device 504 as shown in FIG. 1 may include a plurality of buttons; however, in other embodiments other forms of control devices may be utilized. The control device 504 may be positioned on the handle 14 as shown in FIG. 1 or may be located remotely.

Figure 10:
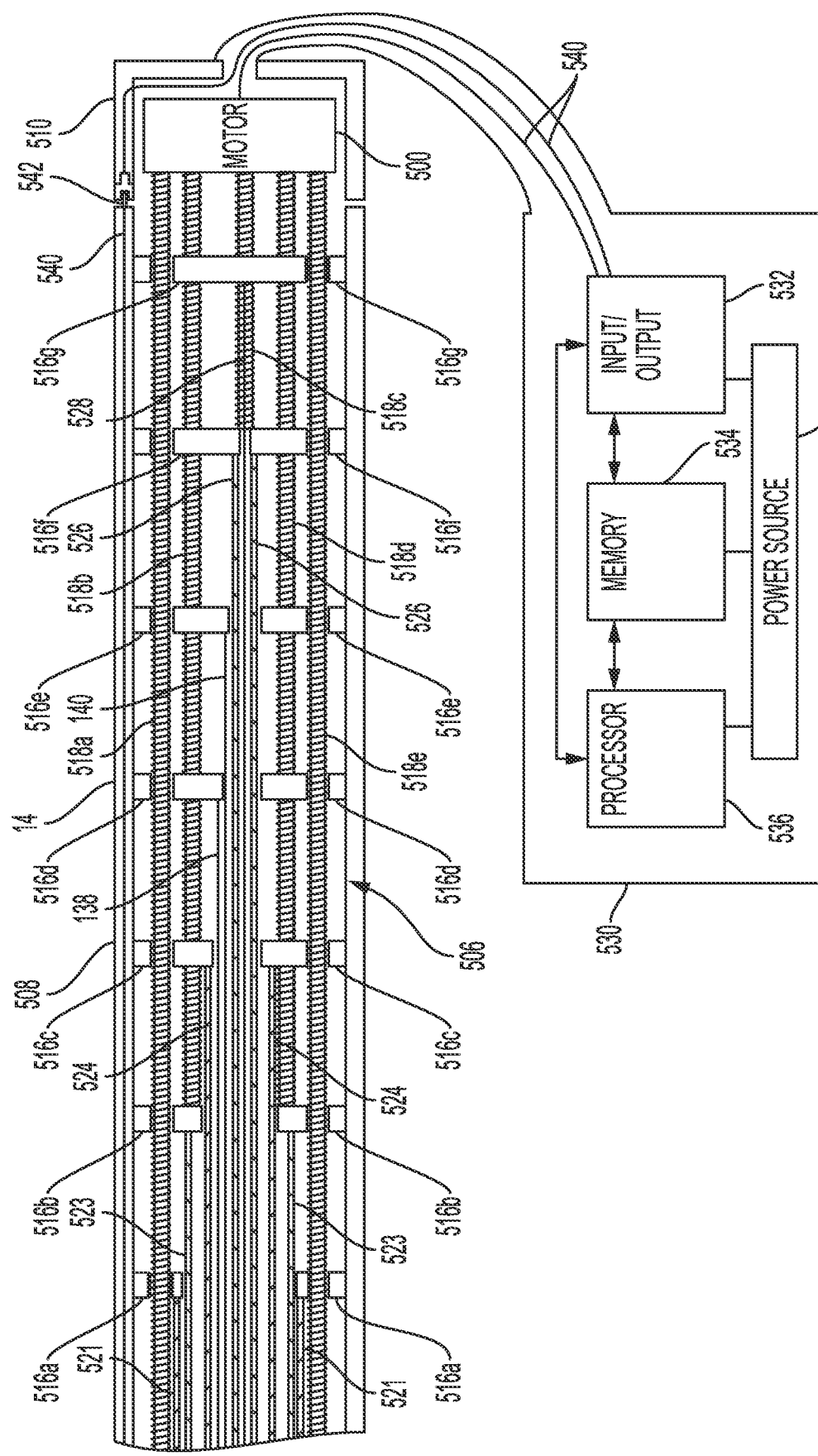
FIG. 10 illustrates a cross sectional view of an embodiment of a delivery system handle and controller.

FIG. 10 illustrates a cross section of the handle 14 including the motor 500 and an actuation mechanism 506 that may be utilized to actuate at least a portion of the delivery apparatus. In various embodiments, the motor and actuation mechanism may be used to actuate pull wires during advancement through the vasculature. The motor and actuation mechanism may be used to actuate to actuate shafts/sheaths for deploying and releasing the implant at the treatment site. The body of the handle 14 may include multiple parts, including a distal portion 508 and a proximal portion 510. The distal portion 508 as shown in FIG. 10 may be configured to retain the actuation mechanism 506 and the proximal portion 510 may be configured to retain the motor 500. In other embodiments, other components may be positioned in respective distal 508 and proximal portions 510, and in certain embodiments the handle 14 may include a single body. In the embodiment shown in FIG. 10, the distal portion 508 and proximal portion 510 may be configured to couple together via a coupler 512, 514 (marked in FIGS. 13 and 14), and may be separable from each other in certain embodiments.

Figure 11:
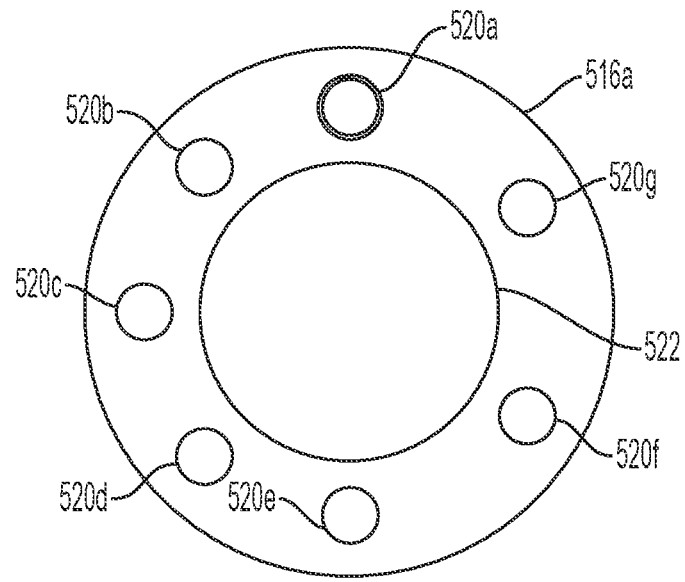
FIG. 11 illustrates a front plan view of an embodiment of an adaptor.
Figure 12:
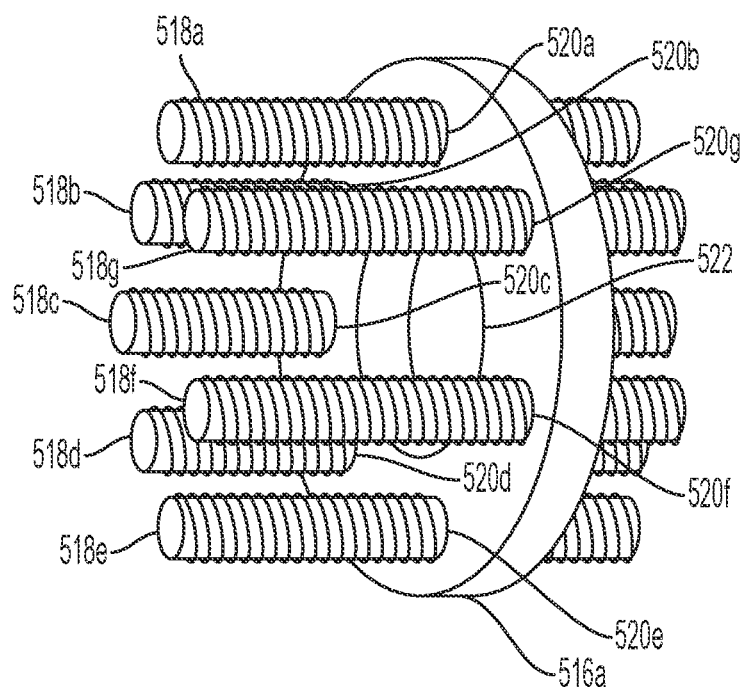
FIG. 12 illustrates a side perspective view of an embodiment of an adaptor and drive rods.

The actuation mechanism 506 may take the form as shown in FIG. 10 and may include a plurality of adaptors 516*a-g* configured to engage with a plurality of drive rods 518*a-g* (drive rods 518*f-g* are marked in FIG. 12). Each adaptor 516*a-g* may comprise a plate or other body including a plurality of apertures. FIG. 11 illustrates a front plan view of the adaptor 516*a*. The adaptor 516*a* as shown in FIG. 11 may include apertures 520*a-g* and 522. The apertures 520*a-g* may each be configured to allow a respective drive rod 518*a-g* to pass therethrough (as represented in FIG. 12). The apertures 520*b-g* may each be configured to be smooth bearing surfaces, that do not engage the respective drive rods 518*b-g*. The aperture 520*a*, however, may be configured with a threaded surface or other surface that engages the drive rod 518*a*. For example, the drive rod 518*a* may include a gear threading and the aperture 520*a* may include a threading that matches the gear threading. Such a configuration allows the drive rod 518*a* to actuate the adaptor 516*a* in two directions (distal and proximal) based on the direction that the drive rod 518*a* is rotating. In other embodiments, other forms of engagement may be utilized.

The central aperture 522 may allow other components of the actuation mechanism 506 such as assembly connectors to pass through the central aperture to couple to the remaining respective adaptors 516*a-g*.

FIG. 12 illustrates a perspective view of adaptor 516*a* with representative drive rods 518*a-g* extending through the apertures 520*a-g*.

The other adaptors 516*b-g* may be configured similarly as the adaptor 516*a*, however, each respective adaptor 516*b-g* may have an aperture that is configured to engage the respective drive rods 518*b-g*, with the remaining apertures comprising smooth bearing surfaces. For example, for adaptor 516*b*, the equivalent aperture to aperture 520*b* may be configured to engage drive rod 518*b* while the remaining equivalent apertures to apertures 520*a*, *c-g* may comprise smooth bearing surfaces. Adaptors 516*c-g* have similar respective apertures configured to engaged respective drive rods 518*c-g*. In this manner, a single drive rod 518*a-g* may be configured to actuate a respective dedicated adaptor 516*a-g*. The remaining drive rods may pass through the remaining adaptors without engaging the adaptor.

Referring again to FIG. 10, the adaptors 516*a-g* may be configured to slide within the interior cavity of the housing comprising the handle 14. The outer surfaces of the adaptors 516*a-g* for example, may be positioned on a track within the handle 14 or otherwise configured to slide or move within the handle 14.

The drive rods 518*a-g* may extend longitudinally along the interior of the handle 14 and may be configured to engage a respective adaptor 516*a-g*. For example, FIG. 10 illustrates the adaptor 516*a* engaged by drive rod 518*a* and the adaptor 516*g* engaged by drive rod 518*e* (in a configuration in which adaptor 516*g* was configured to be engaged by drive rod 518*e*, other configurations, e.g., the adaptor 516*g* being engaged by drive rod 518*g*, may be utilized). Proximal ends of the drive rods 518*a-g* may be configured to engage and be actuated by motor 500.

The adaptors 516*a-g* may be coupled to assembly connectors that couple to respective portions of the assemblies (the outer sheath assembly 22, the mid shaft assembly 21, the rail assembly 20, the inner assembly 18, and the nose cone assembly 31) including the pull wire assemblies 138, 140. In certain embodiments, the adaptors 516*a-g* may couple to particular components comprising each of the assemblies, for example, the adaptor 516*a* may couple directly to the nose cone shaft 27 in certain embodiments. The coupling of the adaptors 516*a-g* to the assembly connectors may be such that the adaptor 516*a* couples to an assembly connector 521 for the outer sheath assembly 22.

The adaptor 516b may couple to an assembly connector 523 for the mid shaft assembly 21. The adaptor 516c may couple to an assembly connector 524 for the rail assembly 20. The adaptor 516d may couple to an assembly connector for the distal pull wires 138 or may couple to the distal pull wires 138 directly. The adaptor 516e may couple to an assembly connector for the proximal pull wires 140 or may couple to the proximal pull wires 140 directly. The adaptor 516f may couple to an assembly connector 526 for the inner assembly 18. The adaptor 516g may couple to an assembly connector 528 for the nose cone assembly 31. The assembly connectors 521, 523, 524, 526, 528 may comprise sheaths that extend concentrically over each other, or may comprise rods, wires, or other forms of connectors. The assembly connectors 521, 523, 524, 526, 528 may be configured to pass through the central aperture of the respective adaptors 516a-g (for example aperture 522 shown in FIG. 11).

The assembly connectors 521, 523, 524, 526, 528 may have a proximal portion coupled to the respective adaptor 516a, b, c, f, g and a distal portion coupled to a portion of the respective assembly in order to actuate the respective assembly. For example, the assembly connector 521 may couple to the outer sheath assembly 22 such that movement of the assembly connector 521 moves the outer covering, or sheath of the outer sheath assembly 22 to expose the implant 70 in the capsule 106. The assembly connector 523 may couple to the mid shaft assembly 21 such that movement of the assembly connector 523 moves the outer retention member 42. The assembly connector 524 may couple to the rail assembly 20 such that movement of the assembly connector 524 moves the rail assembly 20. The movement of the adaptors 516d and 516e may move the respective pull wires 138, 140. The assembly connector 526 may couple to the inner assembly 18 such that movement of the assembly connector 526 moves the inner retention member 40. The assembly connector 528 may couple to the nose cone assembly 31 such that movement of the assembly connector 528 moves the nose cone 28. The respective drive rod 518a-g may thus be actuated by the motor 500 to selectively move a respective adaptor 516a-g and accordingly a respective portion of the assemblies (the outer sheath assembly 22, the mid shaft assembly 21, the rail assembly 20, the inner assembly 18, and the nose cone assembly 31).

The motion of the assemblies (the outer sheath assembly 22, the mid shaft assembly 21, the rail assembly 20, the inner assembly 18, and the nose cone assembly 31) may be a translation of the respective assemblies, which may include the pull wires 138, 140, to produce the desired movement (e.g., deflection) or operation (e.g., deployment of the implant). For example, the motor 500 may be configured to translate a rail shaft of the rail assembly 20 relative to an inner sheath of the inner assembly 18 and the outer sheath of the outer sheath assembly 22. The motor 500 may be configured to translate the outer sheath of the outer sheath assembly 22 relative to the inner sheath of the inner assembly 18 in certain embodiments. The motor 500 may be configured to translate any of the assemblies relative to each other to produce a desired result. The motor 500 may be configured to steer the rail assembly 20, for example, by actuating the pull wires 138, 140. Other movements may include actuating a depth of the elongate shaft 12, and actuating an operation of the elongate shaft 12, for example a full or partial deployment of the implant 70.

In other embodiments, the actuation of the delivery apparatus with the motor 500 may occur in a different manner than shown in FIG. 10. In one embodiment the configuration of the actuation mechanism 506 may differ from the configuration shown in FIG. 10.

The delivery system 10 may include a controller 530 that is configured to control operation of the motor 500 and thus control actuation of the portion of the delivery apparatus. The controller 530 as shown in FIG. 10 may include an input device and an output device (marked as item 532). The controller 530 may include a memory 534 and a processor 536. The controller may include a power source 538.

The input device and output device 532 may have a plurality of configurations, including electrical ports or terminals that are configured to transmit electrical signals. The input device may be configured to receive signals from the motor 500 as well as from sensors positioned on the delivery system 10. The output device may be configured to transmit signals to the motor 500 or other components of the system 10 which may be received from the processor 536 or other components of the system 10. In certain embodiments, the input device and output device 532 may comprise wireless transmission devices, such as a Wi-Fi or Bluetooth device or other device configured for wireless communication. In an embodiment in which the controller 530 is positioned remotely from the delivery apparatus, the input device and output device 532 may be configured to transmit and receive information via the Internet or other form of communication medium. In other embodiments, other forms of input devices and output devices may be utilized.

The memory 534 may be configured to store programs for operation by the processor 536 as well as other data desired to be stored in the controller 530. The memory 534 may be configured to store and log data, such as regarding the patient and the operation of the delivery apparatus and the motor 500 during a procedure, thereby allowing the system to learn from past events. The learning aspect may be based on an algorithm capable of identifying procedures that have produced positive outcomes in the past, thereby allowing the system to continually refine the procedure to enhance the probability of a successful outcome. Preferably, data could be pooled from different patients, different clinicians and/or different hospitals. The compilation of data could be used to increase precision and improve outcomes in future procedures. This could be achieved, for example, by comparing characteristics of a new patient with patients who have been treated in the past. Data from procedures on past patients with similar anatomies and/or other parameters, such as the patient's gender, age, and health, would be particularly useful. Other parameters could be incorporated into the algorithm, such as the clinician's skill level and amount of experience and/or the facilities available at the hospital. The data may be used in a machine learning algorithm utilizing data from past implantation procedures or from characteristics of the patient.

The memory 534 may comprise various forms of memory including a hard disk, solid state memory, various forms of RAM or ROM, or other forms of memory. In one embodiment, the memory 534 may be configured to be removable from the controller 530 for storage and/or data analysis. Separate memory 534 may be installed into the controller 530 or swapped into or out of the controller 530 as desired for a particular operation.

The processor 536 may be configured to perform processes disclosed herein and may be configured to provide signals to components of the system 10 for example, the motor 500 to perform desired processes. The processor 536 may be configured to operate the motor 500, or at least one motor 500, to actuate at least a portion of the delivery apparatus. The processor 536 may be configured to operate at least one motor 500 to move a portion of the delivery apparatus (e.g., deflect or control a depth of the elongate shaft 12), or perform an operation of the delivery apparatus, which may include deploying the implant 70 from the delivery apparatus. The processor 536 may be configured to execute processes stored in the memory 534. The processor 536 may be configured to receive signals from components of the system 10 such as a control device (for example control device 504) or sensors of the system 10. The processor 536 may be configured to process and perform operations based on those signals. The processor 536 may comprise a microprocessor, or other form of processor as desired. In one embodiment, the processor 536 may comprise a plurality of processors, and in one embodiment may be distributed in a cloud computing environment or the like.

The power source 538 may be configured to provide power to the components of the controller 530 and may be configured to provide power to the motor 500 or other components of the system 10. The power source 538 may comprise one or more batteries according to certain embodiments, which may be rechargeable and detachable from the controller 530 or other components of the system 10 as desired. In one embodiment, the power source 538 may comprise a power plug, such as an AC plug, and may include a power regulator for converting the AC power to a power usable by the system 10. Other forms of power sources 538 (e.g., super capacitors, solar cells, among others) may be used in other embodiments as desired.

The components of the controller 530 may be positioned together as shown in FIG. 10 or may be distributed as desired. The components of the controller 530 may be positioned in a separate housing, or control box, and may be coupled to the delivery apparatus with a cable or the like. FIG. 10 illustrates a cabled connection of the controller 530 to the delivery apparatus. In other embodiments, wireless communication may be possible between one or more components of the controller 530 and the delivery apparatus. In other embodiments, components of the controller 530 may be positioned within the housing of the delivery apparatus, for example, in a configuration shown in FIG. 41.

Power and signal connectors 540 may extend between the controller 530 and the delivery apparatus. For example, a signal connector 540 is shown extending along a portion of the handle 14 and may couple between the distal portion 508 of the handle 14 and the proximal portion 510 at the electrical coupler 542. Power connectors 540 may extend to the motor 500 from the power source 538 of the controller 530.

Figure 13:
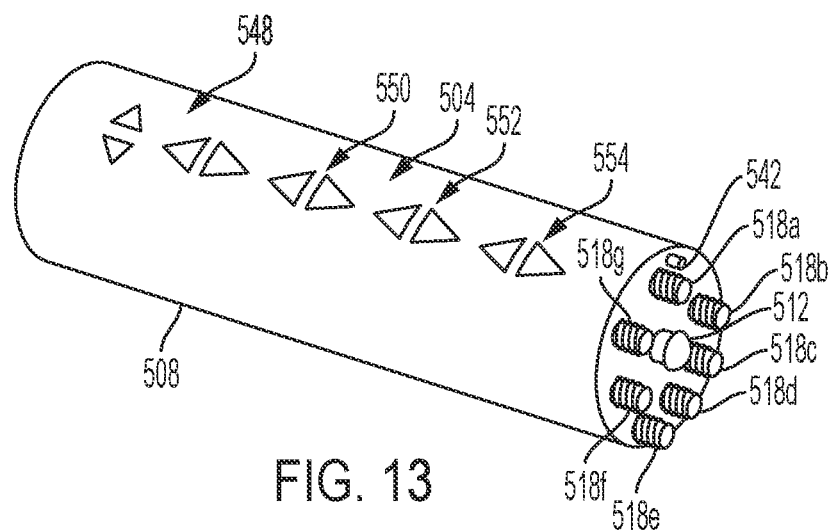
FIG. 13 illustrates a perspective view of the handle shown in FIG. 1.

FIG. 13 illustrates a perspective view of the distal portion 508 of the handle 14. The distal portion 508 of the handle 14 may be configured to separate from the proximal portion 510 (shown in FIG. 14). Such a configuration may allow a particular portion of the handle 14 of the delivery apparatus to be utilized in delivery of an implant, and then separated from another portion (e.g., proximal portion 510) of the handle 14 such that sterilization or discard of the distal portion 508 may occur. This process may separate electrical components of the system 10, which may include the motor 500 positioned within the proximal portion 510, or may include the controller 530, from components that are inserted into or contact portions of the patient's body. This may enhance reusability of the system 10 and reduce the overall complexity associated with sterilizing the system 10. As shown in FIG. 13, proximal portions of the drive rods 518*a-g* may extend proximally from the distal portion 508 of the handle 14, for coupling to respective apertures 544*a-g* in the proximal portion 510 of the handle 14. The proximal portions of the drive rods 518*a-g* may couple to the respective apertures 544*a-g* to allow the motor 500 to engage the drive rods 518*a-g*. The electrical coupler 542 and coupler 512 are also shown protruding from the distal portion 508 of the handle 14.

Figure 14:
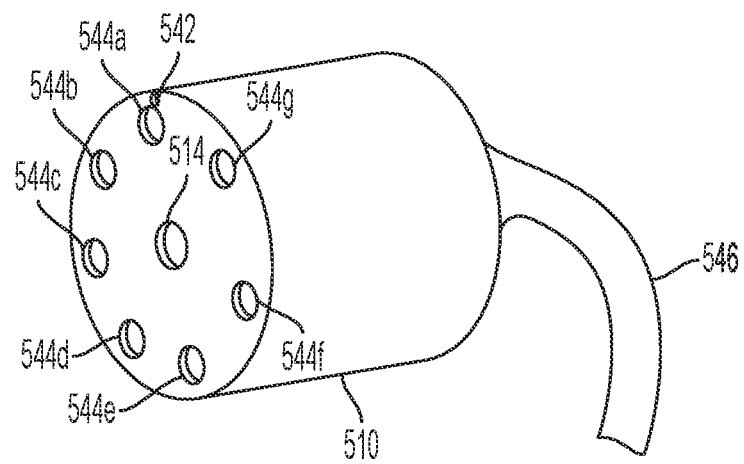
FIG. 14 illustrates a perspective view of a proximal portion of the handle shown in FIG. 1.

FIG. 14 illustrates a perspective view of the proximal portion 510 of the handle 14. The proximal portion 510 may include a cable 546 or other connector that couples the proximal portion 510 to the controller 530, which may be contained in a control box or the like.

Referring again to FIG. 13, the control device 504 is shown on the distal portion 508 of the handle 14 as including a plurality of buttons. The control device 504 may be configured to receive an input from a user to operate the motor 500 and thus actuate a portion of the delivery apparatus. The control device 504 may be configured to send a signal directly to the motor 500 or may be sent to the processor 536 of the controller 530 for processing. The control device 504 may be configured to control deflection and movement of the delivery apparatus. The control device 504 may be configured to control an operation of the delivery apparatus such as deployment of the implant 70. The control device 504 may have a variety of forms, and as shown in FIG. 13 may have portions designated to control certain movements or operations of the delivery apparatus.

The control device 504 of FIG. 13 may include buttons 548 that control the rail assembly 20 and particularly the direction of deflection of the rail assembly 20, which may be in multiple planes. The buttons 548 may be configured to control steering of the rail assembly 20. The user may press the desired button 548 to cause the motor to actuate the delivery apparatus to deflect in the desired direction. The control device 504 of FIG. 13 may include buttons 550 that control the depth of the elongate shaft 12, for example, by sliding the assemblies including the outer sheath assembly 22, the mid shaft assembly 21, the inner assembly 18, and the nose cone assembly 31, relative to the rail assembly 20. The buttons 550 may allow the user to increase or decrease the depth. The control device 504 of FIG. 13 may include buttons 552 that actuate deployment of the implant 70. For example, the buttons 552 may cause the motor to actuate the delivery apparatus to retract the outer sheath assembly 22 and the mid shaft assembly 21 to deploy the implant 70. The control device 504 of FIG. 13 may include buttons 554 that actuate movement of the nose cone assembly 31, to advance or retract the nose cone 28. Various configurations of control may be utilized to deflect the delivery apparatus or to perform operations of the delivery apparatus. The control signals from the control device 504 may be sent directly to the motor 500 for operation or may be sent to the processor 536 for the processor 536 to operate the motor 500 to actuate at least a portion of the delivery apparatus. The configuration of the control device 504 may be varied in other embodiments.

Figure 15:
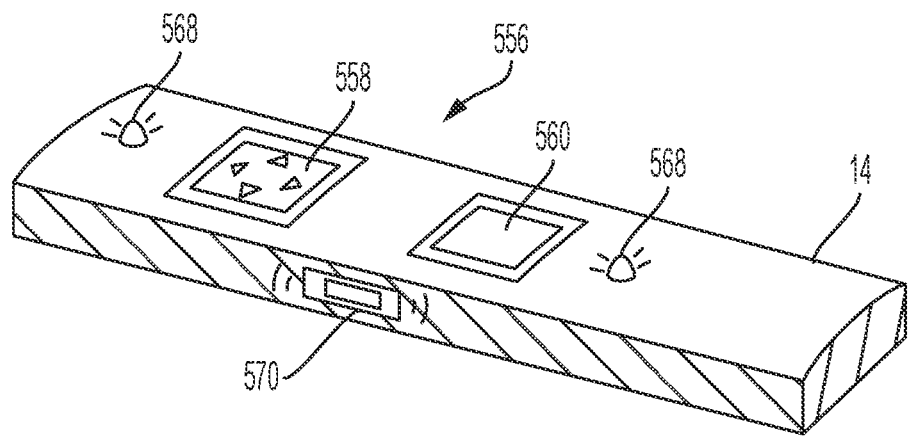
FIG. 15 illustrates a partial cross section view of an embodiment of a portion of a handle.

FIG. 15, for example, illustrates a cross sectional portion of a part of the handle 14 in which a control device 556 comprises one or more of a touch pad 558 and a touch screen 560 on the handle 14. The touch pad 558 may be configured for the user to provide directional control for the delivery apparatus via the rail assembly 20. The touch screen 560 may be configured for the user to provide other controls to the delivery apparatus, including depth control, deployment of the implant 70, or movement of one or more of the assemblies of the delivery apparatus. The touch pad or touch screen may include tactile, light, or audible feedback for assisting the user.

Figure 16:
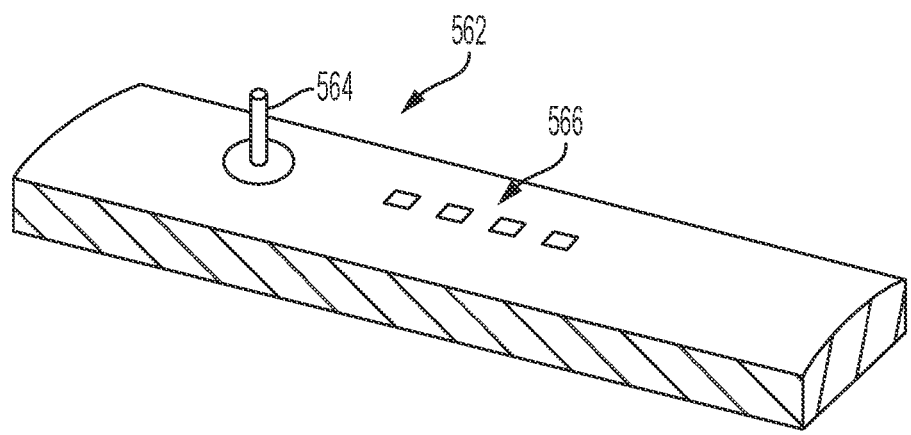
FIG. 16 illustrates a partial cross section view of an embodiment of a portion of a handle.

FIG. 16, for example, illustrates a cross sectional portion of a part of the handle 14 in which a control device 562 comprises a joystick 564 and one or more buttons 566. The joystick 564 may be configured for the user to provide directional control for the delivery apparatus via the rail assembly 20. The one or more buttons 566 may be configured for the user to provide other controls to the delivery apparatus, including depth control, deployment of the implant 70, or movement of one or more of the assemblies of the delivery apparatus.

Through use of a device such as a touch pad 558 or a joystick 564 to control the rail assembly 20, the user may be able to move the rail assembly 20 in combinations of directions simultaneously. This is an improvement over prior methods, which primarily use mechanical knobs or the like, wherein the user is only able to move the rail assembly 20 in a single plane at a single time. With the use of a motor 500 to actuate the rail assembly 20, the rail assembly 20 may move in multiple planes simultaneously. The simultaneous control may be provided by a corresponding signal from the control device to the motor 500. In one embodiment, the simultaneous control may be provided by the processor 536 to the motor 500. For example, a user (e.g., a clinician) may provide an input for a particular direction of movement via the joystick 564 that is sent to the processor 536. The processor 536 may process the input to control the motor 500 to move the elongate shaft 12 in that direction. The processor 536 may control the motor 500 to move in various directions, for example the motor 500 may move the pull wires 138, 140 simultaneously or in sequence to produce movement in a variety of directions. The processor 536 may be configured to operate the motor 500 to deflect the elongate shaft 12 in at least two planes, among a variety of other directions. The control device used to provide an input to the processor 536 or motor 500 may include buttons, joysticks, touchpads, touch screens, knobs, or motion sensing devices, among other forms of input. An example of a motion sensing device is shown in FIGS. 37 and 38, in which the control device 588 may be configured to sense motion (e.g., tilt or spatial displacement) of the control device 588 to provide an input to the processor 536 or motor 500.

Referring again to FIG. 15, the system 10 may include an output device that may have various forms. The output device may be configured to provide an output to a user that may indicate a condition of the delivery apparatus or of the patient. The output device may be configured to provide an indicator of a condition of the delivery apparatus or of the patient. For example, as shown in FIG. 15, an output device may include lights 568 that may illuminate to indicate a condition of the delivery apparatus or of the patient. The lights 568 may illuminate to indicate the delivery apparatus has contacted or approached a surface of the patient's body (a condition of the delivery apparatus), or may illuminate to indicate a certain condition of the patient's body, such as a correct or incorrect pressure being sensed in the patient's body. Other forms of output devices may be utilized, including a haptic device 570, such as a vibrating actuator, which may indicate the condition of the delivery apparatus or of the patient. An output device may include the display screen of the touch screen 560 shown in FIG. 15. An output device may include a display screen 584 as shown in FIG. 37. An output device may include one or more of a display screen, a light, a speaker, or a haptic device, among other forms of output devices. Various forms of output devices may be utilized as desired. An indicator produced on the output device may include one or more of an image, data, a sound, a light, or a haptic signal. The output device may be configured to provide an indicator based on an output provided by the processor 536.

Figure 17:
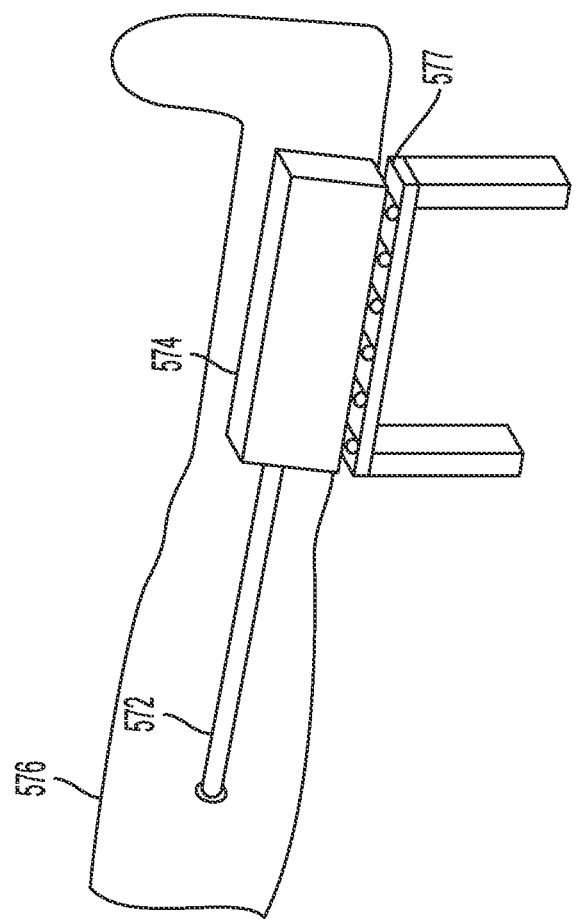
FIG. 17 illustrates a side perspective view of insertion of a delivery apparatus into a patient's body.

The actuation of the delivery apparatus may include deflection of a portion of the delivery apparatus and performing an operation of the delivery apparatus. The actuation of the delivery apparatus by at least one motor may include a translation of the elongate shaft 12 and may include a translation of a housing at a proximal end of the elongate shaft 12. Axial translation of the delivery apparatus may be provided. FIG. 17, for example, illustrates a side perspective view of a delivery apparatus including an elongate shaft 572 and a housing 574. The delivery apparatus is being passed transfemorally into a patient's body 576. The elongate shaft 572 may be configured similarly as the elongate shaft 12. The housing 574 may be configured similarly as the housing forming the handle 14, however the housing 574 may not comprise a handle for grip by a user. Rather the housing 574 may include a motor or may be configured to move along a motor driven rail 577 or other assembly that actuates axial movement of the delivery apparatus into the patient's body. The axial movement of the delivery apparatus may be controlled by a control device, which may be positioned proximate the housing 574 or may be located remote from the housing 574. The control device may be configured to perform other control of the delivery apparatus, including deflection of a portion of the delivery apparatus and performing a process of the delivery apparatus, as discussed herein. In this manner, a user need not hold the housing 574 and may proceed with the implant delivery procedure without contacting the delivery apparatus or without being present for the implant delivery procedure. A processor 536 may provide the control of the motor of the motor driven rail 577 and any other motor used to actuate the delivery apparatus, as discussed herein.

Figure 18:
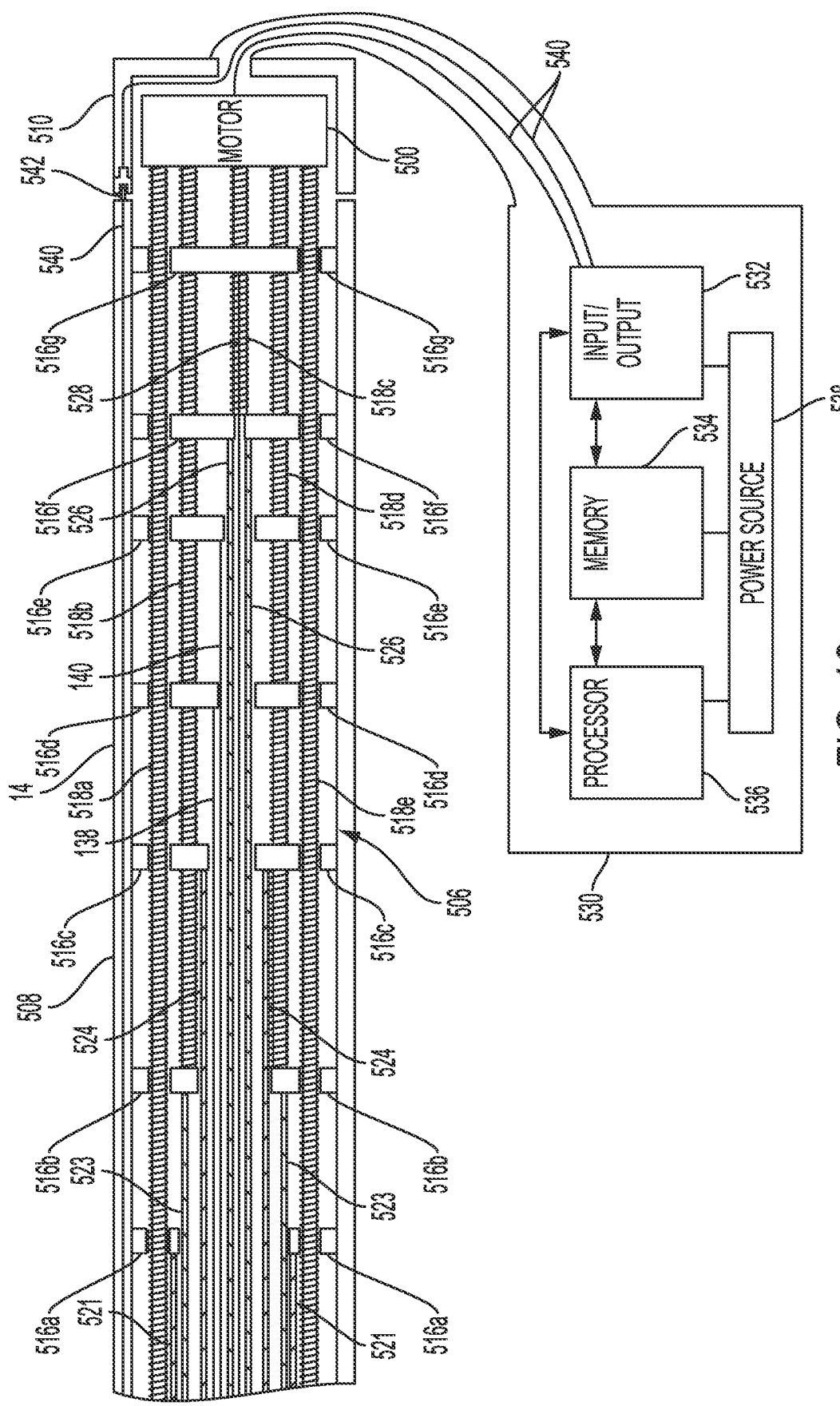
FIG. 18 illustrates a cross section view of the delivery system handle and controller shown in FIG. 10.

The motor 500 may be configured to actuate the delivery apparatus by selectively moving one or more of the outer sheath assembly 22, the mid shaft assembly 21, the inner assembly 18, the rail assembly 20, the assembly including the distal pull wires 138, the assembly including the proximal pull wires 140, and the nose cone assembly 31. As discussed with respect to FIG. 10, the motor 500 may be configured to selectively move such components based on the configuration of the actuation mechanism 506. As an example of the selective actuation of the motor 500, an example of depth control is provided. The depth of the elongate shaft 12 of the delivery apparatus may be set by moving the outer sheath assembly 22, the mid shaft assembly 21, the inner assembly 18, and the nose cone assembly 31, relative to the rail assembly 20. Such a movement allows the outer sheath assembly 22, the mid shaft assembly 21, the inner assembly 18, and the nose cone assembly 31 to slide relative to the rail assembly 20, which may be deflected at an angle. The deflection of the rail assembly 20 allows the outer sheath assembly 22, the mid shaft assembly 21, the inner assembly 18, and the nose cone assembly 31 to slide along the rail assembly 20 at this angle and accordingly have depth in a direction towards a mitral or tricuspid annulus or the like, including another annulus or body location. As such, the relative movement of the outer sheath assembly 22, the mid shaft assembly 21, the inner assembly 18, and the nose cone assembly 31 to the rail assembly 20 produces the depth. As shown in FIG. 18, the motor 500 may be configured to actuate such depth by simultaneously actuating drive rods 518c, 518d, and 518e to move adaptors 516c, 516d, and 516e. The adaptors 516c, 516d, and 516e may move proximally, thus causing the rail assembly 20 and pull wires 138, 140 to move proximally as well relative to the outer sheath assembly 22, the mid shaft assembly 21, the inner assembly 18, and the nose cone assembly 31 to thus result in depth of the elongate shaft 12. The motor 500 may thus be configured to simultaneously actuate various portions of the elongate shaft 12 to produce a desired result. The motor 500 may move the assemblies including the pull wires 138, 140 with the rail assembly 20 to maintain tension in the pull wires 138, 140. Although shown as an operation to produce depth, the motor 500 may be configured to produce other combinations of movement. For example, as discussed previously, a deflection of the rail assembly 20 in multiple planes may be provided. The motor 500 may be configured to actuate both the distal pull wire 138 and the proximal pull wire 140 simultaneously or in a sequence to produce the desired movement of the rail assembly 20.

The motor 500 accordingly may be configured to move one of the assemblies (outer sheath assembly 22, the mid shaft assembly 21, the inner assembly 18, the rail assembly 20, the assembly including the distal pull wires 138, the assembly including the proximal pull wires 140, and the nose cone assembly 31), each extending along a length of the elongate shaft, relative to another one of the assemblies. The assembly may be moved relative to another assembly that is positioned within a lumen of the assembly (e.g., the rail assembly 20 may be positioned within a lumen of the outer sheath assembly 22). Various assemblies may be moved simultaneously (e.g., rail assembly 20 may be moved simultaneously with the assembly including the distal pull wires 138, and the assembly including the distal pull wires 138 may be moved simultaneously with the assembly including the proximal pull wires 140). The processor 536 may be configured to control the motor 500 to provide the movements disclosed herein.

Figure 19:
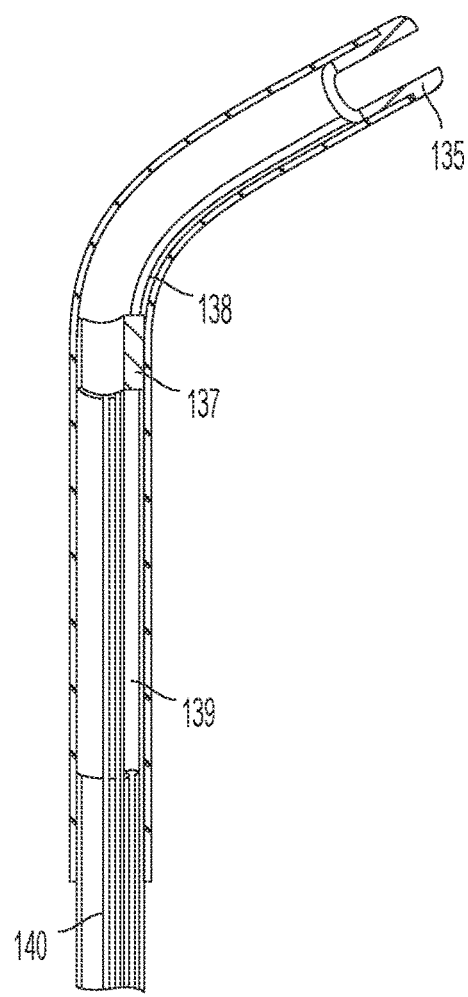
FIG. 19 illustrates a cross section view of a rail assembly.
Figure 20:
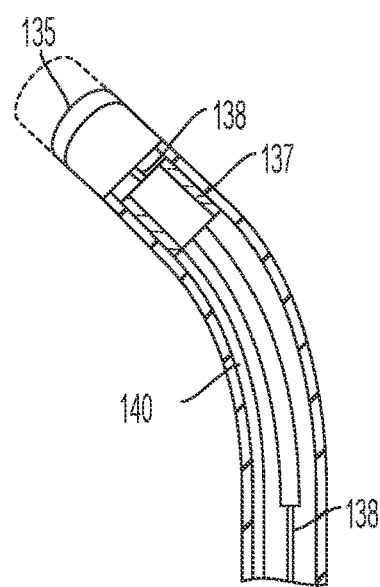
FIG. 20 illustrates a cross section view of a rail assembly viewed at an angle of ninety degrees from the view shown in FIG. 19.

In one embodiment, the motor 500 may be configured to compensate for movement of a portion of the elongate shaft 12 based on movement of another portion of the elongate shaft 12. For example, as portions of the elongate shaft 12 are moved, the position of another portion of the elongate shaft 12 may be undesirably moved as well. The motor 500 may be configured to compensate for the undesired movement. FIG. 19, for example, illustrates a side cross sectional view of a portion of the rail assembly 20. The distal pull wire 138 has been pulled proximally, causing a distal portion of the rail assembly 20 to deflect in a direction as shown in FIG. 19. Upon the proximal pull wire 140 then being pulled to deflect a proximal portion of the rail assembly 20, the distal pull wire 138 may be consequently pulled due to the deflection of the proximal portion of the rail assembly 20. FIG. 20, for example, shows a side cross sectional view of the rail assembly 20 viewed at a ninety-degree angle from shown in FIG. 19 (rotated about the axial dimension of the rail assembly 20). The deflected distal portion of the rail apparatus 20 is facing into the page in FIG. 20. Upon the proximal pull wire 140 being pulled to deflect the proximal portion of the rail apparatus 20, the distal portion of the rail apparatus 20 has consequently deflected as represented in dashed lines in FIG. 20. Under prior methods using mechanical knobs or the like to control the rail apparatus 20, the shortening of the distal end of the rail apparatus 20 would be corrected by operating multiple mechanical knobs move the distal pull wire 138. Here, however, the motor 500 may be configured to automatically compensate for movement of one or more of the pull wires 138, 140 to reduce the shortening of the distal portion of the rail assembly 20. In embodiments, the motor 500 may be configured to compensate for shortening or elongation of any portion of the elongate shaft 12, including portions of the outer sheath assembly 22, the mid shaft assembly 21, the inner assembly 18, and the nose cone assembly 31. For example, the motor 500 may be configured to translate a portion of the elongate shaft 12 other than the rail assembly 20 to compensate for deflection of the rail assembly 20.

The motor 500 may be configured to perform the operations discussed with respect to FIGS. 18-20 based on the input from the control device (for example control device 504) or based on the wiring of the motor 500 or a combination of both. For example, if the control device 504 is utilized to request simultaneous movement of two assemblies of the elongate shaft 12, then a signal may be provided to the motor 500 to operate the respective drive rods corresponding to those assemblies. If the control device 504 is utilized to request movement of portion of the elongate shaft 12 that requires compensation, then the motor 500 may be wired to automatically perform such compensation. For example, the motor 500 may be wired to compensate for movement of certain assemblies based on movements of other assemblies.

In certain embodiments, the processor 536 may be utilized to automatically move the assemblies or other portions of the elongate shaft 12 to perform the operations discussed with regards to FIGS. 18-20. For example, if a request is made to increase the depth of the elongate shaft 12 or deploy the implant 70, then the processor 536 may be configured to operate a program (which may be stored in memory 534) to control the motor 500 to move the corresponding assemblies or other portions of the elongate shaft 12. If a request is made that requires compensation, then the processor 536 may be configured to operate a program (which may be stored in memory 534) to control the motor 500 to move the corresponding assemblies or other portions of the elongate shaft 12 to automatically perform such compensation. The processor 536 may be configured to operate the motor to move one of the assemblies to compensate for a motion of another of the assemblies. Particular movements and combinations of movements of the assemblies or other portion of the elongate shaft 12 may be programmed into the memory 534 and operated by the processor 536. As discussed above, the programmed movements may be based on data "learned" from previous procedures such as, for example, learned from previous procedures performed on patients with similar anatomies and/or other characteristics. The movements may be based on a machine learning algorithm utilizing data from past implantation procedures or from characteristics of the patient. Therefore, procedural steps performed successfully on patients with similar anatomies could be duplicated, thereby increasing the probability of a successful procedure on the current patient. The processor 536 may be configured to automatically operate the motor 500 to actuate a portion of the delivery apparatus in a desired manner.

The system 10 may include sensors that are configured to sense a condition of the delivery apparatus and may include sensors that are configured to sense a condition of the patient.

In certain embodiments, a sensor may be utilized to sense a condition of the delivery apparatus. The sensor may comprise a position sensor that may be utilized to determine the movement and/or position of one or more of the assemblies. For example, the position sensor may be configured to sense the amount that the motor 500 has moved the assembly to track the position and movement of the assembly. The motor 500 may be wired to track movement of the various assemblies and perform a desired movement (e.g., simultaneous movement of assemblies, or compensatory movement of one or more assemblies) based on the signal from the position sensor. In one embodiment, the signal from the position sensor may be provided to the processor 536 for the processor 536 to perform a desired movement. The signal from the position sensor may be a feedback signal to the processor 536. For example, the position sensor may sense that a portion of the elongate shaft 12 is moving in response to movement of another portion of the elongate shaft 12, and the processor 536 may operate the motor 500 to produce compensatory movement based on this signal. An indicator indicating a position of the delivery apparatus may be provided on an output device, as discussed herein. The indicator may be provided based on the position sensed by the position sensor.

A sensor may be utilized to sense a condition of the delivery apparatus in the form of a motor torque sensor. The sensor may be utilized to determine the amount of torque exerted by the motor 500. The motor torque sensor, for example, may be a current draw sensor able to sense the amount of current drawn by the motor 500. If the amount of torque exceeds a certain amount, the motor 500 may be configured to automatically shut off or reverse its operation or reduce torque. In one embodiment, the signal from the motor torque sensor may be provided to the processor 536 for the processor 536 to perform a desired movement. The signal from the motor torque sensor may be a feedback signal to the processor 536. For example, the processor 536 may operate the motor 500 to automatically shut off or reverse its operation or reduce torque based on this signal. An indicator indicating a torque of a motor of the delivery apparatus may be provided on an output device, as discussed herein. The indicator may be provided based on the torque sensed by the motor torque sensor.

Figure 21:
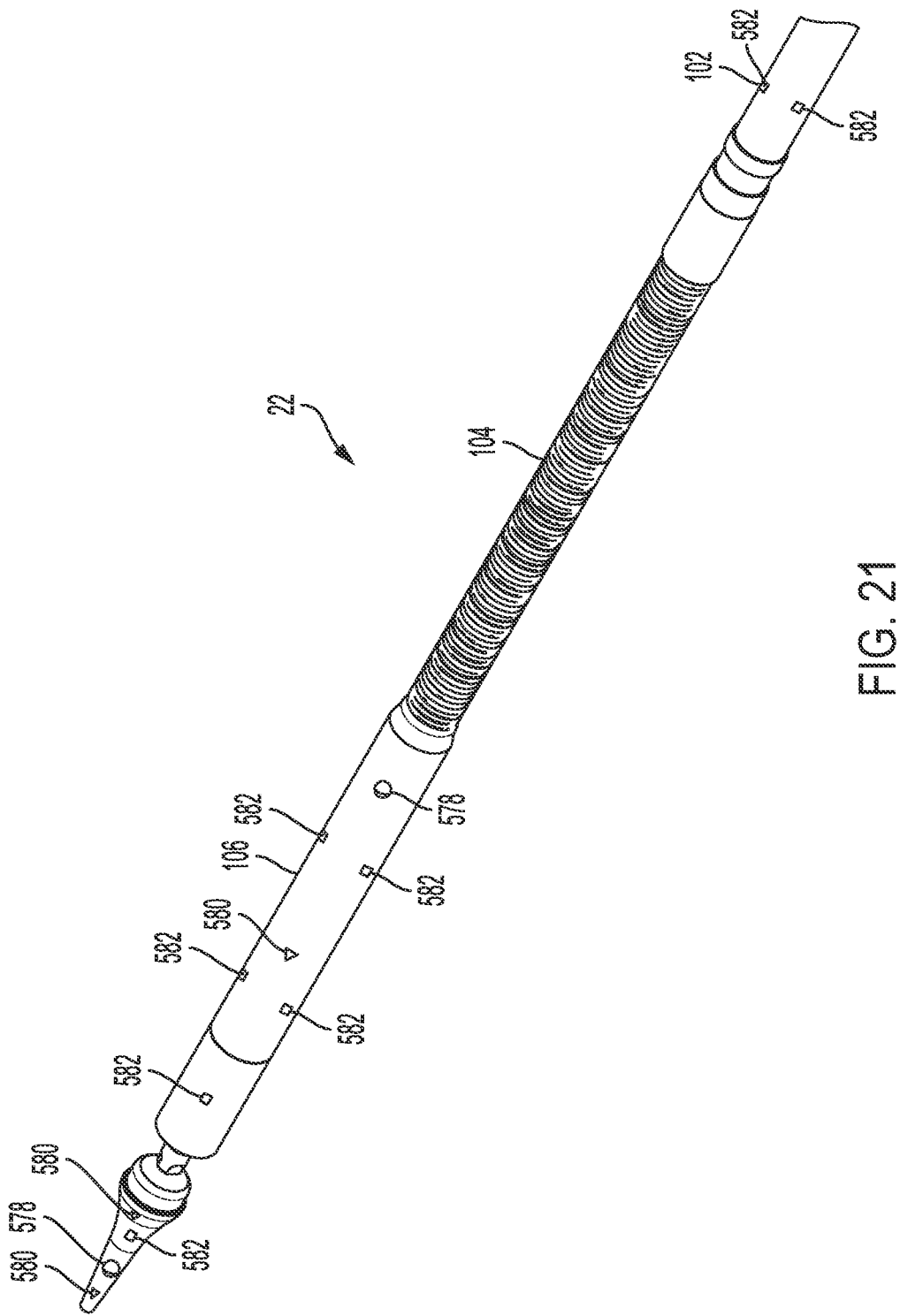
FIG. 21 illustrates a perspective view of an embodiment of a distal end of an elongate sheath.

Referring to FIG. 21, sensors configured to sense a condition of the patient may be utilized. Such sensors may be positioned as desired on the delivery apparatus. Sensors configured to sense a condition of the patient may include ambient pressure sensors 578. Such pressure sensors 578 may be configured to sense a pressure, such as a fluid pressure, within the patient's body. The pressure sensors 578 may be utilized during and following delivery of the implant 70, to determine whether the deployed implant 70 is operating as desired following implantation, or to generally monitor a condition of the patient before and following implantation. In the embodiment shown in FIG. 21, a pressure sensor 578 may be positioned on the nose cone 28 and a pressure sensor may be positioned on the capsule 106 among other locations. With this particular configuration of pressure sensors 578, one pressure sensor may be positioned in the left ventricle during implantation of the implant 70, and one pressure sensor may be positioned in the left atrium during implantation. Thus, following implantation, the pressure gradient across the mitral valve can be determined. A signal from the pressure sensors 578 may be provided to an output device (such as output devices 568, 570, or other output device) for indication to the user. In one embodiment, the pressure sensed by the pressure sensors 578 may be utilized as feedback to the system 10, such as the processor 536, to actuate the delivery apparatus. For example, if an incorrect pressure is read, the processor 536 may actuate the delivery apparatus to redeploy the implant or perform another operation. In other embodiments, other positions of pressure sensors 578 and other pressure readings may be provided.

In one embodiment, a sensor configured to sense a condition of the delivery apparatus may include sensors configured to sense a spatial relationship between the delivery apparatus and a surface of the patient's body. Such a sensor may be positioned on the delivery apparatus. Such a sensor may include a contact sensor 580. A contact sensor 580 may comprise a force transducer or load cell, or other form of contact sensor 580 that is configured to sense a force applied to the delivery apparatus. As shown, a contact sensor 580 may be positioned in a variety of positions on the elongate shaft 12, including on the nose cone 28 or other locations (such as generally on the outer surface of the elongate shaft 12). A contact sensor 580 may be configured to provide a signal when the elongate shaft 12 contacts a portion of the patient's body. Such a signal may indicate the possibility of damage to the patient's body due to the elongate shaft 12. A signal from a contact sensor 580 may be provided to an output device (such as output devices 568, 570, or other output device) for indication to the user. In one embodiment, the contact sensed by the contact sensor 580 may be utilized as feedback to the system 10, such as the processor 536, to actuate the delivery apparatus. For example, if contact is sensed with a surface, then the processor 536 may actuate the delivery apparatus to move away from the surface or stop operation of the motor 500. In other embodiments, other positions of contact sensors 580 and other contact sensors may be provided.

In one embodiment, a sensor configured to sense a condition of the delivery apparatus may include a proximity sensor 582. The proximity sensor 582 may be configured to sense a spatial relationship between the delivery apparatus and a surface of the patient's body. Such a sensor may be positioned on the delivery apparatus. A proximity sensor 582 may comprise a device for sensing a distance to a portion of the patient's body, including use of ultrasound, or echo signals, or visual identification. As shown, a proximity sensor 582 may be positioned in a variety of positions on the elongate shaft 12, including on the nose cone 28 or other locations (such as generally on the outer surface of the elongate shaft 12). The proximity sensor 582 may be configured to provide a signal when the elongate shaft 12 approaches a portion of the patient's body and may provide such a signal to an output device (such as output devices 568, 570, or other output device) for indication to the user. In one embodiment, the proximity sensed by the proximity sensor 582 may be utilized as feedback to the system 10, such as the processor 536, to actuate the delivery apparatus. For example, if proximity to a surface (e.g., an inner wall of blood vessel) is sensed, the processor 536 may actuate the delivery apparatus to move away from the surface or stop operation of the motor 500. As such, the delivery system could be advanced through the patient's vasculature without damaging an inner wall of a blood vessel. This "smart catheter" technology could provide a significant improvement over current "blind catheters." For example, this technology could reduce or eliminate the possibility of vascular dissection, which is a significant and life-threatening risk with current delivery systems. Although embodiments have been described for sake of explanation, it will be understood that other positions of proximity sensors 582 and other proximity readings may be provided.

Figure 22:
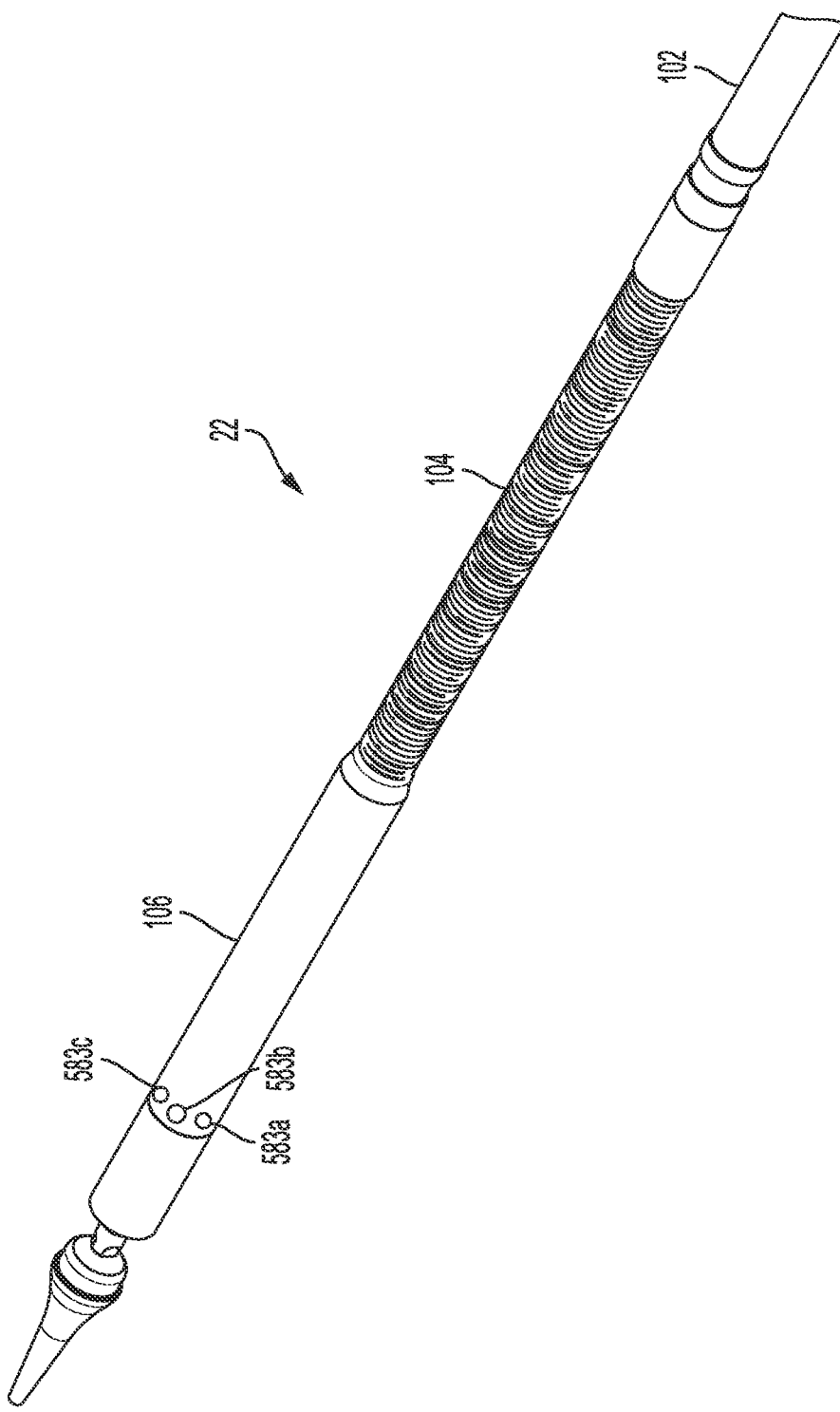
FIG. 22 illustrates a perspective view of an embodiment of a distal end of an elongate sheath.
Figure 23:
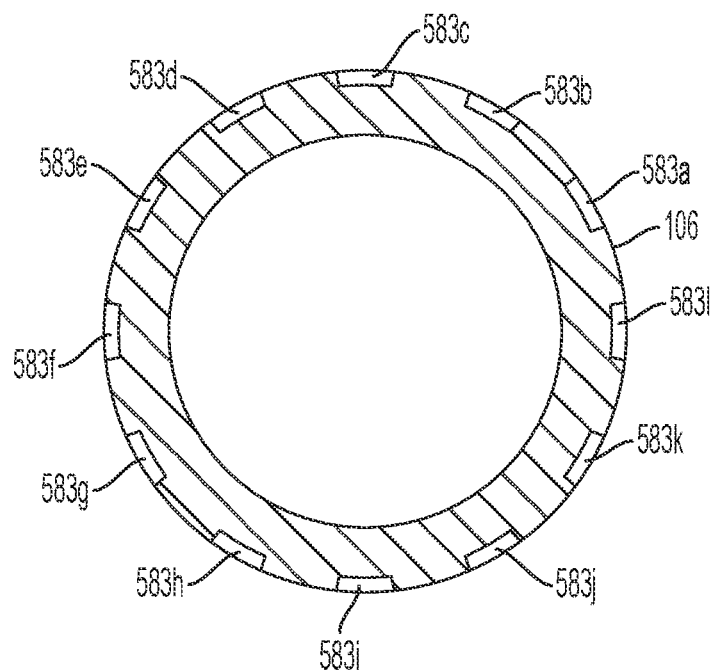
FIG. 23 illustrates a cross sectional view of a capsule of the elongate sheath shown in FIG. 22.
Figure 24:
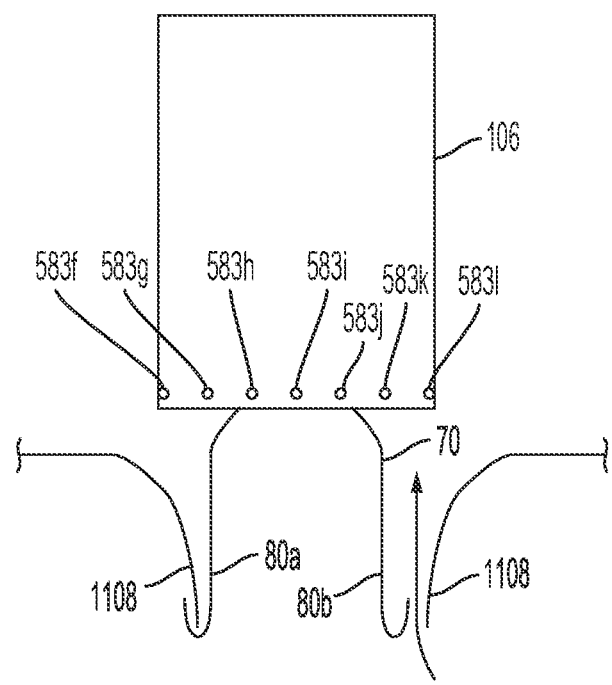
FIG. 24 illustrates a side schematic view of the elongate sheath shown in FIG. 22 deploying an implant to a mitral heart valve.

FIGS. 22-24 illustrate an embodiment of a sensor configured to sense a condition of the patient. The sensor comprises a flow sensor that may sense a fluid flow (e.g., blood flow) within the patient's body. A plurality of sensors 583a-1 (as marked in FIG. 23) may be positioned on the delivery apparatus forming a spaced array of sensors 583a-1. The sensors 583a-1 may be configured to sense a local fluid flow, such that the sensors 583a-1 may sense a fluid flow in a local area in the body that is different from the fluid flow sensed by other sensors 583a-1. FIG. 22 illustrates a perspective view of the distal end of the elongate shaft 12, with sensors 583a-c visible on the capsule 106. FIG. 23 illustrates a cross sectional view of the capsule 106 showing the spaced array of sensors 583a-1. The sensors 583a-1 may be positioned on the delivery apparatus to sense fluid flow at a location proximate the deployment location for the implant 70. Such a location may comprise the capsule 106 or another portion of the delivery apparatus.

FIG. 24 illustrates an exemplary operation of the sensors 583a-1. The implant 70 may be deployed in a native mitral or tricuspid valve, with one distal anchor 80a capturing a leaflet 1108 and another distal anchor 80b failing to capture a leaflet 1108. The sensors 583k, 583l may sense a flow of blood by the mis-captured leaflet 1108 and may provide a signal accordingly. The sensors 583a-1 may be configured to sense a differential flow between the sensors 583f, 583g proximate the captured leaflet 1108 and the sensors 583k, 583l proximate the mis-captured leaflet 1108. The flow sensors 583a-1 may be configured to provide a signal when a flow is sensed and may provide such a signal to an output device (such as output devices 568, 570, or other output device) for indication to the user. In one embodiment, the flow sensed by the flow sensors 583a-1 may be utilized as feedback to the system 10, such as the processor 536, to actuate the delivery apparatus. For example, if flow is sensed indicated a mis-capture of a leaflet, then the processor 536 may actuate the delivery apparatus to redeploy the implant 70 or perform another operation. In other embodiments, other positions of flow sensors 583a-1 and other flow readings may be provided.

The sensors that are configured to sense the condition of the delivery apparatus and the sensors that are configured to sense a condition of the patient may be coupled to the delivery apparatus. In certain embodiments, however, the sensors that are configured to sense the condition of the delivery apparatus and the sensors that are configured to sense a condition of the patient may not be coupled to the delivery apparatus and may be external to the patient's body.

The signals from the sensors that are configured to sense the condition of the delivery apparatus and the sensors that are configured to sense a condition of the patient, may be utilized in a variety of manners. In one embodiment, the signals may be provided as indicators on an output device (such as output devices 568, 570, or other output device) for indication to the user. For example, a condition of the delivery apparatus may be indicated to a user in a variety of forms, for example, an output device may include one or more of a display screen, a light, a speaker, or a haptic device, among other forms of output devices. An indicator produced on the output device may include one or more of an image, data, a sound, a light, or a haptic signal. The user may be able to act accordingly based on the indicator. For example, if an indicator indicates that the delivery apparatus has contacted a portion of the patient's body, then the user may act accordingly to move the delivery apparatus away from the body. A condition of the patient's body may similarly be indicated to a user in a variety of forms.

In embodiments, the signals from the sensors that are configured to sense the condition of the delivery apparatus and the sensors that are configured to sense a condition of the patient may be provided to the processor 536. The processor 536 may provide a variety of outputs based on the one or more of a condition of the patient's body or a condition of the delivery apparatus sensed by the one or more sensors. One such form of output includes a log of data for an implantation procedure with the delivery apparatus.

Such a log of data may be stored in the memory 534. The data may be stored for later retrieval by a user for analysis or may record a log of actions taken by the delivery apparatus. For example, the position sensor signals may be logged to record the movements of the delivery apparatus, among other forms of sensors signals.

The processor 536 may provide an output to an output device based on the condition of the patient's body or a condition of the delivery apparatus sensed by the one or more sensors. The output may result in an indicator on an output device (such as output devices 568, 570, or other output device) for indication to the user. For example, a condition of the delivery apparatus may be indicated to a user in a variety of forms, for example, an output device may include one or more of a display screen, a light, a speaker, or a haptic device, among other forms of output devices. The processor 536 may process the signals to produce a desired indicator to a user. For example, the sensors 583a-1 may sense a flow of blood during deployment of the implant 70, and the processor 536 may process these signals to provide an indicator to a user that leaflet mis-capture has occurred.

The processor 536 may provide an output that comprises a control of the motor 500 based on the condition of the patient's body or a condition of the delivery apparatus sensed by the one or more sensors. The processor 536 may be configured to operate the motor 500 to actuate the delivery apparatus based on a signal from the sensors. The signal from the sensors may comprise feedback signals that are input to the processor 536 for the processor to control operation of the motor 500. For example, a signal from a contact sensor 580 or a proximity sensor 582 may be provided to the processor 536 as feedback that the delivery apparatus has contacted or is proximate a surface of the patient's body. The processor 536 accordingly may provide an output that operates the motor 500 to avoid or retract from the surface of the patient's body. A signal from the flow sensors 583a-1 may cause the processor 536 to provide an output to the motor 500 to redeploy the implant 70 or move the portion of the delivery apparatus to recapture the leaflet 1108. A signal from a position sensor may provide feedback to the processor 536 regarding whether the delivery apparatus is performing the correct movements, and the processor 536 may operate the motor 500 to perform corrective movements if desired (e.g., deflect the elongate shaft 12 if needed). The processor 536 may be programmed to automatically respond and produce outputs based on the condition of the patient's body or a condition of the delivery apparatus sensed by the one or more sensors. The programming for the processor 536 may be stored in the memory 534 and operated by the processor 536.

A method of utilizing the system 10 for delivering an implant 70 is represented in FIGS. 25-30. The method may utilize any of the systems or devices disclosed herein. The delivery system 10 can be used in a method for percutaneous delivery of a replacement mitral valve to treat patients with moderate to severe mitral regurgitation. However, it will be understood that the delivery systems described herein can be used as part of other methods as well, such as implants for repair of valves and delivery of implants to other heart valves and delivery of other implants.

Figure 25:
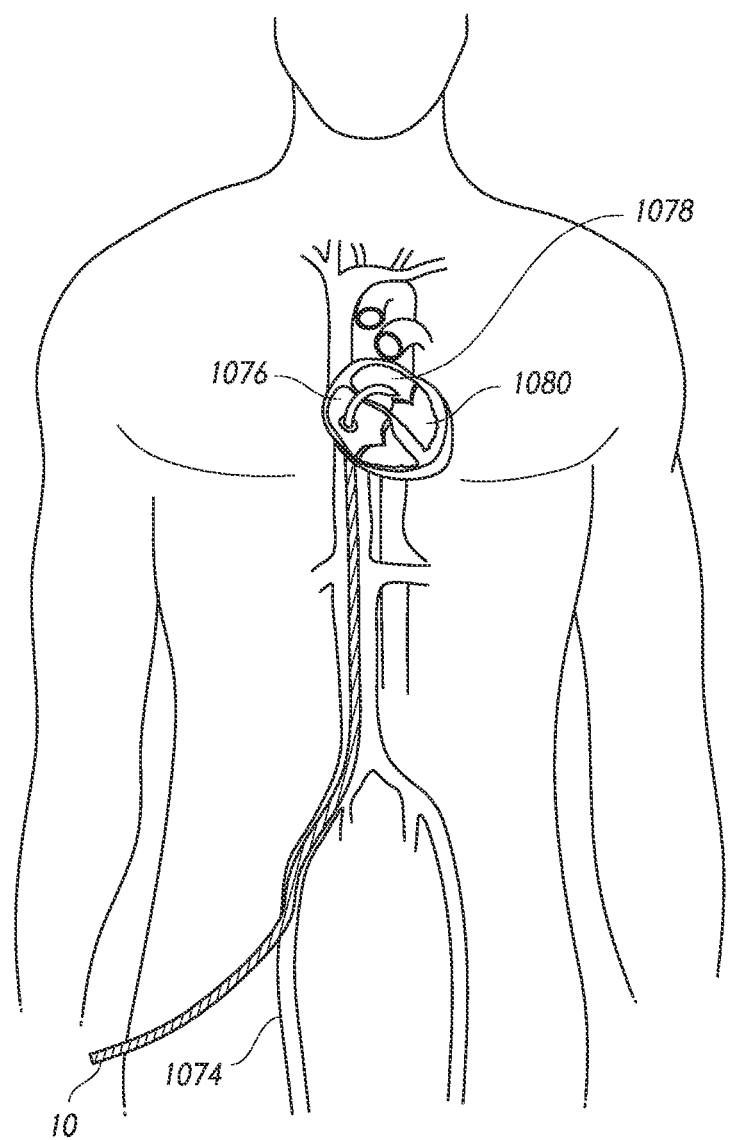
FIG. 25 illustrates a schematic view of a delivery system entering a patient's body.

As shown in FIG. 25, in one embodiment the method may include extending a delivery apparatus within a portion of the patient's body to deliver an implant to a body location. The delivery system 10 can be placed in the ipsilateral femoral vein 1074 and advanced toward the right atrium 1076. A transseptal puncture using known techniques can then be performed to obtain access to the left atrium 1078.

The delivery system 10 can then be advanced in to the left atrium 1078 and then to the left ventricle 1080 passing through the atrial septum. FIG. 25 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may be used.

Accordingly, it can be advantageous for a user to be able to steer the delivery system 10 through the complex areas of the heart in order to position a replacement mitral valve in line with the native mitral valve. This task can be performed with or without the use of a guide wire with the above disclosed system. The distal end of the delivery system can be advanced into the left atrium 1078. The motor 500 may then be operated to actuate the rail assembly 20 to target the distal end of the delivery system 10 to the appropriate area. The motor 500 may be operated by a processor 536 as discussed herein. A user can then continue to pass the bent delivery system 10 through the transseptal puncture and into the left atrium 1078. The motor 500 may then be operated to create an even greater bend in the rail assembly 20. In the fully bent configuration, a user can then place the replacement mitral valve in the proper location.

The rail assembly 20 can be particularly advantageous for entering into the native mitral valve. As discussed above, the rail assembly 20 can form two bends, both of which can be located in the left atrium 1078. The bends in the rail assembly 20 can position the implant 70, located in the implant retention area 16, so that it is coaxial with the native mitral valve. Once the implant 70 is coaxial, the outer sheath assembly 22, mid shaft assembly 21, inner assembly 18, and nose cone assembly 31 can together be advanced (e.g., using the motor 500) distally relative to the rail assembly 20. These assemblies advance straight off of the rail assembly 20, thus advancing them coaxial with the native mitral valve until the implant 70 is to be released while maintaining the implant 70 in the compressed configuration, as discussed below. Thus, the rail assembly 20 provides the ability for a user to lock the angular position in place, so that the user then has to just longitudinally advance the other assemblies over the rail assembly 20 while not needed to make any angular changes, greatly simplifying the procedure. The rail assembly 20 acts as an independent steering assembly, where all the assembly does is provide steerability and no further implant release functionality. Further, the construction of the rail assembly 20 as described above is sufficiently rigid so that when the rail assembly is actuated to its bent shape, movement of the other components, e.g., the outer sheath assembly 22, mid shaft assembly 21, inner assembly 18, and/or nose cone assembly 31, the rail assembly 20 maintains its shape. Thus, the rail assembly 20 can remain in the desired bent position during the sliding of the other assemblies relative to the rail assembly 20, and the rail assembly 20 can help direct the other assemblies to the final position. The proximal/distal translation of the other assemblies over the rail assembly 20 allows for ventricular-atrial motion. In addition, once the distal anchors 80 of the implant 70 have been released in the left ventricle 1080, but prior to full release, the other assemblies can be proximally retracted over the rail assembly 20 to capture any leaflets or chordae.

Figure 26:
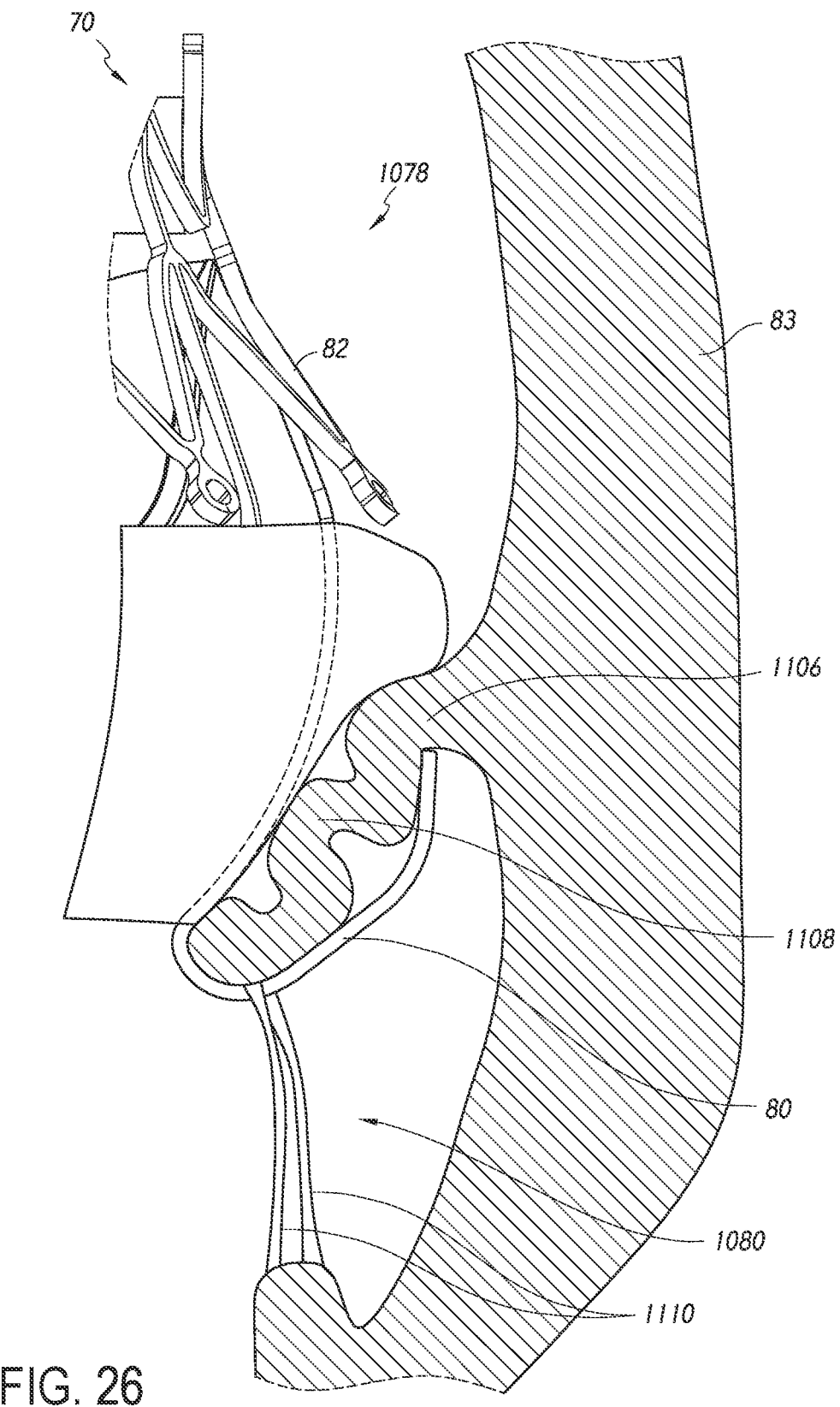
FIG. 26 illustrates a schematic view of an implant deployed to a patient's mitral valve.

Reference is now made to FIG. 26 which illustrates a schematic representation of a portion of an embodiment of a replacement heart valve (implant 70) positioned within a native mitral valve of a heart 83. A portion of the native mitral valve is shown schematically and represents typical anatomy, including a left atrium 1078 positioned above an annulus 1106 and a left ventricle 1080 positioned below the annulus 1106. The left atrium 1078 and left ventricle 1080 communicate with one another through a mitral annulus 1106. Also shown schematically in FIG. 26 is a native mitral leaflet 1108 having chordae tendineae 1110 that connect a downstream end of the mitral leaflet 1108 to the papillary muscle of the left ventricle 1080. The portion of the implant 70 disposed upstream of the annulus 1106 (toward the left atrium 1078) can be referred to as being positioned supra-annularly. The portion generally within the annulus 1106 is referred to as positioned intra-annularly. The portion downstream of the annulus 1106 is referred to as being positioned sub-annularly (toward the left ventricle 1080).

As shown in FIG. 26, the replacement heart valve (e.g., implant 70) can be positioned so that the mitral annulus 1106 is located between the distal anchors 80 and the proximal anchors 82. In some situations, the implant 70 can be positioned such that ends or tips of the distal anchors 80 contact the annulus 1106 as shown, for example, in FIG. 26. In some situations, the implant 70 can be positioned such that ends or tips of the distal anchors 80 do not contact the annulus 1106. In some situations, the implant 70 can be positioned such that the distal anchors 80 do not extend around the leaflet 1108.

As illustrated in FIG. 26, the replacement heart valve implant 70 can be positioned so that the ends or tips of the distal anchors 80 are on a ventricular side of the mitral annulus 1106 and the ends or tips of the proximal anchors 82 are on an atrial side of the mitral annulus 1106. The distal anchors 80 can be positioned such that the ends or tips of the distal anchors 80 are on a ventricular side of the native leaflets beyond a location where chordae tendineae 1110 connect to free ends of the native leaflets. The distal anchors 80 may extend between at least some of the chordae tendineae 1110 and, in some situations such as those shown in FIG. 26, can contact or engage a ventricular side of the annulus 1106. It is also contemplated that in some situations, the distal anchors 80 may not contact the annulus 1106, though the distal anchors 80 may still contact the native leaflet 1108. In some situations, the distal anchors 80 can contact tissue of the left ventricle 1080 beyond the annulus 1106 and/or a ventricular side of the leaflets.

During delivery, the distal anchors 80 (along with the frame) can be moved toward the ventricular side of the annulus 1106, such as by translating the other assemblies (e.g., outer sheath assembly 22, mid shaft assembly 21, inner assembly 18, and nose cone assembly 31) proximally with respect to the rail assembly 20, with the distal anchors 80 extending between at least some of the chordae tendineae 1110 to provide tension on the chordae tendineae 1110. The degree of tension provided on the chordae tendineae 1110 can differ. For example, little to no tension may be present in the chordae tendineae 1110 where the leaflet 1108 is shorter than or similar in size to the distal anchors 80. A greater degree of tension may be present in the chordae tendineae 1110 where the leaflet 1108 is longer than the distal anchors 80 and, as such, takes on a compacted form and is pulled proximally. An even greater degree of tension may be present in the chordae tendineae 1110 where the leaflets 1108 are even longer relative to the distal anchors 80. The leaflet 1108 can be sufficiently long such that the distal anchors 80 do not contact the annulus 1106.

Figure 27:
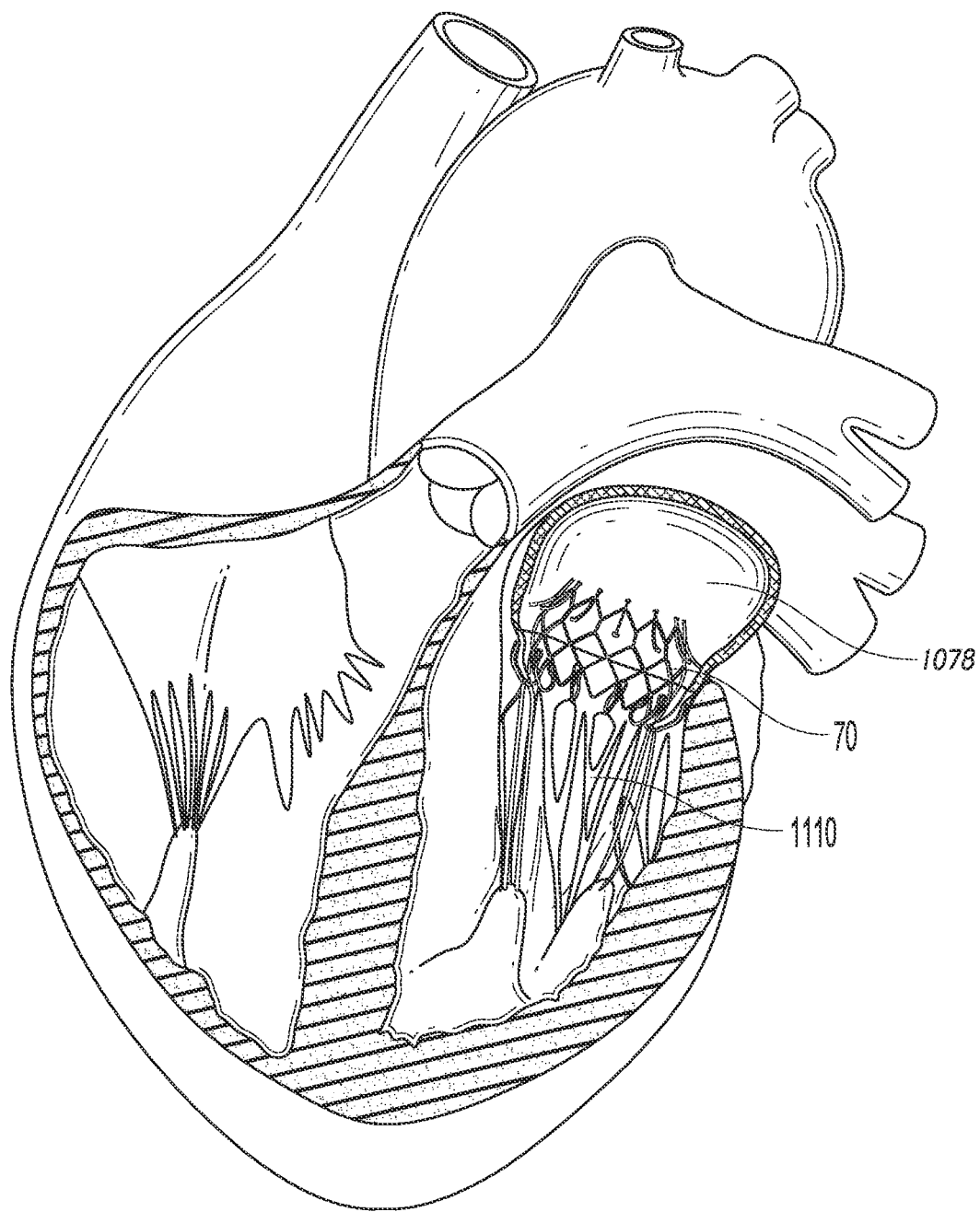
FIG. 27 illustrates a schematic view of an implant deployed to a patient's mitral valve.

The proximal anchors 82, if present, can be positioned such that the ends or tips of the proximal anchors 82 are adjacent the atrial side of the annulus 1106 and/or tissue of the left atrium 1078 beyond the annulus 1106. In some situations, some or all of the proximal anchors 82 may only occasionally contact or engage atrial side of the annulus 1106 and/or tissue of the left atrium 1078 beyond the annulus 1106. For example, as illustrated in FIG. 26, the proximal anchors 82 may be spaced from the atrial side of the annulus 1106 and/or tissue of the left atrium 1078 beyond the annulus 1106. The proximal anchors 82 could provide axial stability for the implant 70. It is also contemplated that some or all of the proximal anchors 82 may contact the atrial side of the annulus 1106 and/or tissue of the left atrium 1078 beyond the annulus 1106. FIG. 27 illustrates the implant 70 implanted in the heart. Although the illustrated replacement heart valve includes both proximal and distal anchors, it will be appreciated that proximal and distal anchors are not required in all cases. For example, a replacement heart valve with only distal anchors may be capable of securely maintaining the replacement heart valve in the annulus. This is because the largest forces on the replacement heart valve are directed toward the left atrium during systole. As such, the distal anchors are most important for anchoring the replacement heart valve in the annulus and preventing migration.

Figure 28:
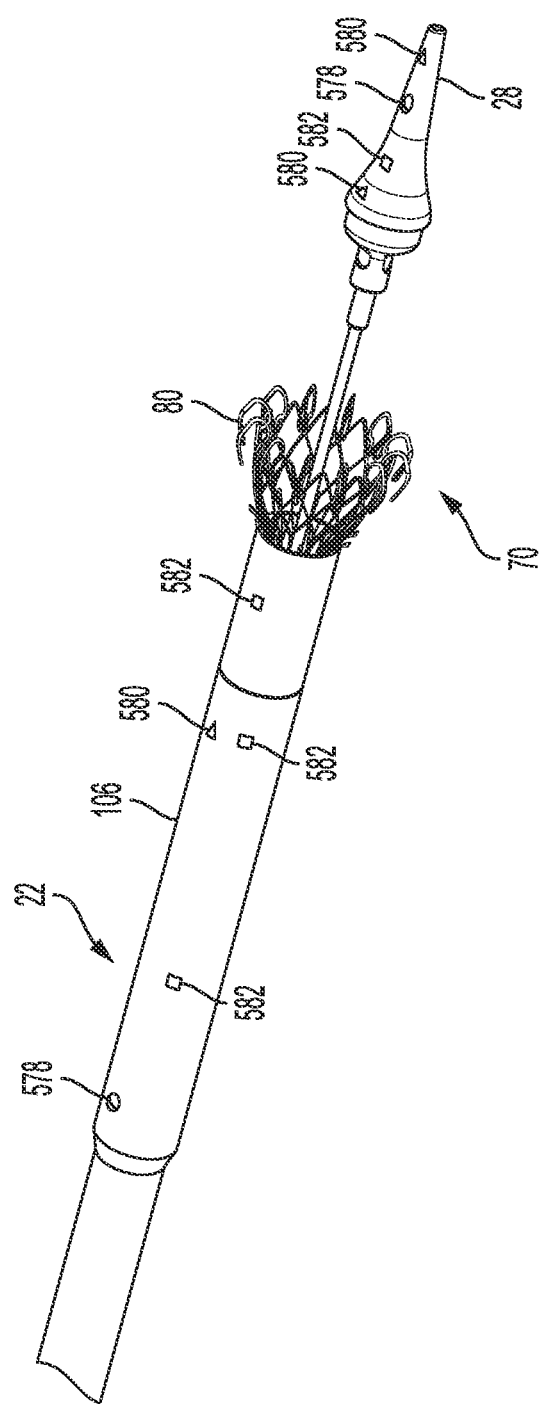
FIG. 28 illustrates a perspective view of a distal end of an elongate sheath deploying an implant.
Figure 29:
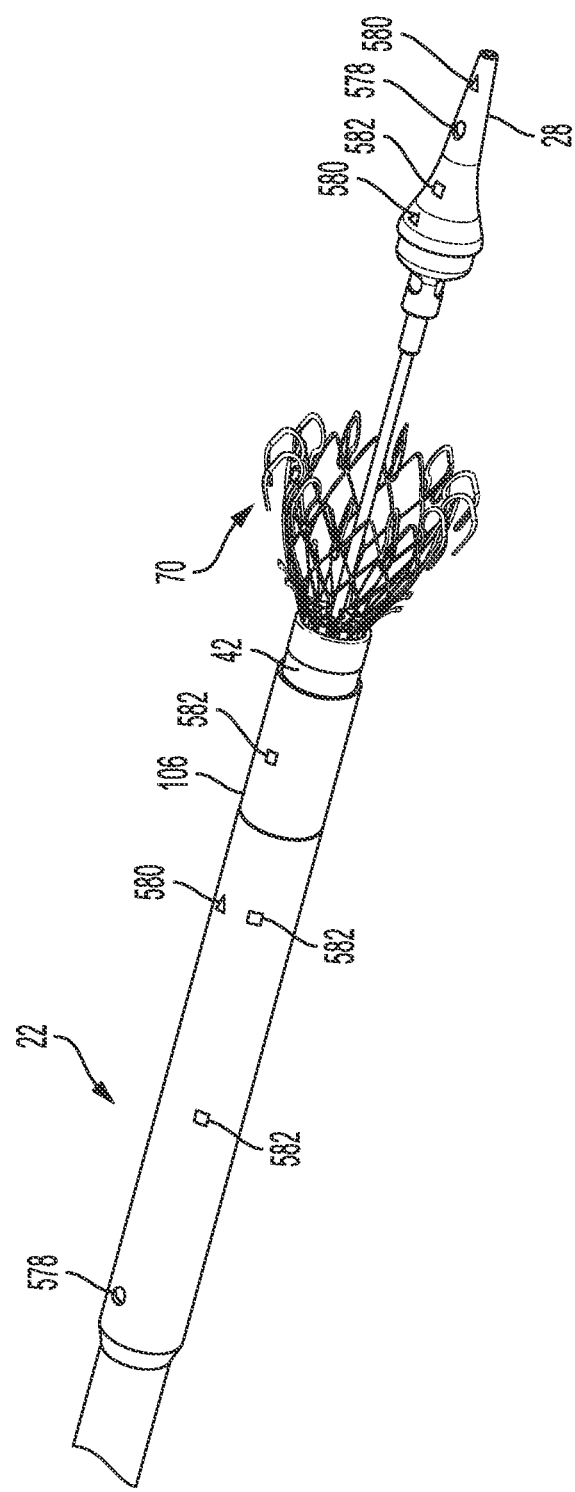
FIG. 29 illustrates a perspective view of a distal end of an elongate sheath deploying an implant.
Figure 30:
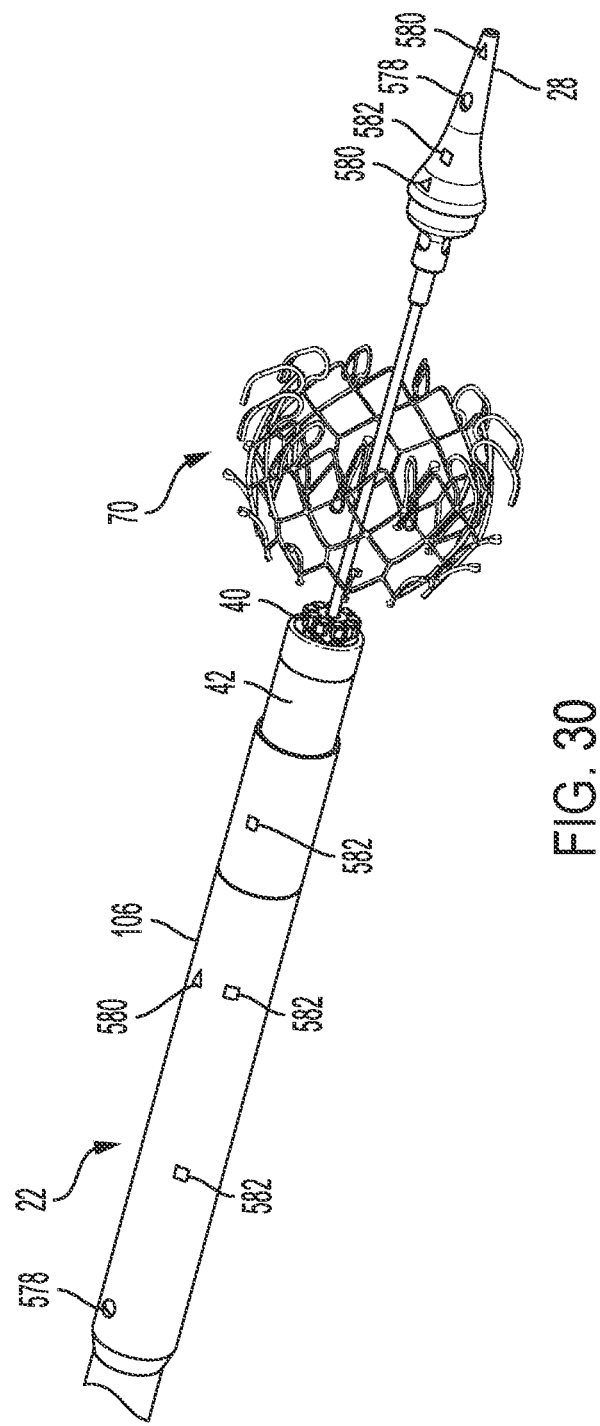
FIG. 30 illustrates a perspective view of a distal end of an elongate sheath deploying an implant.

FIGS. 28-30 illustrate the release mechanism of the delivery system 10. During the initial insertion of the implant 70 and the delivery system 10 into the body, the implant 70 can be located within the system 10, similar to as shown in FIG. 2A. The distal end 303 of the implant 70, and specifically the distal anchors 80, are restrained within the capsule 106 of the outer sheath assembly 22, thus preventing expansion of the implant 70. Similar to what is shown in FIG. 2A, the distal anchors 80 can extend distally when positioned in the capsule. The proximal end 301 of the implant 70 is restrained within the capsule 106 and within a portion of the inner retention member 40 and thus is generally constrained between the capsule 106 and the inner retention member 40.

The system 10 can first be positioned to a particular location in a patient's body, such as at the native mitral valve, through the use of the steering mechanisms discussed herein or other techniques.

Once the implant 70 is loaded into the delivery system 10, a user can thread a guide wire into a patient to the desired location. The guide wire passes through the lumen of the nose cone assembly 31, and thus the delivery system 10 can be generally advanced through the patient's body following the guide wire. The delivery system 10 can be advanced by the user manually moving the handle 14 in an axial direction. In some embodiments, the delivery system 10 can be placed into a stand while operating the handle 14 controls. In one embodiment, the delivery system may be axially advanced with a motor as shown in FIG. 17.

Once generally in the heart, the user can begin the steering operation of the rail assembly 20 using motor 500. The motor 500 can provide flexing/bending of the rail assembly 20 (either on the distal end or the proximal end), thus bending the distal end of the delivery system 10 in one, two, or more locations into the desired configuration. As discussed above, the user can provide multiple bends in the rail assembly 20 to direct the delivery system 10 towards the mitral valve. In particular, the bends of the rail assembly 20 can direct a distal end of the delivery system 10, and thus the capsule 106, along the center axis passing through the native mitral valve. Thus, when the outer sheath assembly 22, mid shaft assembly 21, inner assembly 18, and nose cone assembly 31 are together advanced over the rail assembly 20 with the compressed implant 70, the capsule 106 proceeds directly in line with the axis for proper release of the implant 70.

In a next step, the user can adjust the depth of the elongate shaft 12. The motor 500 may be utilized for such an operation. As discussed, adjusting the depth advances the inner shaft assembly 18, mid shaft assembly 21, outer sheath assembly 22, and nose cone assembly 31 over/through the rail assembly 20 while the implant 70 remains in the compressed configuration within the implant retention area 16. Due to the rigidity of, for example, either the inner shaft assembly 18, the mid shaft assembly 21, and/or the outer sheath assembly 22, these assemblies proceed straight forward in the direction aligned by the rail assembly 20.

Once in the release position, the motor 500 can operate to individually translate the outer sheath assembly 22 (and thus the capsule 106) with respect to the other assemblies, such as the inner assembly 18, in a proximal direction towards the handle 14 as shown in FIG. 28. By doing so, the distal end 303 of implant 70 is uncovered in the body, allowing for the beginning of expansion. At this point, the distal anchors 80 can flip proximally and the distal end 303 begins to expand radially outwardly. For example, if the system 10 has been delivered to a native mitral valve location through a transseptal approach, the nose cone is positioned in the left ventricle, preferably aligning the implant 70 such that it is generally perpendicular to the plane of the mitral annulus. The distal anchors 80 expand radially outwardly within the left ventricle. The distal anchors 80 can be located above the papillary heads, but below the mitral annulus and mitral leaflets. In some embodiments, the distal anchors 80 may contact and/or extend between the chordae in the left ventricle, as well as contact the leaflets, as they expand radially. In some embodiments, the distal anchors 80 may not contact and/or extend between the chordae or contact the leaflets. Depending on the position of the implant 70, the distal ends of the distal anchors 80 may be at or below where the chordae connect to the free edge of the native leaflets.

As shown in the illustrated embodiment, the distal end 303 of the implant 70 is expanded outwardly. It should be noted that the proximal end 301 of the implant 70 can remain covered by the outer retention ring during this step such that the proximal end 301 remains in a radially compacted state. At this time, the system 10 may be withdrawn proximally so that the distal anchors 80 capture and engage the leaflets of the mitral valve or may be moved proximally to reposition the implant 70. For example, the assemblies may be proximally moved relative to the rail assembly 20. In some embodiments, the distal anchors 80 may capture the native leaflet and be between the chordae without any further movement of the system 10 after withdrawing the outer sheath assembly 22.

During this step, the system 10 may be moved proximally or distally to cause the distal or ventricular anchors 80 to properly capture the native mitral valve leaflets. This can be done by the motor 500 moving the outer sheath assembly 22, mid shaft assembly 21, inner assembly 18, and nose cone assembly 31 with respect to the rail assembly 20. In particular, the tips of the ventricular anchors 80 may be moved proximally to engage a ventricular side of the native annulus, so that the native leaflets are positioned between the anchors 80 and the body of the implant 70. When the implant 70 is in its final position, there may or may not be tension on the chordae, though the distal anchors 80 can be located between at least some of the chordae.

The proximal end 301 of the implant 70 will remain in the outer retention ring 42 after retraction of the capsule 106. As shown in FIG. 29, once the distal end 303 of the implant 70 is fully expanded (or as fully expanded as possible at this point), the outer retention ring 42 can be individually withdrawn proximally with respect to the other assemblies, in particular relative to the inner assembly 18, to expose the inner retention member 40, thus beginning the expansion of the proximal end 301 of the implant 70. For example, in a mitral valve replacement procedure, after the distal or ventricular anchors 80 are positioned between at least some of the chordae tendineae and/or engage the native mitral valve annulus, the proximal end 301 of the implant 70 may be expanded within the left atrium.

The outer retention ring 42 can be moved proximally such that the proximal end 301 of the implant 70 can radially expand to its fully expanded configuration as shown in FIG. 30. After expansion and release of the implant 70, the inner assembly 18, nose cone assembly 31, mid shaft assembly 21, and outer sheath assembly 22 can be simultaneously withdrawn proximally along or relative to the rail assembly 20 back to their original position via the motor 500. In some embodiments, they are not withdrawn relative to the rail assembly 20 and remain in the extended position. Further, the nose cone 28 can be withdrawn through the center of the expanded implant 70 and into the outer sheath assembly 22 via the motor 500. The system 10 can then be removed from the patient.

The methods disclosed herein may utilize the systems and devices disclosed herein. For example, the motor 500 may deflect a portion of the delivery apparatus or deploy the implant to the body location. The operation of the motor 500 may be operated by a processor 536. A user may provide input to the processor 536 with a control device 504.

Further the sensors discussed herein may be utilized in certain embodiments. The delivery apparatus may include one or more sensors coupled to the delivery apparatus and configured to sense one or more of a condition of the patient's body or a condition of the delivery apparatus. The processor 536 may be configured to provide an output based on the one or more of a condition of the patient's body or a condition of the delivery apparatus sensed by the one or more sensors. For example, the processor may cause at least a portion of the delivery apparatus to avoid or retract from a surface of the patient's body based on a condition of the delivery apparatus.

Figure 31:
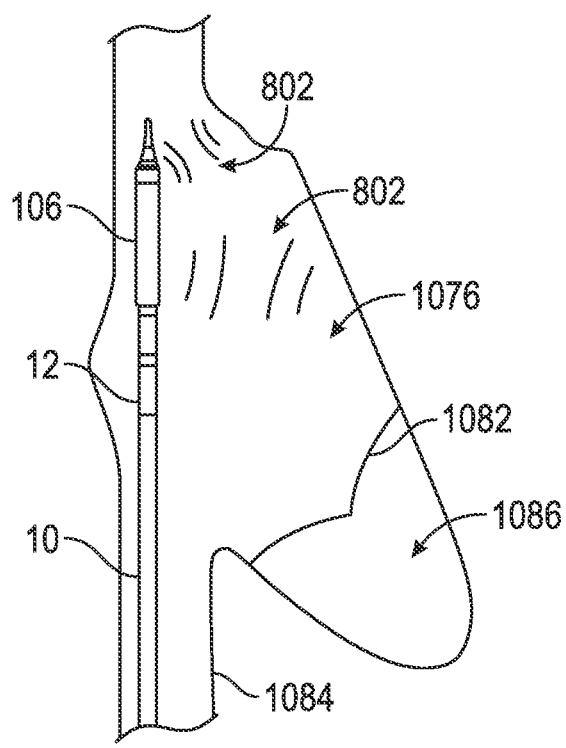
FIG. 31 illustrates a schematic view of a delivery system positioned within a right atrium of a patient's heart.

In embodiments, the delivery system 10 can be used in a method for percutaneous delivery of a replacement tricuspid valve that may be used to treat patients with moderate to severe tricuspid regurgitation. Such a method may utilize any of the systems or devices disclosed herein. Referring to FIG. 31, for example, the delivery apparatus may be extended within a portion of a patient's body to deliver an implant to a body location. The portion of the patient's body may be the right atrium 1076 and the body location for delivering the implant may be the native tricuspid heart valve 1082. The delivery apparatus may be extended within a portion of the patient's body in a similar manner as discussed in regard to FIG. 25, for example, the delivery apparatus can be placed in the ipsilateral femoral vein 1074 (marked in FIG. 25) and advanced towards the right atrium 1076. Other entry methods may be utilized as desired.

The delivery apparatus may be extended within the inferior vena cava 1084 into the right atrium 1076. As discussed with respect to the mitral valve delivery represented in FIG. 25, one or more guide wires may or may not be utilized as desired. One or more motors, which may be operated by a processor 536 as discussed herein, may be utilized to extend the delivery apparatus into the right atrium 1076.

The delivery apparatus may be steered through the complex areas of the heart in order to position a replacement tricuspid valve in line with the native tricuspid valve. The motor 500 may be operated to actuate the rail assembly 20 to target the distal end of the delivery apparatus to the appropriate area. For example, the motor 500 may be utilized to steer the rail assembly 20 to the desired orientation relative to the tricuspid heart valve 1082. The motor 500 may be operated by a processor 536 as discussed herein. The rail assembly 20 may form one or more bends such that the distal end of the delivery apparatus is oriented coaxial with the native tricuspid heart valve 1082.

Figure 32:
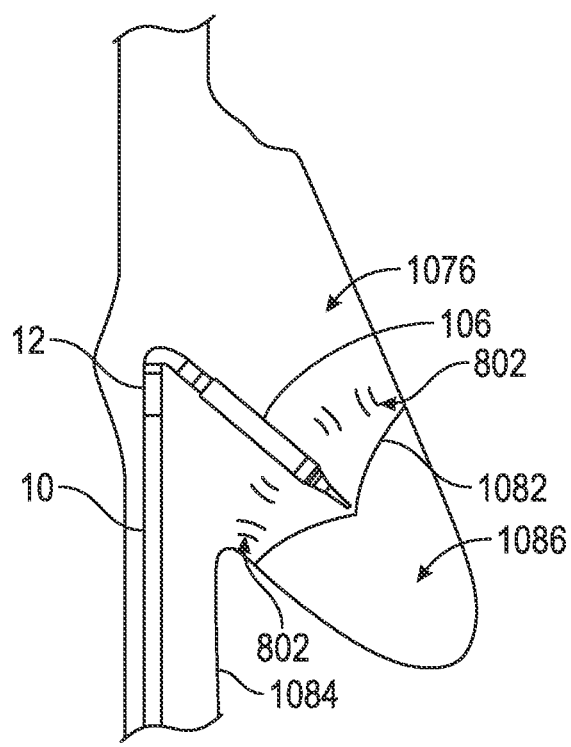
FIG. 32 illustrates a schematic view of the delivery system shown in FIG. 31 positioned within a right atrium of a patient's heart.

FIG. 32, for example, shows that the delivery apparatus has been deflected within the right atrium 1076 towards the native tricuspid heart valve 1082. One or more bends may be formed within the right atrium 1076 and/or the inferior vena cava 1084. Once the implant 70 is positioned coaxial with the native tricuspid heart valve 1082, the outer sheath assembly 22, mid shaft assembly 21, inner assembly 18, and nose cone assembly 31 can together be advanced (e.g., using the motor 500) distally relative to the rail assembly 20 towards the right ventricle 1086. The depth of the elongate shaft 12 may be varied by the operation of the motor 500 disclosed herein, which may be operated by a processor 536. The proximal/distal translation of the other assemblies over the rail assembly 20 allows for ventricular-atrial motion.

Figure 33:
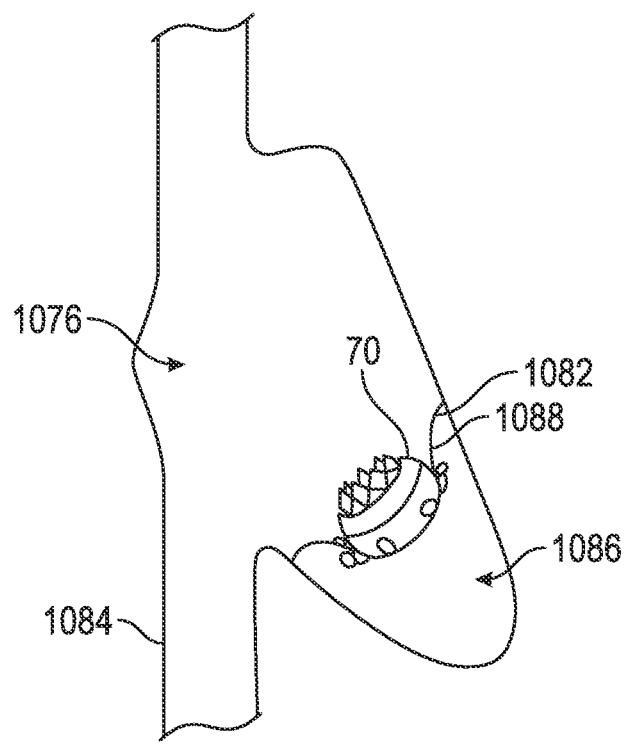
FIG. 33 illustrates a schematic view of a prosthetic tricuspid valve implanted in a native tricuspid valve.

The depth of the elongate shaft 12 may be varied until the capsule 106 is positioned in the desired location relative to the native tricuspid heart valve 1082. The distal end 303 of the implant 70, and specifically the distal anchors 80, may be restrained within the capsule 106 of the outer sheath assembly 22, thus preventing expansion of the implant 70. Similar to what is shown in FIG. 2A, the distal anchors 80 can extend distally when positioned in the capsule. The proximal end 301 of the implant 70 is restrained within the capsule 106 and within a portion of the inner retention member 40 and thus is generally constrained between the capsule 106 and the inner retention member 40. The implant 70 may then be deployed to the native tricuspid heart valve 1082 in a similar manner as discussed in regard to FIGS. 28-30. FIG. 33, for example, illustrates the implant 70 deployed to the native tricuspid heart valve 1082. The distal anchors of the implant 70 extend over the leaflets 1088 of the tricuspid heart valve 1082, in a similar manner as the distal anchors extend over the leaflets 1108 of the native mitral heart valve as shown in FIG. 26. The delivery apparatus may then be withdrawn from the patient's right atrium 1076.

The procedures disclosed with respect to FIGS. 31-33 may utilize the systems and devices disclosed herein. For example, the motor 500 may deflect a portion of the delivery apparatus or deploy the implant to the body location. The operation of the motor 500 may be operated by a processor 536. A user may provide input to the processor 536 with a control device 504. The system 10 can be positioned through the use of the steering mechanisms discussed herein or other techniques. The delivery system 10 can be advanced by the user manually moving the handle 14 in an axial direction. In some embodiments, the delivery system 10 can be placed into a stand while operating the handle 14 controls. In one embodiment, the delivery system may be axially advanced with a motor as shown in FIG. 17.

The delivery apparatus may be utilized in the form shown in FIG. 1, or other forms of delivery apparatuses may be utilized, for example, delivery apparatuses configured for delivery of an implant to the native tricuspid valve.

Further, the sensors discussed herein may be utilized in certain embodiments. The delivery apparatus may include one or more sensors coupled to the delivery apparatus and configured to sense one or more of a condition of the patient's body or a condition of the delivery apparatus. The processor 536 may be configured to provide an output based on the one or more of a condition of the patient's body or a condition of the delivery apparatus sensed by the one or more sensors. For example, the processor 536 may cause at least a portion of the delivery apparatus to avoid or retract from a surface of the patient's body based on a condition of the delivery apparatus. FIGS. 31 and 32, for example, illustrate sensor signals 802 produced by proximity sensors 582 (as marked in FIG. 21) that may be utilized to navigate within the patient's body. The processor may navigate the delivery apparatus to the desired orientation relative to the native tricuspid valve for deployment of the implant 70. The processor may actuate the delivery apparatus to align coaxial with the native tricuspid valve and deliver the implant 70 to the native tricuspid valve.

In embodiments, the delivery system 10 can be used in a method for percutaneous delivery of a replacement aortic valve. Such a method may utilize any of the systems or devices disclosed herein. Further, such a method may utilize a delivery system including a delivery apparatus that is configured for delivery of a prosthetic replacement aortic valve. Such a delivery apparatus may include similar components as the apparatus shown in FIG. 1, for example, the delivery apparatus may include an elongate shaft 804 including a capsule 806 surrounding an implant retention area for retaining the implant, and may include a nose cone 808 at a distal end of the elongate shaft 804. The delivery apparatus may include a housing that may be in the form of a handle at the proximal end of the elongate shaft 804. The delivery apparatus may include a plurality of assemblies, as disclosed with respect to the embodiment of FIG. 1. The assemblies may be controlled by a motor and may be controlled by a controller including a processor as disclosed herein. As such, the actuation of the delivery apparatus may be controlled by a motor and a processor. The delivery apparatus may be configured to extend around the curve of a patient's aortic arch 1090 and deliver an implant to the aortic valve 1092. For example, a steering mechanism may be utilized that is configured to steer around the curve of the patient's aortic arch 1090. The delivery apparatus may further include the sensors and other components disclosed with respect to the apparatus shown in FIG. 1, as desired.

Figure 34:
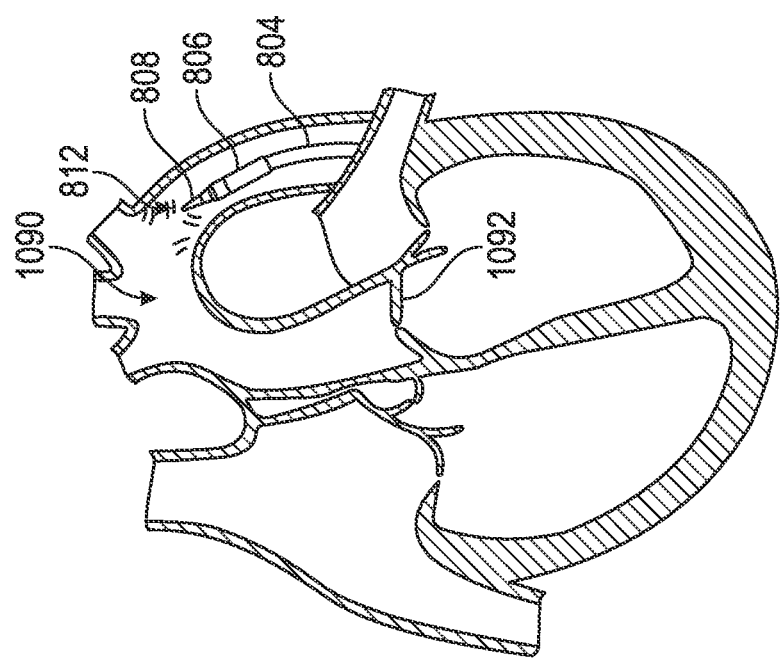
FIG. 34 illustrates a schematic view of a delivery system extending through an aortic arch of a patient's heart.

Referring to FIG. 34, for example, the delivery apparatus may be extended within a portion of a patient's body to deliver an implant to a body location. The portion of the patient's body may be the aortic arch 1090 and the body location for delivering the implant may be the native aortic heart valve 1092. The delivery apparatus may be extended within a portion of the patient's body percutaneously, for example, the delivery apparatus can be placed in a femoral vein and advanced towards the aortic arch 1090. Other entry methods may be utilized as desired.

The delivery apparatus may be passed through the aortic arch 1090 and advanced towards the native aortic heart valve 1092. One or more guide wires may or may not be utilized as desired. One or more motors, which may be operated by a processor 536 as discussed herein, may be utilized to extend the delivery apparatus through the aortic arch 1090.

The motor 500 may be operated to actuate the rail assembly 20, or another steering mechanism of the delivery apparatus, to target the distal end of the delivery apparatus to the appropriate area. For example, the motor 500 may be utilized to steer the rail assembly 20 to the desired orientation relative to the native aortic heart valve 1092. The motor 500 may be operated by a processor 536 as discussed herein. The rail assembly 20, or another steering mechanism of the delivery apparatus, for example one or more pull wires, may form one or more bends such that the distal end of the delivery apparatus is oriented coaxial with the native aortic heart valve 1092.

Figure 35:
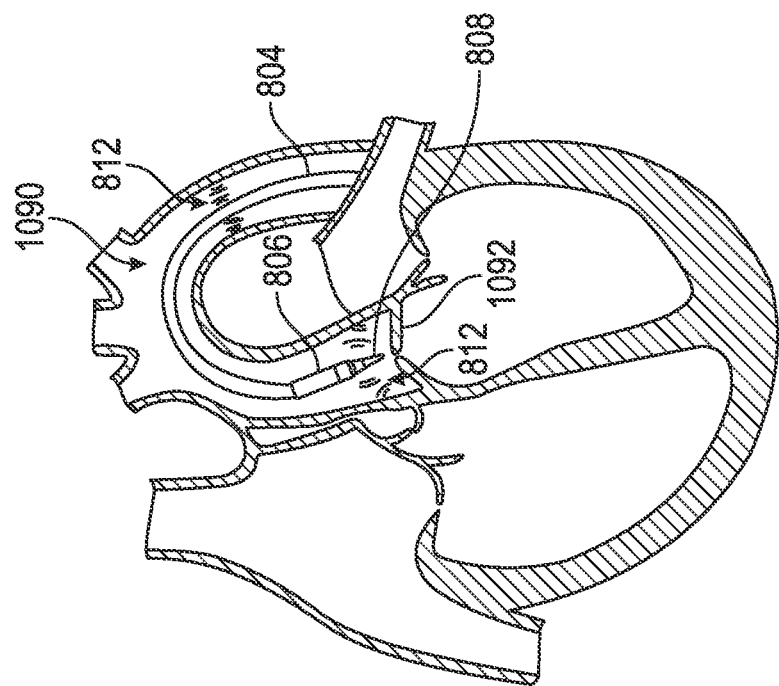
FIG. 35 illustrates a schematic view of the delivery system shown in FIG. 34 extending through an aortic arch of a patient's heart.

FIG. 35, for example, shows that the delivery apparatus has been deflected within the aortic arch 1090 towards the native aortic heart valve 1092. A bend may be formed within the aortic arch 1090. Once the implant is positioned coaxial with the native aortic heart valve 1092, the capsule 806 may be further advanced to the desired depth relative to the native aortic heart valve 1092.

The depth of the capsule 806 may be varied until the capsule 806 is positioned in the desired location relative to the native aortic heart valve 1092. The implant may be restrained within the capsule 806 of an outer sheath assembly, thus preventing expansion of the implant. The implant may then be deployed by the outer sheath of the capsule 806 being retracted or otherwise moved relative to the implant retention area. The implant may have a variety of forms, including the form of the implant shown in FIG. 3B. In embodiments, the implant may not be covered by a capsule. For example, the implant may be a balloon expandable or mechanically expandable implant that is not restrained within a capsule, or other form of implant. The implant may be deployed at the desired location.

Figure 36:
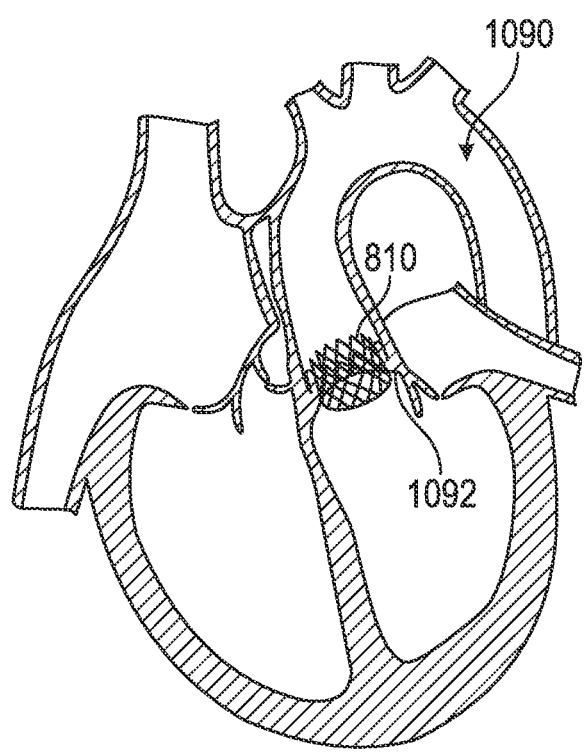
FIG. 36 illustrates a schematic view of a prosthetic aortic valve implanted in a native aortic valve.

FIG. 36 illustrates the implant 810 deployed to the native aortic heart valve 1092. The delivery apparatus may be withdrawn from the patient's aortic arch 1090.

The method disclosed with respect to FIGS. 34 through 36 may utilize the systems and devices disclosed herein. For example, the motor 500 may deflect a portion of the delivery apparatus or deploy the implant to the body location. The operation of the motor 500 may be operated by a processor 536. A user may provide input to the processor 536 with a control device 504. The system 10 can be positioned through the use of the steering mechanisms discussed herein or other techniques. The delivery system can be advanced by the user manually moving a handle in an axial direction. In some embodiments, the delivery system can be placed into a stand while operating the handle controls. In one embodiment, the delivery system may be axially advanced with a motor as shown in FIG. 17.

Further the sensors discussed herein may be utilized in certain embodiments. The delivery apparatus may include one or more sensors coupled to the delivery apparatus and configured to sense one or more of a condition of the patient's body or a condition of the delivery apparatus. The processor 536 may be configured to provide an output based on the one or more of a condition of the patient's body or a condition of the delivery apparatus sensed by the one or more sensors. For example, the processor may cause at least a portion of the delivery apparatus to avoid or retract from a surface of the patient's body based on a condition of the delivery apparatus. FIGS. 34 and 35, for example, illustrate sensor signals 812 (e.g., echo signals) produced by proximity sensors 582 (as marked in FIG. 21) that may be utilized to navigate within the patient's body. A spatial relationship between the delivery apparatus and the surface of the aortic arch may be sensed with sensors. The sensor signals 812 are shown reflecting from the surface of the aortic arch 1090. The processor may actuate the delivery apparatus to avoid or retract from a surface of the patient's body by deflecting within the aortic arch based on the spatial relationship, and navigate around the aortic arch to the desired orientation relative to the native aortic heart valve 1092 for deployment of the implant 810. By continually sensing the position of the delivery apparatus relative to the aortic arch and modifying the deflection accordingly, it is thereby possible to navigate through the aortic arch with little or no contact with the vessel wall. As noted above, the sensor feedback from the delivery apparatus may be supplemented by imaging feedback such as from a fluoroscope to provide additional detail. The use of sensor feedback during advancement through a vessel, such as an aortic arch, provides an important improvement because it reduces the likelihood of vascular dissection and/or causing a particle to break free from the vessel wall. In another advantage, the replacement valve may be precisely positioned relative to the native aortic heart valve, which thereby facilitates crossing the native aortic leaflets and accurately deploying the replacement valve within the diseased native valve.

In other embodiments, other methods of delivering the implant to the native aortic heart valve may be utilized, for example, a transapical, transseptal, or other method may be utilized.

Other locations for valve implant may include the pulmonary valve, and other valves of a patient's body. Other forms of implants may be delivered to other body locations as desired.

In embodiments disclosed herein, the implant can be delivered under fluoroscopy so that a user can view certain reference points for proper positioning of the implant. Further, echocardiography can be used for proper positioning of the implant.

In one embodiment, the proximity sensor 582 may be configured to provide a model of the interior of the patient's body and the spatial relationship of the elongate shaft 12 from surfaces of the patient's body. Such a model may be provided on output devices 584, 586 shown in FIGS. 37 and 38 as display screens (on a monitor and on a virtual reality or augmented reality display). Such a model may also be provided by other sensors positioned external to the patient's body if desired. Such a model may be a two-dimensional map or three-dimensional map of the patient's body for view by a user, and for use by the processor 536 as feedback to navigate through the patient's body and deliver an implant 70 to the desired location. Such a configuration may be utilized with any embodiment disclosed herein, including delivery of an implant to a native aortic valve.

FIG. 37 illustrates an embodiment in which operation of the delivery apparatus may occur remotely by a user. The user may utilize a control device 588 such as a joystick or other form of control device to control movement of the delivery apparatus and elongate shaft 12. The control device 588 may be configured to sense motion of the control device to control the delivery apparatus. The user may view the position of the elongate shaft 12 on an output device 584 in the form of a display screen. The position may be provided in a variety of manners, including external sensing of the position via sensors using fluoroscopy or echocardiography. The position may also be provided via an image produced by signals from proximity sensors of the elongate shaft 12. The proximity sensors may be configured to produce an image of the spatial relationship between the elongate shaft 12 and the surfaces of the patient's body. A configuration including a motor for axial movement of the elongate shaft 12, as shown in FIG. 17, may be utilized as well for remote control of the procedure. Such a configuration may be utilized with any embodiment disclosed herein, including delivery of an implant to a native aortic valve.

FIG. 38 illustrates an embodiment in which the output device 586 is in the form of a display screen on a virtual reality or augmented reality display. The display may include a helmet (or other headset that allows for enhanced visualization) for wear by the user, wherein the user is able to moves his or her head to alter the perspective of the view provided by the display screen. Similar to the embodiment discussed with respect to FIG. 37, the position of the elongate shaft 12 and portions of the patient's heart seen in the output device 586 may be provided in a variety of manners, including external sensing of the position via fluoroscopy or echocardiography. The position may also be provided via an image produced by signals from proximity sensors of the elongate shaft 12. The proximity sensors may be configured to produce an image of the spatial relationship between the elongate shaft 12 and the surfaces of the patient's body. A configuration including a motor for axial movement of the elongate shaft 12, as shown in FIG. 17, may be utilized as well for remote control of the procedure. Such a configuration may be utilized with any embodiment disclosed herein, including delivery of an implant to a native aortic valve.

Figure 39:
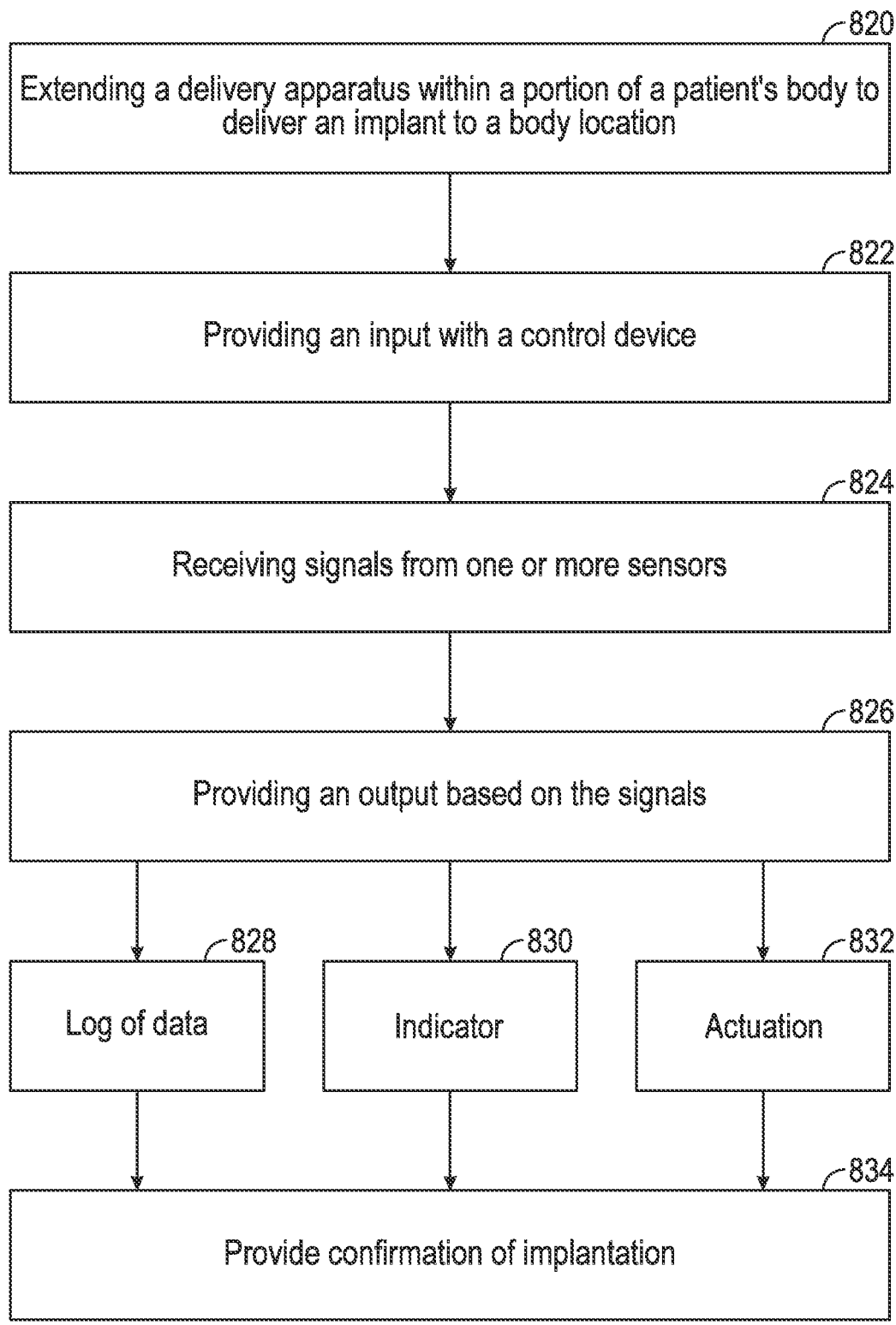
FIG. 39 illustrates a flow chart of a method according to an embodiment of the disclosure.

FIG. 39 illustrates an exemplary method that may utilize devices and systems disclosed herein. The method is exemplary in nature, and features of the method may be removed or added to, and the order of steps may be varied as desired. The features of the method may be combined or substituted with other features of devices, systems, and methods disclosed herein. The features of the method may be utilized in the embodiments disclosed in FIGS. 25-36.

The method may include a step 820 of extending a delivery apparatus within a portion of a patient's body to deliver an implant to a body location. The delivery apparatus may be configured similarly as any embodiment of delivery apparatus disclosed herein. The delivery apparatus may be extended within a portion of the patient's body as shown in the embodiments of FIGS. 25-36 or any other manner disclosed herein. The implant may be configured similarly as any implant disclosed herein, and the body location may comprise any location disclosed herein. At least a portion of the delivery apparatus may be actuated by at least one motor operated by a processor.

The delivery apparatus may be extended within the portion of the patient's body by way of a user (e.g., clinician) advancing the delivery apparatus, such as the elongate shaft of the delivery apparatus within the patient's body. The delivery apparatus may be advanced manually by the user. For example, the user may manually grip a handle of the delivery apparatus or a control mechanism to advance the delivery apparatus. In embodiments, an automated method may be utilized, for example, utilizing a motor driven rail 577, as shown in FIG. 17, or other assembly that actuates axial movement of the delivery apparatus into the patient's body. In embodiments, the delivery apparatus may be advanced remotely by the user, for example, utilizing a remote control device 588 as shown in FIGS. 37 and 38. In other embodiments, other methods may be utilized to extend the delivery apparatus within the portion of the patient's body.

Referring to step 822, an input may be provided with a control device. The input may be provided by a user to actuate at least a portion of the delivery apparatus. A control device such as a control devices 504, 556, 562, 588 shown in FIG. 13, 15, 16, 37, or 38, or another form of control device may be utilized as desired. The input may be provided to control a movement of the delivery apparatus. For example, the user may determine to deflect the delivery apparatus or control a depth of the delivery apparatus to a desired orientation. FIG. 25 illustrates an elongate shaft of a delivery apparatus being deflected to a desired orientation towards a native mitral valve. FIG. 32 illustrates an elongate shaft of a delivery apparatus being deflected to a desired orientation towards a native tricuspid valve. FIG. 35 illustrates an elongate shaft of a delivery apparatus being deflected to a desired orientation within an aortic arch. A variety of forms of deflections may occur, as well as variations in the depth of the delivery apparatus. The user may further provide an input to perform an operation of the delivery apparatus, for example to deploy the implant either fully or partially. The user may view the position of the delivery apparatus within the patient's body on an output device, such as a display screen 584 as shown in FIG. 37. The image on the display screen 584 may be produced by sensors external to the patient's body, such as fluoroscopy or echocardiography sensors, and/or may be provided via signals from proximity sensors of the elongate shaft. The user may view of a model of an interior of the patient's body on the output device, as discussed in regard to FIG. 37.

In embodiments, the input may be provided remotely by the user, for example, utilizing a remote control device 588 as shown in FIGS. 37 and 38.

The input provided by the control device may be utilized to operate the motor and may be provided to the processor 536. The processor 536 accordingly may be utilized to operate the motor to produce the desired actuation of the delivery apparatus.

Referring to step 824, signals may be received from one or more sensors. The signals may be received by the processor 536 and may comprise feedback signals that are provided to the processor 536 from the sensors. The sensors may include any of the sensors disclosed herein, including sensors for sensing a condition of the delivery apparatus or sensing a condition of the patient's body. Such sensors may include the position sensors, motor torque sensors, contact sensors, proximity sensors, pressure sensors, flow sensors, or other forms of sensors disclosed herein. The sensors may operate in manners disclosed herein. The sensor signals may be provided during an implantation procedure and may be provided in real-time to the processor 536 as feedback signals during the procedure. For example, the proximity sensor 582 may provide a signal indicating that the delivery apparatus has contacted or is proximate a surface of the surface of the patient's body. A pressure sensor 578 may provide a signal indicating a pressure, such as a fluid pressure, within the patient's body. Other sensors may be utilized and may operate in manners disclosed herein. In embodiments, the sensors may not be coupled to the delivery apparatus and may be positioned external to the patient's body. The sensors, for example, may be sensors that are utilized in fluoroscopy and/or echocardiography, and may be provided to the processor 536 for the processor to determine the location of the delivery apparatus within the patient's body.

Referring to step 826, an output may be provided based on the signals. The processor 536 may provide the output based on the signals. The processor 536 may be configured to provide an output based on the one or more of a condition of the patient's body or the condition of the delivery apparatus sensed by the one or more sensors. The output may have a variety of forms as disclosed herein. For example, the output may comprise a log of data 828. Such a log of data may be for an implantation procedure with the delivery apparatus and may be stored in the memory 534 and may have a form as disclosed herein. The data may be stored for later retrieval by a user for analysis or may record a log of actions taken by the delivery apparatus. For example, the position sensor signals may be logged to record the movements of the delivery apparatus, among other forms of sensors signals. In embodiments, the log of data may be utilized to allow the system to learn from past events and may be utilized in a machine learning algorithm to allow the system to continually refine the procedure to enhance the probability of success. The log of data may include data from implantation procedures or characteristics of the patient, for use in a machine learning algorithm that may use such data.

The output may comprise an indicator 830. The indicator may be produced by the processor 536 in manners disclosed herein and may be provided on an output device. A condition of the delivery apparatus or a condition of the patient's body may be indicated to a user in a variety of forms, for example, an output device may include one or more of a display screen, a light, a speaker, or a haptic device, among other forms of output devices. The user may be able to respond to the indicator. For example, if the indicator indicates that the proximity sensor 582 sensed that the delivery apparatus has contacted or is proximate a surface of the patient's body, then the user may be able to respond and actuate the delivery apparatus away from the surface. Further, if the indicator indicates that a flow sensor 583 senses an undesired flow within the patient's body during implantation, then the user may be able to respond and redeploy the implant if desired. The indicator may indicate whether the implantation procedure is operating desirably, or may indicate an undesirable operation of the implantation procedure. Other forms of indicators may be provided as disclosed herein, and the user may respond in a desired manner.

The output may comprise an actuation 832 of at least a portion of the delivery apparatus. The processor 536 may provide an output that comprises a control of the motor 500 based on the signals from the one or more sensors. For example, a signal from a contact sensor 580 or a proximity sensor 582 may be provided to the processor 536 as feedback that the delivery apparatus has contacted or is proximate a surface of the patient's body. The processor 536 accordingly may provide an output that operates the motor 500 based on feedback from the sensors to avoid or retract from the surface of the patient's body. A signal from the flow sensors 583*a*-1 may cause the processor 536 to provide an output to the motor 500 to redeploy the implant 70 or move the portion of the delivery apparatus to recapture the leaflet 1108. A signal from a position sensor may provide feedback to the processor 536 regarding whether the delivery apparatus is performing the correct movements, and the processor 536 may operate the motor 500 to perform corrective movements if desired (e.g., deflect the elongate shaft 12 if needed). The processor 536 may be programmed to automatically respond and produce outputs based on the condition of the patient's body or a condition of the delivery apparatus sensed by the one or more sensors. The programming for the processor 536 may be stored in the memory 534 and operated by the processor 536.

In embodiments, the processor 536 may be configured to adjust an input that is provided by a user, for example, in step 822, based on the feedback from the sensors. For example, if the user is providing a control to direct the elongate shaft towards a surface of the patient's body, and the proximity sensor 582 determines that such action brings the elongate shaft within a certain threshold of proximity to the surface, then the processor 536 may determine that the user's input is unsafe and may automatically adjust the input to avoid or retract from the surface of the patient's body. As such, the processor 536 may automatically operate the delivery apparatus to adjust the input provided by a user, which may include overriding the input provided by the user.

Similarly, if a flow sensor 583 senses that undesired flow is provided during implantation of a valve, then the processor may automatically operate the delivery apparatus to adjust an input provided by a user to properly implant the valve. The processor 536 may operate based on any sensor signals disclosed herein to adjust the input provided by a user.

The actuation produced by the processor 536 may be based on a machine learning algorithm utilizing data from past implantation procedures or from characteristics of the patient. The data may be "learned" from previous procedures and, in particular, learned from previous procedures performed on patients with similar anatomies and/or other characteristics. Therefore, procedural steps performed successfully on patients with similar anatomies could be duplicated, thereby increasing the probability of a successful procedure on the current patient. A machine learning algorithm may be utilized by the processor 536 to control actuation of the delivery apparatus, and may be used to adjust the input provided by a user.

Further, the actuation produced by the processor 536 may be based on a programmed series of movements that are to be performed by the delivery apparatus. Such a program may be pre-programmed into the processor 536 or may be programmed based on a model or map of the patient's anatomy as discussed in regard to FIG. 37. For example, external sensors may be utilized to determine a model or map of the patient's anatomy and the processor 536 may be programmed with movements to deliver the implant to the desired body location. The programming may also occur during the implantation procedure, for example, based on the feedback from sensors. If the input from the user strays from the desired movements within a certain threshold, then the processor 536 may be configured to automatically adjust the input to move the delivery apparatus in the desired manner. As such, the processor 536 may be programmed to reduce the possibility of the user performing an undesired procedure during implantation.

Referring to step 834, a confirmation of implantation may be provided. Such a confirmation may be provided by the processor 536, and may be provided based on signals from sensors. For example, a pressure sensor or flow sensor, or other form of sensor, may determine that the implant has been implanted. The processor 536 may be configured to provide such a confirmation of implantation as an indicator on an output device, so that the user is notified that the implant has been implanted. The user may then perform steps to withdraw the delivery apparatus from the patient's body and otherwise complete the implantation procedure.

In the exemplary method discussed in regard to FIG. 39, a user (e.g., clinician) may provide input, which may be assisted by use of the components disclosed herein (e.g., the processor, motor, and one or more sensors, among other components). In embodiments, however, an implantation procedure may occur autonomously (i.e., adapts to environment during operation). The processor may perform autonomous control of the delivery apparatus to perform the implantation procedure. A user may provide some input during the procedure, such that the procedure may occur semi-autonomously. As such, a method may occur autonomously or semi-autonomously (or at least semi-autonomously).

Figure 40:
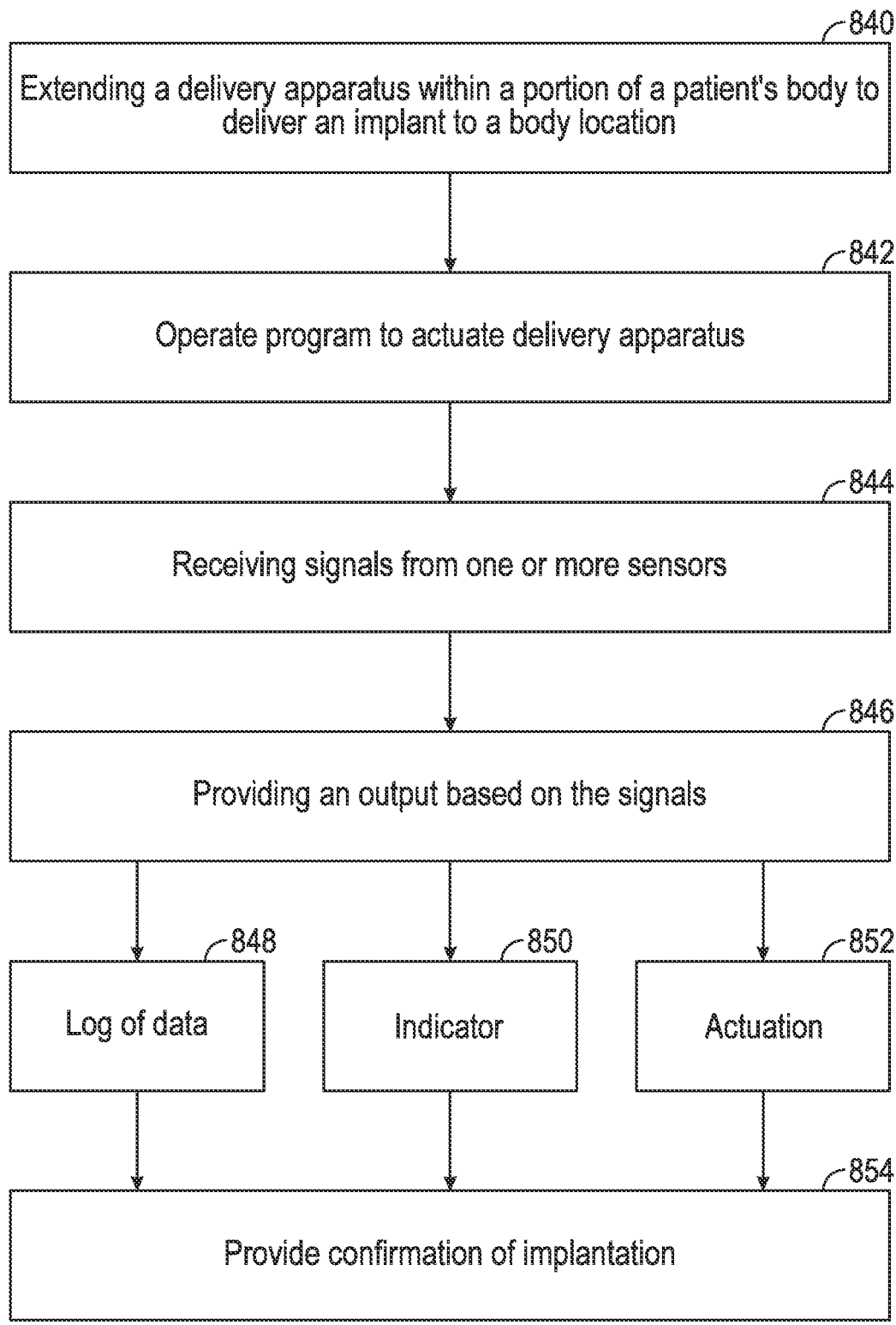
FIG. 40 illustrates a flow chart of a method according to an embodiment of the disclosure.

FIG. 40, for example, illustrates a method of autonomous control of the delivery apparatus. A user may provide some input during the procedure, such that the procedure may occur semi-autonomously or least semi-autonomously. Similar to the method disclosed in regard to FIG. 39, the method of FIG. 40 is an exemplary method that may utilize devices and systems disclosed herein. Features of the method may be removed or added to, and the order of steps may be varied as desired. The features of the method may be combined or substituted with other features of devices, systems, and methods disclosed herein. The features of the method may be utilized in the embodiments disclosed in FIGS. 25-36.

The method may include a step 840 of extending a delivery apparatus within a portion of a patient's body to deliver an implant to a body location. The delivery apparatus may be configured similarly as any embodiment of delivery apparatus disclosed herein. The delivery apparatus may be extended within a portion of the patient's body as shown in the embodiments of FIGS. 25-36 or any other manner disclosed herein. The implant may be configured similarly as any implant disclosed herein, and the body location may comprise any location disclosed herein.

The delivery apparatus may be extended within the portion of the patient's body by way of a motor advancing the delivery apparatus, such as the elongate shaft of the delivery apparatus within the patient's body. The motor may be controlled by the processor 536. For example, a motor driven rail 577, as shown in FIG. 17, or other assembly that actuates axial movement of the delivery apparatus into the patient's body may be utilized. In other embodiments, other methods may be utilized to extend the delivery apparatus within the portion of the patient's body.

Referring to step 842, the processor 536 may operate a program to actuate the delivery apparatus. The processor 536 may be programmed with a sequence of movements to actuate the delivery apparatus to the desired location and for the desired deployment operation. For example, the processor 536 may be configured to determine the desired delivery location and the path and orientation to be followed to reach the desired delivery location based on external sensing of the position via fluoroscopy or echocardiography and/or the position being determined via signals from proximity sensors of the elongate shaft 12. The programmed sequence of movement may be provided based on the geometry of the path to the desired implant location, and the orientation of the desired implant location. The movement and deployment of the delivery apparatus may be preprogrammed into the processor 536 and may be individualized based on the particular path to the desired location in the patient's body to be followed. In certain embodiments, a machine learning algorithm may be utilized by the processor 536 to control actuation of the delivery apparatus. For example, the path and orientation also be supplemented by data from previous procedures on patients with similar characteristics. The processor 536 and programming may be utilized to extend the delivery apparatus within a portion of the patient's body as disclosed in regard to step 840.

Referring to step 844, the processor 536 may continue to follow the program, and may receive signals from one or more sensors. The processor 536 may receive feedback from sensors (as discussed herein) that cause the processor 536 to produce outputs in step 846. The signals from the sensors may be utilized by the processor 536 in a similar manner as disclosed with respect to step 826 and may produce similar outputs 848, 850, 852 as disclosed regarding the outputs 828, 830, 832 of FIG. 39. For example, the processor 536 may be configured to produce a log of data 848 in a similar manner as disclosed regarding the method of FIG. 39. The processor 536 may be configured to produce an indicator 850 in a similar manner as disclosed regarding the method of FIG. 39. The indicator 850 may be provided for a user to determine whether to intervene in a procedure. For example, if a user (e.g., a clinician) receives an indicator that the autonomously operated delivery apparatus has contacted a surface or has improperly deployed an implant, then the user may intervene to attempt to correct such actuation.

The processor 536 may be configured to produce actuation 852 of the delivery apparatus. The actuation 852 may be provided for the processor 536 to correct the path and operation with minimal or no human interaction using feedback from sensors as discussed herein, to complete the procedure. For example, if the position sensor indicates the delivery apparatus is straying from the intended path, the processor 536 may automatically adjust the path. If the proximity sensor indicated the delivery apparatus is approaching a surface, then the processor 536 may automatically adjust the path. The processor 536 may be used to navigate to any desired location for delivery of the implant. Such navigation is shown, for example, in FIGS. 25, 31, 32, 34, and 35, among other forms of navigation. Any of the sensors and feedback operations from the sensors disclosed herein may be utilized in such a method. In certain embodiments, a user may provide some input during the procedure to correct the procedure or otherwise provide input to control the procedure.

Similar to the method discussed in regard to FIG. 39, the actuation produced by the processor 536 may be based on a machine learning algorithm utilizing data from past implantation procedures or from characteristics of the patient. The actuation may be based on data "learned" from previous procedures and, in particular, learned from previous procedures performed on patients with similar anatomies and/or other characteristics. Therefore, procedural steps performed successfully on patients with similar anatomies could be duplicated, thereby increasing the probability of a successful procedure on the current patient. A machine learning algorithm may be utilized by the processor 536 to control actuation of the delivery apparatus.

The processor 536 may be configured to operate the motor 500 to produce the desired actuation of the delivery apparatus. The processor 536 may be configured to automatically operate the motor to deflect the delivery apparatus to the desired body location. The processor 536 may be configured to automatically operate the motor to deflect the delivery apparatus in at least two planes. The processor 536 may be configured to automatically deploy the implant 70 to the desired location and complete the delivery procedure. The processor 536 may be configured to complete the delivery procedure in certain embodiments without control or intervention by a user. In step 854, a confirmation of implantation may be provided in a similar manner as with step 834 in FIG. 39. The processor 536 may be configured to provide such a confirmation of implantation as an indicator on an output device, so that the user is notified that the implant has been implanted.

The methods of FIGS. 39 and 40 may be utilized for replacement or repair of a heart valve within a patient's body. The heart valve may comprise one or more of an aortic heart valve, a mitral heart valve, a tricuspid heart valve, or a pulmonary heart valve. Other valves or body locations for implantation may be treated in other embodiments. Variations on the methods of FIGS. 39 and 40 may be provided as desired.

Figure 41:
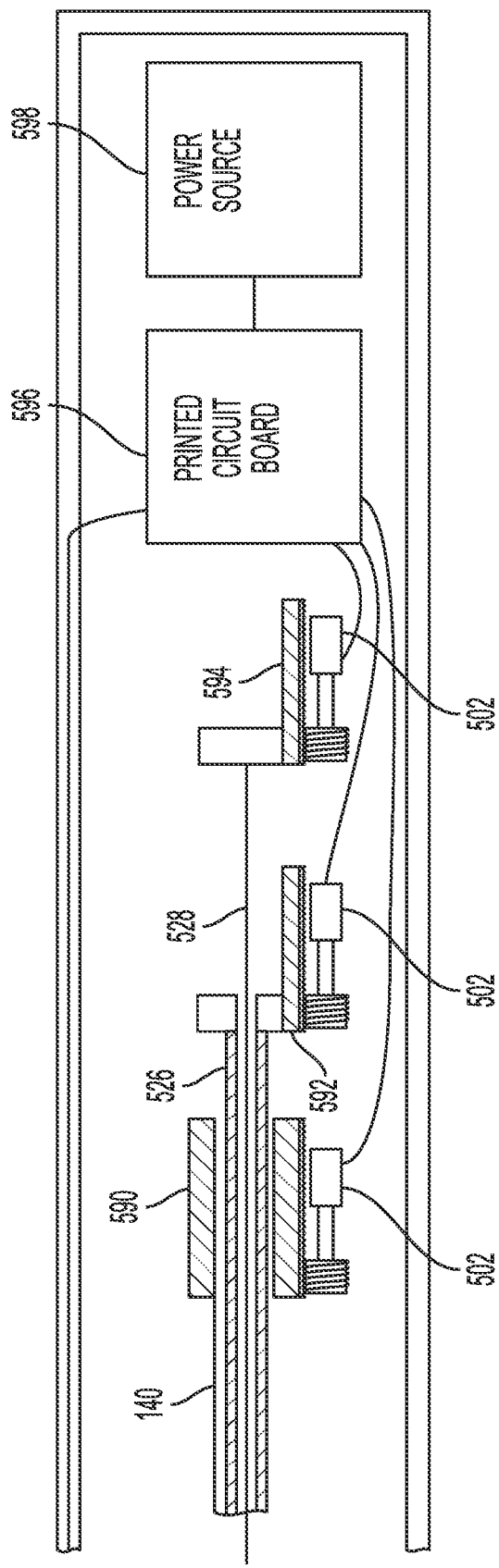
FIG. 41 illustrates a cross section view of an embodiment of a delivery system handle.

FIG. 41 illustrates an embodiment of a delivery apparatus configured similarly as the apparatus shown in FIG. 10, however, multiple motors 502 may be utilized to control actuation of the delivery apparatus. The multiple motors 502, for example, may each be configured to engage respective adaptors 590, 592, 594 configured to actuate portions of the delivery apparatus. The motors 502 may be configured to perform linear movement of the adaptors 590, 592, 594 to cause actuation of the delivery apparatus. Further, in the embodiment of FIG. 41, the processor, memory, and input device and output device of FIG. 41 may be provided on a printed circuit board 596 positioned within the handle. A power source 598 such as a battery pack or other form of power source may also be utilized within the handle. The embodiment of FIG. 41 may comprise a self-contained handle unit including a processor for performing a delivery procedure and receiving feedback from sensors, as well as performing data logging if desired.

The motors disclosed herein may comprise a variety of forms of motors, including electromagnetic, stepper, hydraulic, piezoelectric, among others.

Figure 43:
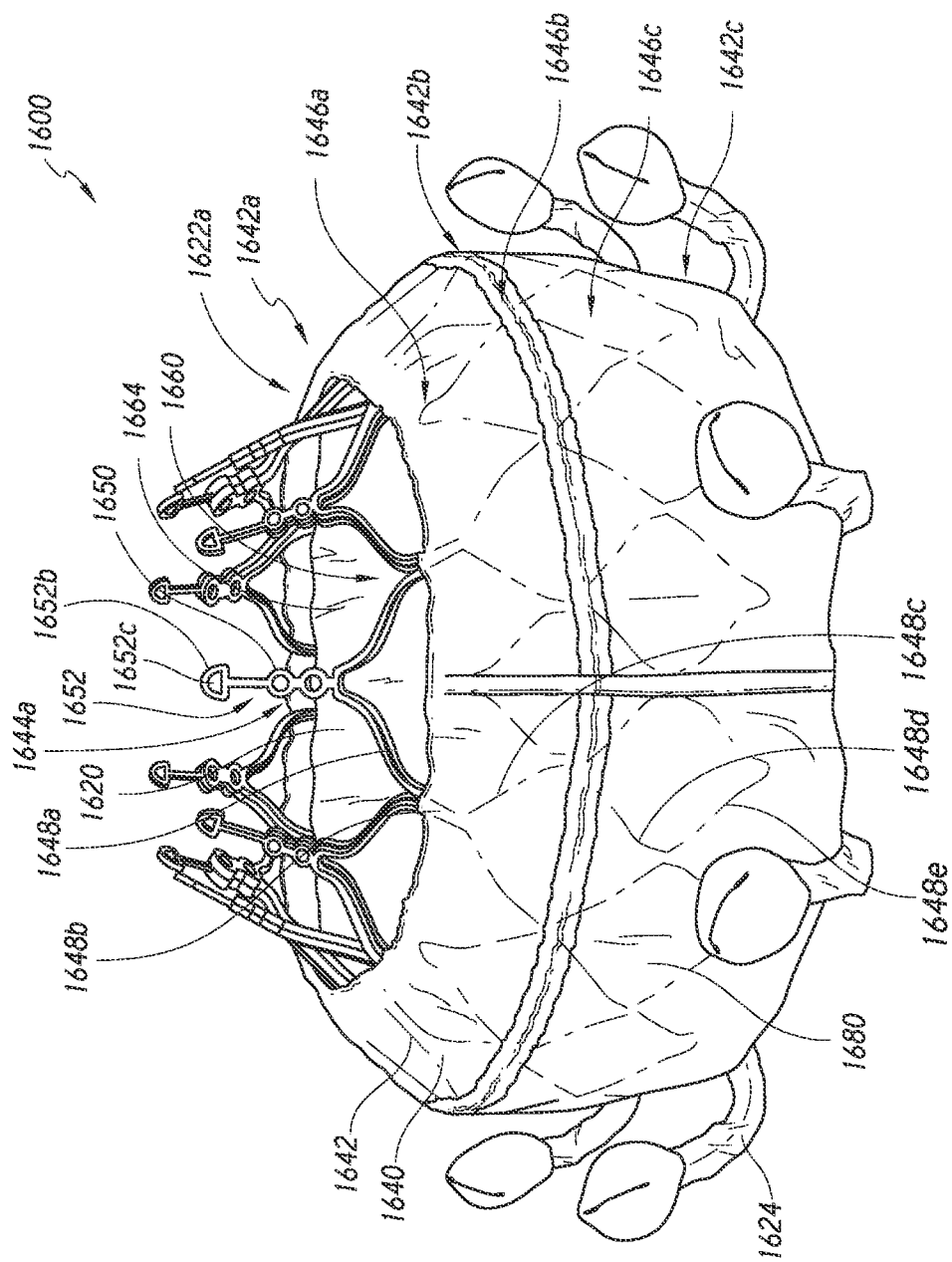
FIG. 43 illustrates a perspective view of an embodiment of an implant.
Figure 44:
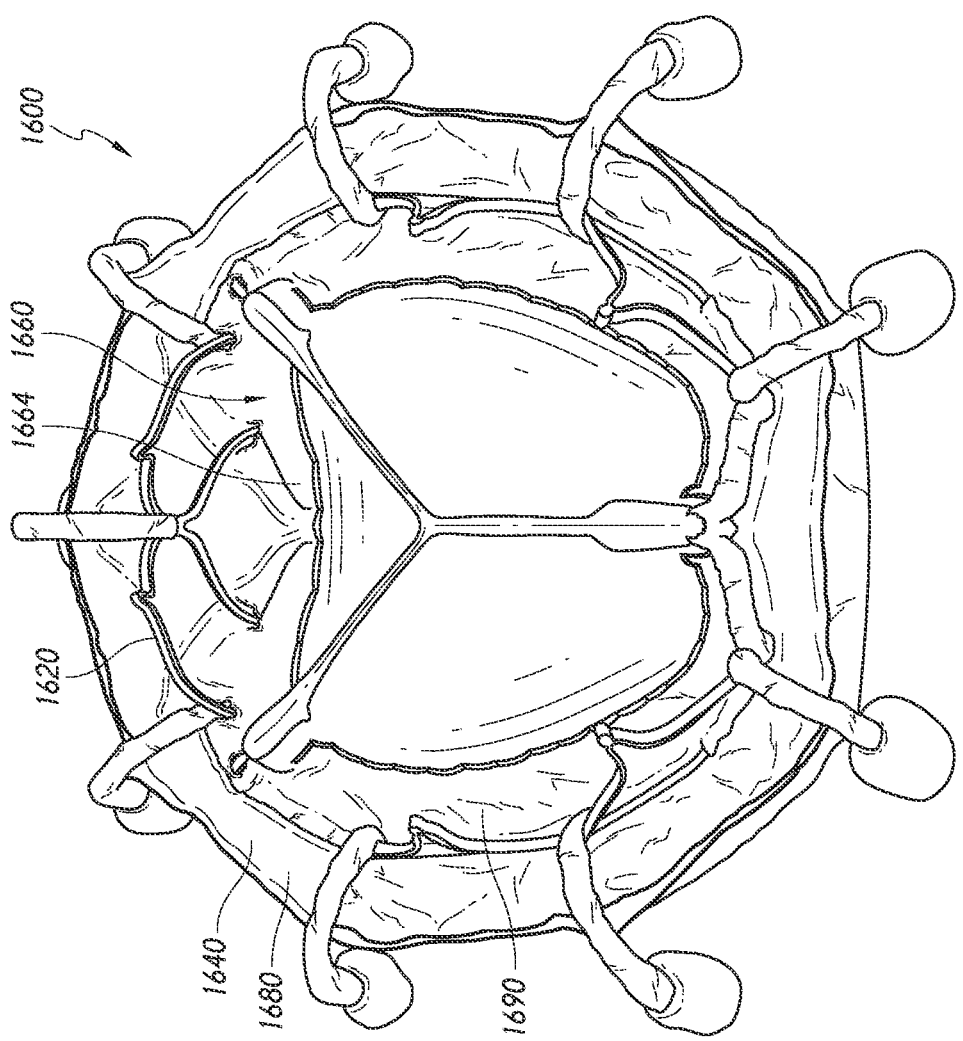
FIG. 44 illustrates a top view of the implant shown in FIG. 43.

Although many of the systems and methods disclosed herein have been discussed with respect to implantation of a prosthetic mitral valve implant, the systems and methods are also applicable to replacement of other heart valves, such as the tricuspid, aortic, and pulmonary valve. It is also understood that the systems and methods may be utilized to deliver a variety of implants, including implants for repair of a heart valve. For example, other types of heart valve implants that may be utilized are shown in FIGS. 42-44, among other types of implants (e.g., aortic valve implants and other repair implants).

The delivery apparatuses utilized herein may be configured as the delivery apparatus shown in FIG. 1, or may have a variety of other configurations. For example, delivery apparatuses may be utilized that are configured to deliver implants to the native aortic valve, and may be configured to pass through the aortic arch. The delivery apparatus may be configured according to the type of implant to be delivered and according to the location of delivery of the implant. Other forms of delivery apparatuses may be utilized as desired.

The methods and systems disclosed herein may in certain embodiments not be limited to delivery of implants, but may extend to any medical intervention or insertion into a patient's body, which may include performing a medical procedure within the body. The methods and systems disclosed herein may be utilized in general use of a catheter as desired. For example, the handle shown in FIG. 41 and components disclosed therein may comprise a general catheter handle in certain embodiments. Further, the configuration of the delivery apparatus may be modified in other embodiments. For example, for an aortic valve delivery apparatus, the configuration of the implant retention area and other features of the delivery apparatus may be modified.

Figure 42:
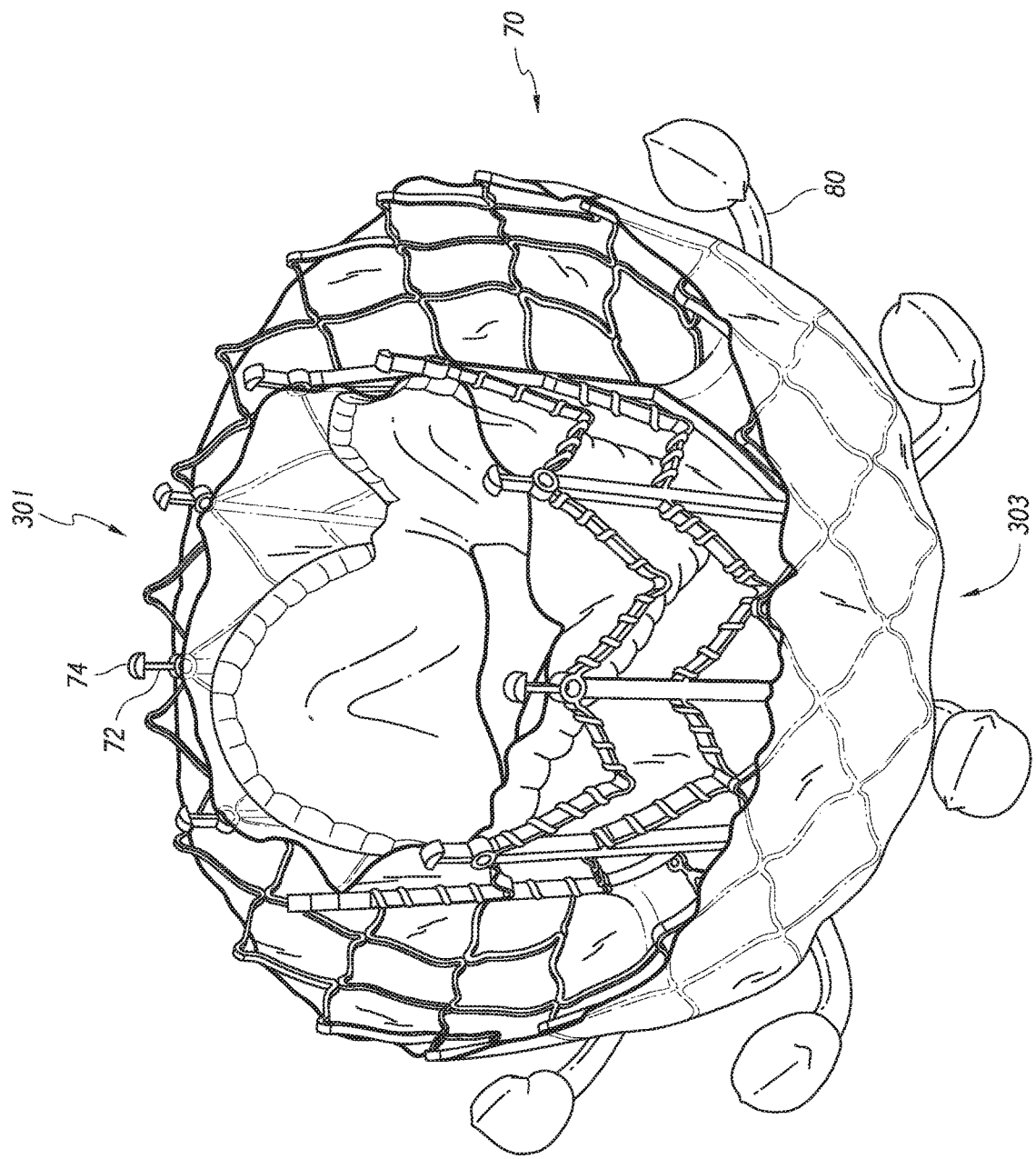
FIG. 42 illustrates a perspective view of an embodiment of an implant.

FIG. 42 illustrates an alternative embodiment of an implant that may be utilized according to embodiments herein. Reference numbering of FIG. 42 is the same as discussed above with respect to FIG. 3A.

With reference next to FIGS. 43-44, an alternative embodiment of an implant 1600 in an expanded configuration is illustrated. The implant 1600 can include an inner frame 1620, an outer frame 1640, a valve body 1660, and one or more skirts, such as an outer skirt 1680 and an inner skirt 1690.

With reference first to the outer frame 1640 illustrated in FIGS. 43-44, the outer frame 1640 can be attached to the inner frame 1620 using any known fasteners and/or techniques. Although the outer frame 1640 is illustrated as a separate component from the inner frame 1620, it is to be understood that the frames 1620, 1640 can be unitarily or monolithically formed.

As shown in the illustrated embodiment, the outer frame 1640 can include an outer frame body 1642. The outer frame body 1642 can have an upper region 1642a, an intermediate region 1642b, and a lower region 1642c. At least a portion of the upper region 1642a of the outer frame body 1642 can be sized and/or shaped to generally match the size and/or shape of an upper region 1622a of the inner frame 1620. As shown in the illustrated embodiment, the upper region 1642a of the outer frame body 1642 can include one or more struts which generally match the size and/or shape of struts of the inner frame 1620. This can locally reinforce a portion of the implant 1600 by effectively increasing the wall thickness of the combined struts.

When in an expanded configuration such as in a fully expanded configuration, the intermediate region 1642b and the lower region 1642c can have a diameter which is larger than the diameter of the upper region 1642a. The upper region 1642a of the outer frame body 1642 can have a decreasing diameter from a lower end to an upper end such that the upper region 1642a is inclined or curved radially inwards towards the longitudinal axis of the implant 1600. Although the outer frame body 1642 has been described and illustrated as being cylindrical or having circular cross-sections, it is to be understood that all or a portion of the outer frame body 1642 can be have a non-circular cross-section such as, but not limited to, a D-shape, an oval or an otherwise ovoid cross-sectional shape.

With continued reference to the outer frame 1600 illustrated in FIG. 43, the outer frame body 1642 can include a plurality of struts with at least some of the struts forming cells 1646a-c. Any number of configurations of struts can be used, such as rings of undulating struts shown forming ellipses, ovals, rounded polygons, and teardrops, but also chevrons, diamonds, curves, and various other shapes.

The upper row of cells 1646a can have an irregular octagonal shape such as a "heart" shape. This additional space can beneficially allow the outer frame 1640 to retain a smaller profile when crimped. The cell 1646a can be formed via a combination of struts. As shown in the illustrated embodiment, the upper portion of cells 1646a can be formed from a set of circumferentially-expansible struts 1648a having a zig-zag or undulating shape forming a repeating "V" shape. The struts 1648a can extend radially outwardly from an upper end to a lower end. These struts can generally match the size and/or shape of struts of the inner frame 1620.

The middle portion of cells 1646a can be formed from a set of struts 1648b extending downwardly from bottom ends of each of the "V" shapes. The struts 1648b can extend radially outwardly from an upper end to a lower end. The portion of the cells 1646a extending upwardly from the bottom end of struts 1648b may be considered to be a substantially non-foreshortening portion of the outer frame 1640.

The lower portion of cells 1646a can be formed from a set of circumferentially-expansible struts 1648c having a zig-zag or undulating shape forming a repeating "V" shape. As shown in the illustrated embodiment, the struts 1648c can incorporate a curvature such that the lower end of struts 1648c extend more parallel with the longitudinal axis than the upper end of the struts 1648c. One or more of the upper ends or tips of the circumferentially-expansible struts 1648c can be a "free" apex which is not connected to a strut. For example, as shown in the illustrated embodiment, every other upper end or tip of circumferentially-expansible struts 1648b is a free apex. However, it is to be understood that other configurations can be used. For example, every upper apex along the upper end can be connected to a strut.

The middle and/or lower rows of cells 1646b-c can have a different shape from the cells 1646a of the first row. The middle row of cells 1646b and the lower row of cells 1646c can have a diamond or generally diamond shape. The diamond or generally diamond shape can be formed via a combination of struts.

The upper portion of cells 1646b can be formed from the set of circumferentially-expansible struts 1648c such that cells 1646b share struts with cells 1646a. The lower portion of cells 1646b can be formed from a set of circumferentially-expansible struts 1648d. As shown in the illustrated embodiment, one or more of the circumferentially-expansible struts 1648d can extend generally in a downward direction generally parallel to the longitudinal axis of the outer frame 1640.

The upper portion of cells 1646c can be formed from the set of circumferentially-expansible struts 1648d such that cells 1646c share struts with cells 1646b. The lower portion of cells 1646c can be formed from a set of circumferentially-expansible struts 1648e. Circumferentially-expansible struts 1648e can extend generally in a downward direction.

As shown in the illustrated embodiment, there can be a row of nine cells 1646a and a row of eighteen cells 1646b-c. While each of the cells 1646a-c are shown as having the same shape as other cells 1646a-c of the same row, it is to be understood that the shapes of cells 1646a-c within a row can differ. Moreover, it is to be understood that any number of rows of cells can be used and any number of cells may be contained in the rows.

As shown in the illustrated embodiment, the outer frame 1600 can include a set of eyelets 1650. The upper set of eyelets 1650 can extend from an upper region 1642a of the outer frame body 1642. As shown, the upper set of eyelets 1650 can extend from an upper portion of cells 1646a, such as the upper apices of cells 1646a. The upper set of eyelets 1650 can be used to attach the outer frame 1640 to the inner frame 1620. For example, in some embodiments, the inner frame 1620 can include one or more eyelets which correspond to the eyelets 1650. In such embodiments, the inner frame 1620 and outer frame 1640 can be attached together via eyelets 1650 and corresponding eyelets on the inner frame 1620. For example, the inner frame 1620 and outer frame 1640 can be sutured together through said eyelets or attached via other means, such as mechanical fasteners (e.g., screws, rivets, and the like).

As shown, the set of eyelets 1650 can include two eyelets extending in series from each "V" shaped strut. This can reduce the likelihood that the outer frame 1640 twists along an axis of the eyelet. However, it is to be understood that some "V" shaped struts may not include an eyelet. Moreover, it is to be understood that a fewer or greater number of eyelets can extend from a "V" shaped strut.

The outer frame 1640 can include a set of locking tabs 1652 extending from at or proximate an upper end of the upper region 1642a. As shown, the locking tabs 1652 can extend upwardly from the set of eyelets 1650. The outer frame 1640 can include twelve locking tabs 1652, however, it is to be understood that a greater number or lesser number of locking tabs can be used. The locking tabs 1652 can include a longitudinally-extending strut 1652a. At an upper end of the strut 1652a, the locking tab 1652 can include an enlarged head 1652b. As shown, the enlarged head 1652b can have a semi-circular or semi-elliptical shape forming a "mushroom" shape with the strut 1652a. The locking tab 1652 can include an eyelet 1652c which can be positioned through the enlarged head 1652b. It is to be understood that the locking tab 1652 can include an eyelet at other locations, or can include more than a single eyelet.

The locking tab 1652 can be advantageously used with multiple types of delivery systems. For example, the shape of the struts 1652a and the enlarged head 1652b can be used to secure the outer frame 1640 to a "slot" based delivery system, such as the inner retention member 40 described above. The eyelets 1652c and/or eyelets 1650 can be used to secure the outer frame 1640 to a "tether" based delivery system such as those which utilize sutures, wires, or fingers to control delivery of the outer frame 1640 and the implant 1600. This can advantageously facilitate recapture and repositioning of the outer frame 1640 and the implant 1600 in situ.

The outer frame 1640, such as the outer frame body 1642 can be used to attach or secure the implant 1600 to a native valve, such as a native mitral valve. For example, the intermediate region 1642b of the outer frame body 1642 and/or the outer anchoring feature 1644 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1642 can be sized and positioned relative to the inner frame anchoring feature 1624 such that tissue of the body cavity positioned between the outer frame body 1642 and the inner frame anchoring feature 1624, such as native valve leaflets and/or a native valve annulus, can be engaged or pinched to further secure the implant 1600 to the tissue. As shown, the inner frame anchoring feature 1624 includes nine anchors; however, it is to be understood that a fewer or greater number of anchors can be used. In some embodiments, the number of individual anchors can be chosen as a multiple of the number of commissures for the valve body 1660. For example, for a valve body 1660 have three commissures, the inner frame anchoring feature 1624 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. In some embodiments, the number of individual anchors does not correspond to the number of commissures of the valve body 1660.

With continued reference to the prosthesis 1600 illustrated in FIGS. 43-44, the valve body 1660 is attached to the inner frame 1620 within an interior of the inner frame body 1622. The valve body 1660 functions as a one-way valve to allow blood flow in a first direction through the valve body 1660 and inhibit blood flow in a second direction through the valve body 1660.

The valve body 1660 can include a plurality of valve leaflets 1662, for example three leaflets 1662, which are joined at commissures. The valve body 1660 can include one or more intermediate components 1664. The intermediate components 1664 can be positioned between a portion of, or the entirety of, the leaflets 1662 and the inner frame 1620 such that at least a portion of the leaflets 1642 are coupled to the frame 1620 via the intermediate component 1664. In this manner, a portion of, or the entirety of, the portion of the valve leaflets 1662 at the commissures and/or an arcuate edge of the valve leaflets 1662 are not directly coupled or attached to the inner frame 1620 and are indirectly coupled or "float" within the inner frame 1620.

With reference next to the outer skirt 1680 illustrated in FIG. 43, the outer skirt 1680 can be attached to the inner frame 1620 and/or outer frame 1640. As shown, the outer skirt 1680 can be positioned around and secured to a portion of, or the entirety of, the exterior of the outer frame 1640. The inner skirt 1690 can be attached to the valve body 1660 and the outer skirt 1680. As shown in FIG. 44, a first end of the inner skirt 1690 can be coupled to the valve body 1660 along portions of the valve body 1660 which are proximate the inner frame 1620. A second end of the inner skirt 1690 can be attached to the lower region of the outer skirt 1680. In so doing, a smooth surface can be formed along under each of the leaflets. This can beneficially enhance hemodynamics by allowing blood to more freely circulate and reducing areas of stagnation.

Although the implant 1600 has been described as including an inner frame 1620, an outer frame 1640, a valve body 1660, and skirts 1680, 1690, it is to be understood that the implant 1600 need not include all components. For example, in some embodiments, the implant 1600 can include the inner frame 1620, the outer frame 1640, and the valve body 1660 while omitting the skirt 1680. Moreover, although the components of the implant 1600 have been described and illustrated as separate components, it is to be understood that one or more components of the implant 1600 can be integrally or monolithically formed. For example, in some embodiments, the inner frame 1620 and the outer frame 1640 can be integrally or monolithically formed as a single component.

Figure 45:
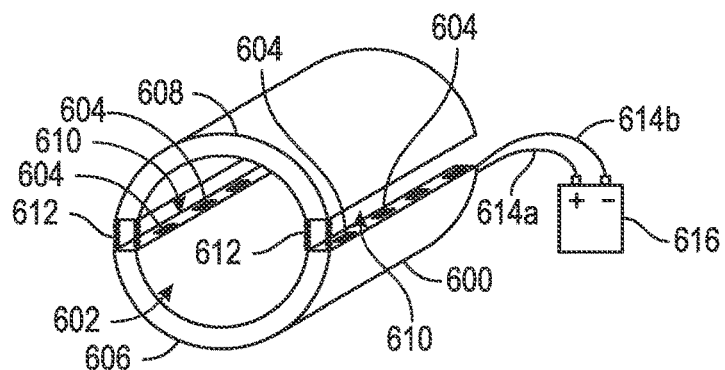
FIG. 45 illustrates a perspective view of a capsule of a delivery system.

FIGS. 45-48 illustrate embodiments in which at least one electromagnet is utilized that is configured to attract or repel a portion of a capsule of a delivery apparatus to vary a size of the capsule. Referring to FIG. 45, the capsule 600 may be configured similarly as the capsule 106 or any other capsule disclosed herein. The capsule 600 may surround an implant retention area 602 that may be configured similarly as implant retention area 16 or any other implant retention area disclosed herein. The capsule 600 may be a part of an elongate shaft of a delivery apparatus, which may be configured in a similar manner as disclosed herein. The implant retention area 602 may be configured to retain an implant, which may comprise the implant 70 or another form of implant as disclosed herein.

At least one electromagnet 604 may be utilized to vary a size of the capsule. As shown in FIG. 45, a plurality of electromagnets 604 may be utilized, or in other embodiments a single electromagnet 604 may be utilized. The electromagnets 604 may be coupled to and positioned on a first portion 606 of a capsule 600 and may be configured to attract or repel a second portion 608 of the capsule 600. The first portion 606 as shown in FIG. 45 may comprise a side wall of the capsule 600 that is configured to surround the implant 70 within the implant retention area 602. The second portion 608 may similarly comprise a side wall of the capsule 600 that is configured to surround the implant 70. The side walls may be configured to apply a compressive force to the implant 70 while the implant 70 is retained within the implant retention area 602. The first portion 606 and second portion 608 may comprise halves of the capsule 600 and may extend along the axial length of the capsule 600. In other embodiments, other configurations of portions of the capsule 600 may be utilized. Further, other positions of the one or more electromagnets 604 may be utilized. For example, the one or more electromagnets 604 may be positioned on another assembly of the delivery apparatus such as the nose cone assembly 31, the inner assembly 18, the mid shaft assembly 21, among other locations. The electromagnets 604 as shown in FIG. 45 are positioned on the outer sheath assembly 22, although other positions may be utilized to vary a size of the capsule 600.

The portions 606, 608 may be separated from each other by a gap 610 between the portions 606, 608. The gap 610 may be an open gap 610 or may be a filled gap 610 that is filled with material, for example, material that may be compressed if desired. The gap 610 may extend along the axial length of the capsule 600 as shown in FIG. 45 or may have other configurations in other embodiments as desired. The separation between the edges of the portions 606, 608 provided by the gap 610 may allow the portions 606, 608 to move relative to each other to increase and decrease the size of the gap 610 and accordingly vary the size of the capsule 600.

A biasing body 612 may be utilized that may bias the portions 606, 608 towards each other or away from each other. The biasing body 612 may be configured to apply a biasing force to the portions 606, 608. Such a biasing force may draw the portions 606, 608 towards each other or away from each other as desired. The biasing force may counteract the direction of the force to be applied by the at least one electromagnet 604. For example, in an embodiment in which the at least one electromagnet 604 attracts the portions 606, 608 together, the biasing body 612 may move the portions 606, 608 away from each other. In an embodiment in which the at least one electromagnet 604 repels the portions 606, 608, the biasing body 612 may move the portions 606, 608 towards each other. The biasing body 612 may comprise an elastic body that is configured to resist a compression or expansion of the body 612. For example, as the body 612 is compressed, the body 612 may provide a resistive expansion force, and as the body 612 is expanded, the body 612 may provide a resistive compressive force. The body 612 may be positioned within the gap 610 or may be positioned outside of the gap 610 as desired. For example, the body 612 may comprise a sheath placed over the gap 610 or the outer surface of the capsule 600 as desired.

The one or more electromagnets 604 may be positioned as desired to attract or repel the portion of the capsule 600 to vary the size of the capsule 600. The one or more electromagnets 604 may be coupled to electrical conduits 614a, b that may extend along the length of the elongate shaft and may couple to a power source 616 that may be configured similarly as the power source 538 shown in FIG. 10 or any other power source disclosed herein. The power source 616 may be configured to provide electrical energy to the at least one electromagnet 604. The power source 616 may be configured to pass a current through the electrical conduits 614a, b and through the one or more electromagnets 604 to actuate the electromagnets 604 and cause the electromagnets 604 to provide an attractive or repulsive force. The power source 616 may be configured to reverse the direction of current to vary from an attractive or repulsive force as desired. The power source 616 may also be able to vary the amount of current through the one or more electromagnets 604 to vary the strength of the attractive or repulsive force.

The one or more electromagnets 604 may be configured to apply a magnetic force to magnetically responsive materials in the capsule 600 (for example the portion of the capsule 600 that does not include the electromagnets 604 such as the second portion 608 shown in FIG. 45). The magnetically responsive material may be a metal or other form of magnetically responsive material that may be coupled to the capsule 600 at a desired location. In other embodiments, the electromagnets 604 may be configured to apply a magnetic force to other electromagnets 604 or magnetic materials.

The one or more electromagnets 604 may be utilized to vary a radial size of the capsule 600. The diameter of the implant retention area 602 may vary, and the inner and outer diameter of the capsule 600 may vary as well. The variation in the size of the capsule 600 may allow for a lower profile size of the capsule 600 at a desired time, and a larger profile size of the capsule 600 at another desired time. For example, a lower profile size of the capsule 600 may be desired upon passage through the vasculature of the patient's body. A larger profile size of the capsule 600 may be desired to enhance ease of passage of the implant 70 into and out of the capsule 600 at a desired time. For example, upon entry of the implant 70 into the capsule 600 during a loading procedure, a larger sized implant retention area 602 and capsule 600 may be desired. Further, upon deployment of the implant 70 from the capsule, for example in a procedure as shown in FIGS. 28-30, a larger sized implant retention area 602 and capsule 600 may be desired. A larger sized implant retention area 602 and capsule 600 may reduce friction upon the implant 70 and capsule 600 upon loading and deployment of the implant 70. As such, a reduced force may be applied to the capsule 600 upon retraction of the capsule 600 to deploy the implant 70. The use of the one or more electromagnets 604 may allow a user to selectively vary a size of the capsule 600.

Figure 46:
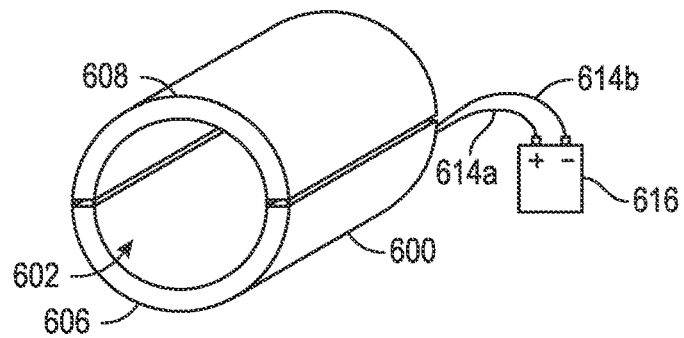
FIG. 46 illustrates a perspective view of the capsule of the delivery system shown in FIG. 45.

The capsule 600 may be biased to have a larger size, with the one or more electromagnets 604 utilized to decrease the size of the capsule 600. For example, as shown in FIG. 45, the biasing body 612 may apply a biasing force to the portions 606, 608 to increase the radial size of the capsule 600. The one or more electromagnets 604 may then be actuated to attract the portion 606 to the portion 608 thus overcoming the biasing force and closing the gap 610. The one or more electromagnets 604 may attract the portion 608 to decrease the radial size of the capsule 600. FIG. 46 illustrates the capsule 600 having a decreased radial size than shown in FIG. 45. In such an embodiment, the capsule 600 may be advanced to a desired location within the patient's body with the capsule 600 having the decreased radial size. At a desired time for deployment of the implant 70 positioned within the capsule 600, the one or more electromagnets 604 may be deenergized and the biasing body 612 may press the portions 606, 608 apart from each other to increase the radial size of the capsule 600. The implant 70 accordingly may be deployed from the implant retention area 602 with a reduced friction force with the capsule 600. The one or more electromagnets 604 may be reenergized after deployment of the implant 70 to decrease the radial size of the capsule 600 for withdrawal of the capsule 600 and the delivery apparatus from the patient's body.

In embodiments, the biasing body 612 may be configured to decrease the radial size of the capsule 600, with the one or more electromagnets 604 applying a repulsive force to repel a portion of the capsule 600 to increase the radial size of the capsule 600. In such an embodiment, the one or more electromagnets 604 may be energized at the desired time to overcome the force of the biasing body 612 and increase the radial size of the capsule 600.

In embodiments, a biasing body may be excluded. For example, the one or more electromagnets 604 may apply an attractive or repulsive force alternatively to vary a size of the capsule 600. The one or more electromagnets 604 may be configured to apply an attractive force to keep the capsule 600 in a low profile configuration until the desired time. The one or more electromagnets 604 may be configured to then apply a repulsive force to increase the radial size of the capsule at a desired time. The direction of current through the electrical conduits 614a, b may be alternated to vary the force between attractive and repulsive. The amount of current may also be controlled to vary the strength of the attractive and repulsive force and set the size of the capsule to a desired size. In embodiments, a biasing body may be excluded and the one or more electromagnets 604 may only be configured to provide an attractive force. An expansion force provided by the implant 70 within the implant retention area 602 may cause the size of the capsule 600 to increase upon the attractive force by the one or more electromagnets 604 being ceased. Other configurations utilizing the one or more electromagnets 604 may be provided.

Figure 47:
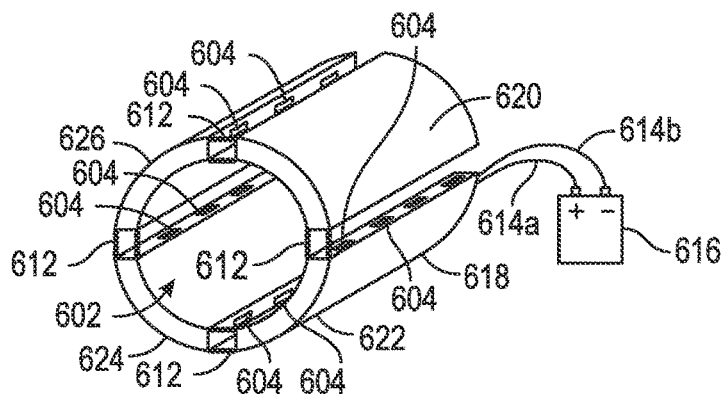
FIG. 47 illustrates a perspective view of a capsule of a delivery system.
Figure 48:
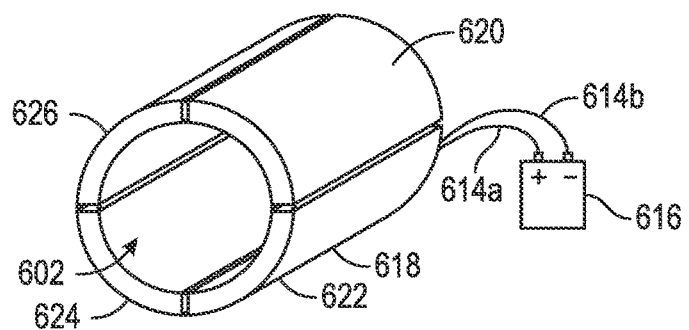
FIG. 48 illustrates a perspective view of the capsule of the delivery system shown in FIG. 47.

FIGS. 47 and 48 illustrate an embodiment in which the capsule may be split into multiple portions, with one or more electromagnets 604 configured to attract or repel a portion of a capsule of a delivery apparatus to vary a size of the capsule. The capsule 618 may include portions 620, 622, 624, 626 that are separated by gaps and that form side walls of the capsule 618, similar to the portions 606, 608. The position and greater number of gaps, however, may increase the overall size variation of the capsule 618. Further, the size variation may be more uniform about the capsule 618 due to the symmetrically spaced placement of the portions 620, 622, 624, 626. The one or more electromagnets 604 may be configured to vary the size of the capsule 618 in a similar manner as discussed in regard to FIGS. 45 and 46.

The electromagnets may be utilized with any embodiment of delivery system disclosed herein. The electromagnets may be controlled by a processor, as disclosed herein, which may operate to actuate the electromagnets and thus vary the size of the capsule as desired. Such operation may occur in response to a user's input, via a control device or the like, or the processor may automatically actuate the electromagnets as desired. For example, the processor may actuate the electromagnets in response to a sensor reading (for example one of the sensors as disclosed herein), or in response to a program, indicating that the size of the capsule should be varied. The processor may be configured to automatically vary the size of the capsule and deploy the implant.

The power supply for the electromagnets may be integrated with a controller, for example a controller 530 as shown in FIG. 18. The electrical conduits for the electromagnets may extend to the controller. The processor may be configured to control the power supply to control the electromagnets.

A method that may utilize the embodiments of FIGS. 45-48 may include deploying an elongate shaft to a location within a patient's body, the elongate shaft including a capsule surrounding an implant retention area retaining an implant for implantation within the patient's body. The at least one electromagnet may be utilized to attract or repel a portion of the capsule to vary of a size of the capsule within the patient's body. A radial size of the capsule may be increased utilizing the at least one electromagnet. For example, the at least one electromagnet may be energized to repel a portion of the capsule or the at least one electromagnet may be deenergized to allow a biasing body to increase the size of the capsule. The implant may be deployed from the capsule with the capsule having the increased radial size. In addition, the capsule may have its size increased to recapture a portion of the implant. Further, the implant may be inserted into the capsule with the capsule having the increased radial size. The implant may be inserted into the capsule during loading of the implant into the capsule. The size of the capsule may be dynamically adjustable.

FIGS. 49-59 illustrate embodiments including electrically detachable couplers that are configured to couple to an implant and to detach from at least a portion of the implant. FIGS. 49-55 illustrate embodiments utilizing an electrolytically detachable coupler.

Figure 49:
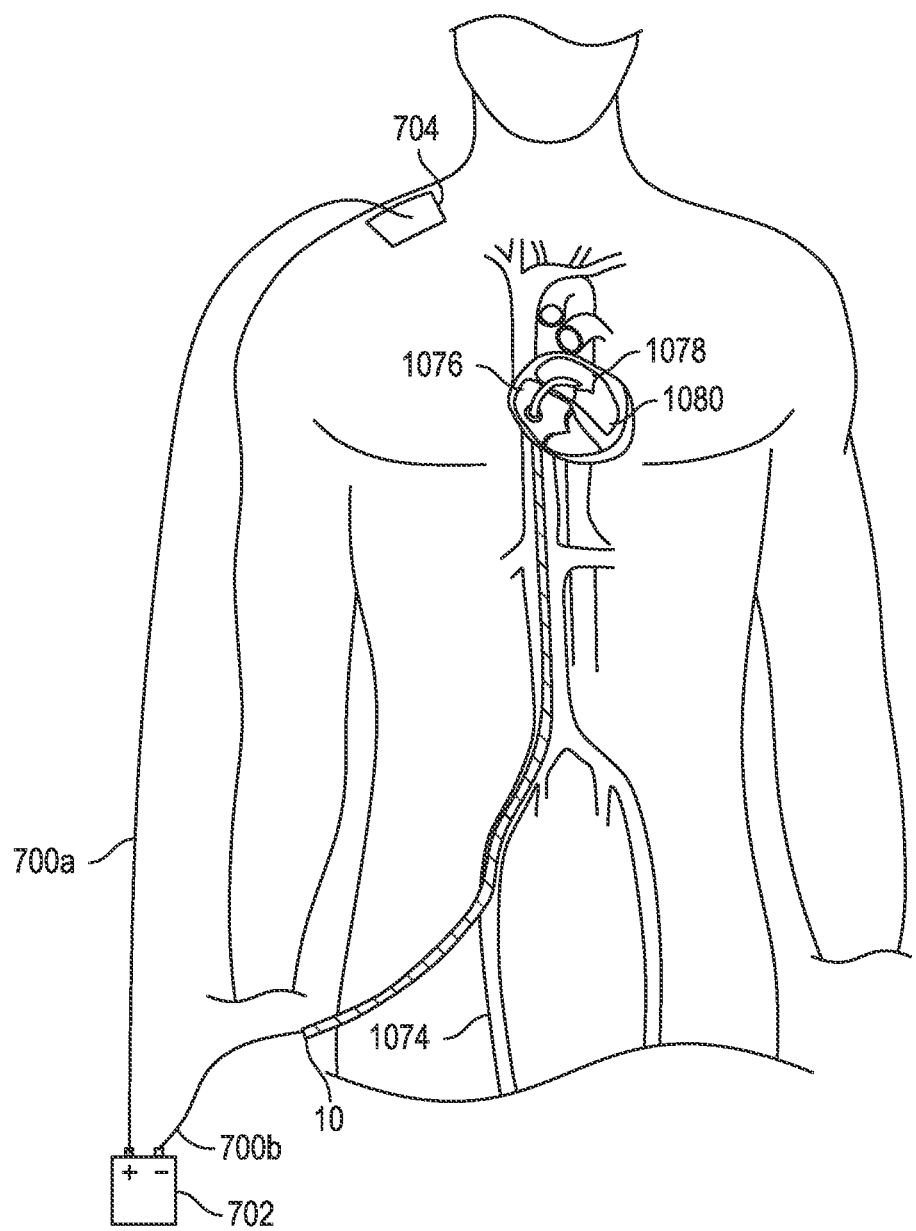
FIG. 49 illustrates a schematic view of a delivery system entering a patient's body.

Referring to FIG. 49, an electrolytically detachable coupler may utilize an electrical circuit to electrolytically erode the electrolytically detachable coupler. The electrical circuit may include electrical conduits 700a, b that may be coupled to a power supply 702. The electrical conduits 700a, b may couple to electrical terminals. The blood of the patient and other fluids or materials may be utilized as a conduit for the electrical circuit to electrically couple the electrical terminals. For example, as shown in FIG. 49, an electrical terminal 704 may be configured to be positioned on a portion of the patient's body. The electrical terminal 704 may be configured as an electrode that is coupled to a patch that is coupled to the patient's body. The patch may be positioned on the patient's skin, and may be near the shoulder or otherwise may be positioned on the chest or elsewhere on the patient. In other embodiments, other forms of electrical terminals may be utilized such as clips or other devices for coupling to the patient's body. The electrical terminal 704 may couple to the electrical conduit 700a that is coupled to the power supply 702. The electrical conduit 700b may be coupled to the power supply 702 and may extend along the elongate shaft of the delivery apparatus to reach the electrical terminal as part of the electrolytically detachable coupler. The electrolytically detachable coupler may comprise a first portion of an electrical circuit, and the electrical terminal 704 may form a second portion of the electrical circuit. The power supply 702 may electrically couple the first portion of the electrical circuit to the second portion of the electrical circuit and may be configured to pass an electrical current between the first portion and the second portion.

Figure 50:
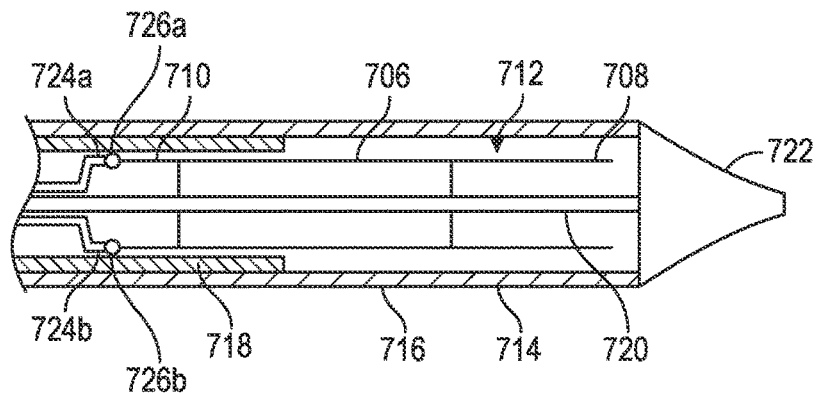
FIG. 50 illustrates a schematic cross-sectional view of an implant retention area of an elongate shaft of a delivery system.

FIG. 50, for example, illustrates a schematic side cross sectional view of the implant retention area of an elongate shaft, including an implant 706 positioned therein. The implant 706 may be configured similarly as the implant 70 or another form of implant as disclosed herein. The implant 706 may include distal anchors 708 and proximal anchors 710 and may be a self-expanding implant. The implant 706 as shown in FIG. 50 may be in a compressed state within the implant retention area 712.

A capsule 714 may surround the implant 706 within the implant retention area 712 and may be configured similarly as the capsule 106 or any other capsule disclosed herein. The capsule 714 may be formed of an outer sheath 716 and an outer retention ring 718 that may be configured similarly as the respective outer sheath and outer retention ring 42 otherwise disclosed herein. A nose cone shaft 720 may couple to a nose cone 722 that may be configured similarly as the nose cone shaft 27 and nose cone 28 respectively, or any other nose cone shaft or nose cone disclosed herein.

Figure 51:
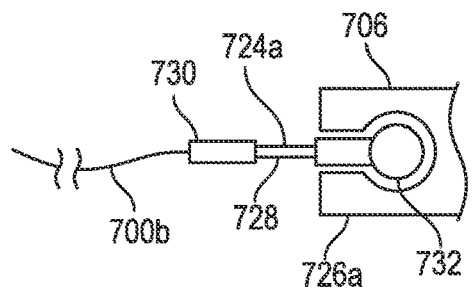
FIG. 51 illustrates an enlarged view of a coupling between an electrolytically detachable coupler and an implant.

The delivery apparatus shown in FIG. 50 may include an electrolytically detachable coupler 724a, b that couples to the implant 706. The electrolytically detachable coupler 724a, b may couple to a proximal end of the implant 706 as shown in FIG. 50. FIG. 51 provides an enlarged view of the point of connection between the electrolytically detachable coupler 724a and the implant 706 (at which reference number 726a points to in FIG. 50). The implant 706 may include a proximal end coupler 726a that may be positioned in a similar location as the mushroom-shaped tabs 74 shown in FIG. 3A. As shown in FIG. 51, the proximal end coupler 726a may include a cavity or other form of coupler that receives the electrolytically detachable coupler 724a. The electrolytically detachable coupler 724a may form a rigid connection with the proximal end coupler 726a. The electrolytically detachable coupler 724a may include an exposed electrical terminal 728 that is exposed and in contact with the patient's fluid during deployment of the implant 706. The exposed electrical terminal 728 may be electrically connected to the electrical conduit 700b, which may extend along the elongate shaft to the power supply 702 as shown in FIG. 49. Portions adjacent to the exposed electrical terminal 728 may be electrically insulated, for example an electrically insulated portion 730 may be proximal the exposed electrical terminal 728 and another electrically insulated portion 732 may be positioned distal of the exposed electrical terminal 728. As such, flow of current from the electrical conduit 700b may be prevented from reaching the implant 706. In other embodiments, the implant 706 may be electrically insulated.

The electrolytically detachable coupler 724a may be configured such that as current is passed through the electrical conduit 700b with the power supply 702, the exposed electrical terminal 728 may be in electrical contact with the patient's fluid (which may be blood during delivery of the implant to a portion of the patient's heart) and may utilize the fluid to complete the electrical circuit with the terminal 704. The exposed electrical terminal 728 may disintegrate due to electrolytic erosion and may detach from the portion of the implant 706.

Figure 52:
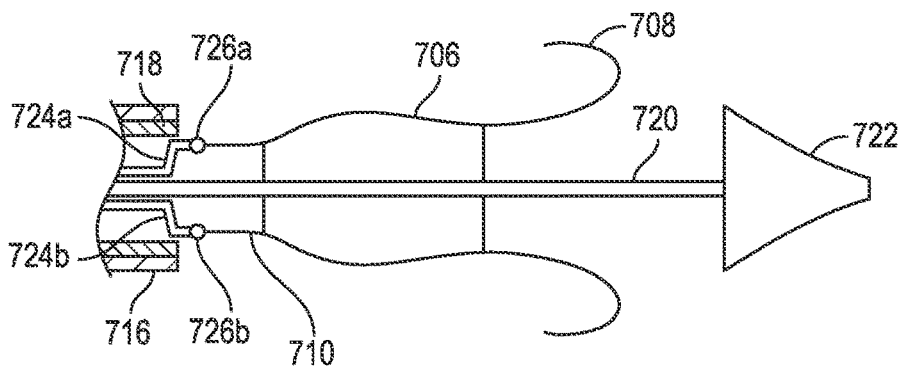
FIG. 52 illustrates a schematic cross-sectional view of the implant retention area shown in FIG. 50.
Figure 53:
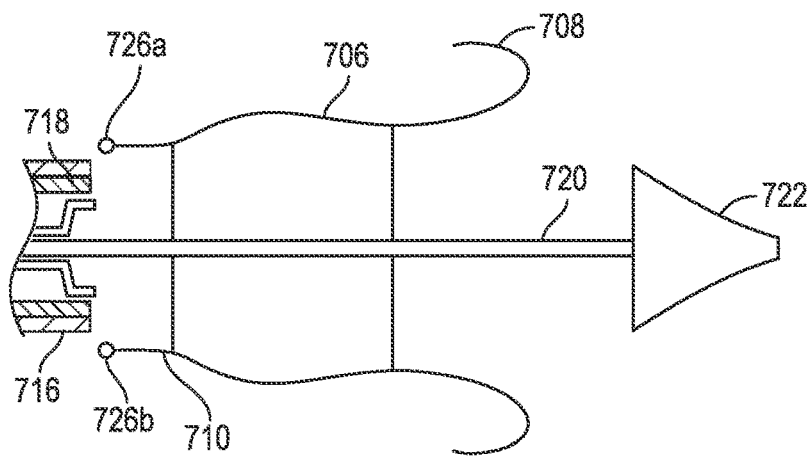
FIG. 53 illustrates a schematic cross-sectional view of the implant retention area shown in FIG. 50.

For example, as shown in FIG. 52, the capsule 714 may be placed in the desired location within the patient's body and the outer sheath 716 and outer retention ring 718 may be retracted to expose the implant 706. The implant 706 may begin a process of expansion yet may remain coupled to the electrolytically detachable coupler 724a, b. Upon the implant 706 being positioned in the desired location, the power supply 702 may be powered to pass a current through the electrical conduits 700a, b. The electrolytically detachable coupler 724a, b may disintegrate due to electrolytic erosion and thus detach from the implant 706 as shown in FIG. 53. The implant 706 may then be left deployed in position within the desired location in the patient's body, for example, the implant 706 may be left deployed to the patient's heart valve. The delivery apparatus may then be removed from the patient's body as disclosed herein.

The electrolytically detachable coupler 724a, b may be disintegrated after assessing implant anchoring and hemodynamic stability. The electrolytically detachable coupler 724a, b may provide a strong, rigid attachment that may be capable of withstanding forces involved in repositioning and resheathing an implant if desired. Further, the use of an electrolytically detachable coupler 724a, b may reduce the overall length and size of the deployment mechanism.

Figure 54:
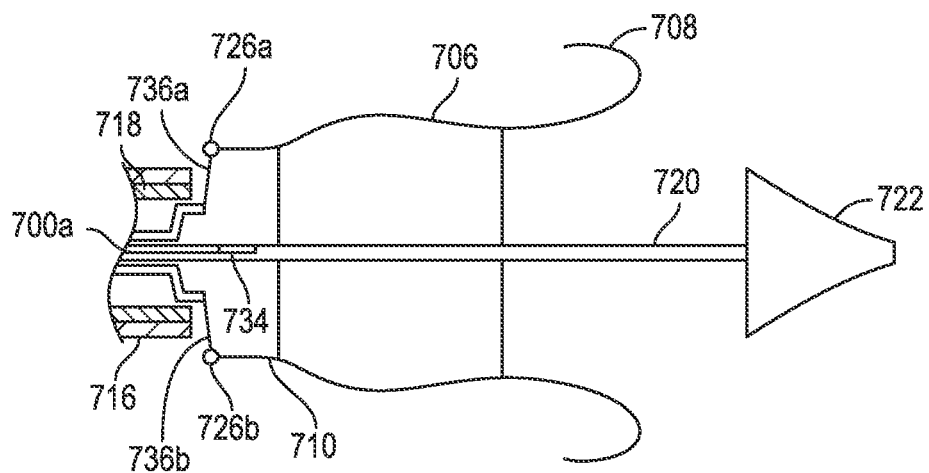
FIG. 54 illustrates a schematic cross-sectional view of an implant retention area of a delivery system.

FIG. 54 illustrates a variation of the embodiment shown in FIGS. 50-53, in which the electrical conduit 700a may be coupled to an electrical terminal 734 that is positioned on the elongate shaft. For example, as shown in FIG. 54, the electrical terminal 734 may be positioned on the nose cone shaft 720, although in other embodiments other locations for the electrical terminal 734 may be utilized. For example, the electrical terminal 734 may be positioned on a portion of an inner assembly, rail assembly, mid shaft assembly, or outer sheath assembly, as desired. The electrical terminal 734 may couple to the electrical conduit 700a to form a return path for the electrical conduit 700b that passes to the electrolytically detachable coupler 736a, b. As such, in such an embodiment, the electrical terminal 704 shown in FIG. 49 does not need to be used, because an electrical terminal 734 on the elongate shaft forms a return path for the electrical circuit. The electrolytically detachable coupler 736a, b may comprise a first portion of an electrical circuit, and the electrical terminal 734 may be coupled to the elongate shaft and form a second portion of the electrical circuit. Further, as shown in FIG. 54, the electrolytically detachable coupler 736a, b may be in the form of tethers that extend to the proximal ends of the implant 706 and couple to the implant 706. As such, as the outer sheath 716 and outer retention ring 718 are retracted, the implant 706 may deploy to its full expanded size. The electrolytically detachable coupler 736a, b, however, may remain coupled to the implant 706 until it is desired for the implant 706 to detach from the elongate shaft. The power supply may then be energized to pass current through the electrical conduits to disintegrate the electrolytically detachable coupler 736a, b due to electrolytic erosion.

Figure 55:
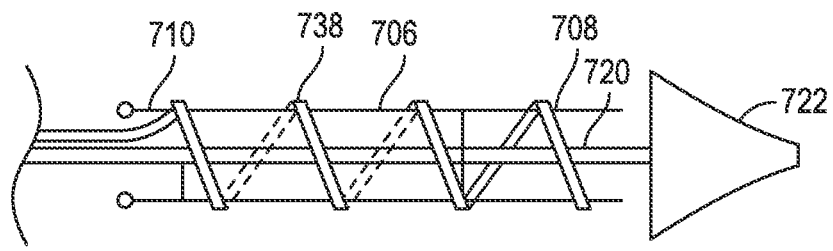
FIG. 55 illustrates a schematic cross-sectional view of an implant retention area of a delivery system.

In certain embodiments, the electrolytically detachable coupler may be utilized such that one or more of the outer sheath 716 or the outer retention ring 718 does not need to be utilized. For example, the electrolytically detachable coupler may retain the implant 706 with such force that expansion of the implant 706 is restrained by the electrolytically detachable coupler. FIG. 55, for example, illustrates an embodiment in which an electrolytically detachable coupler 738 extends over an outer surface of the implant 706. The electrolytically detachable coupler 738 may comprise a coil that extends over the implant 706 as shown in FIG. 55 or may have a variety of other shapes as desired (e.g. a sheath, longitudinal slats, a mesh, among others). The electrolytically detachable coupler 738, however, may operate in a similar manner as discussed regarding the other electrolytically detachable couplers disclosed herein, namely, the electrolytically detachable coupler 738 may disintegrate due to electrolytic erosion and may detach from the portion of the implant 706. The implant 706 may then expand upon disintegration of the electrolytically detachable coupler 738. A variety of other configurations of electrolytically detachable couplers may be utilized as desired.

Figure 56:
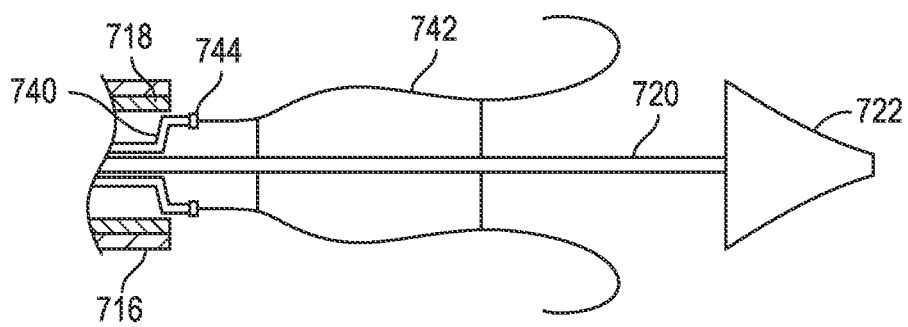
FIG. 56 illustrates a schematic cross-sectional view of an implant retention area of a delivery system.
Figure 57:
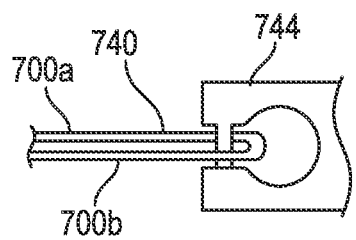
FIG. 57 illustrates an enlarged view of a coupling between an electrically detachable coupler and an implant.

FIGS. 56-57 illustrate an embodiment in which an electrically detachable coupler 740 may be utilized that disintegrates due to heat caused by an electrical current passed through the electrically detachable coupler 740. For example, electrical conduits, similar to the conduits 700a, 700b, may be coupled to a power supply 702 and may pass a current through the electrically detachable coupler 740. The electrically detachable coupler 740 may be made of a material that disintegrates due to the heat energy provided by the passage of current through the electrically detachable coupler 740, working in a similar manner as a fuse or the like. The electrically detachable coupler 740 may disintegrate at a desired time to detach from the implant 742. The implant 742 may be configured similarly as the implant 70 or any other implant disclosed herein.

The electrically detachable coupler 740 may couple to the implant 70 in a manner shown in the enlarged view of FIG. 57 (at which reference number 744 points to in FIG. 56). The electrically detachable coupler 740 may comprise a loop passing around a coupler 744 on a portion of the implant 742 (for example, a proximal end coupler of the implant 742 as shown in FIG. 57). The loop may couple to the conduits 700a, 700b, and as current is passed through the conduits 700a, 700b and the loop, the electrically detachable coupler 740 may disintegrate due to heat and may detach from the implant 742. The conduit 700a may comprise a first portion of an electrical circuit coupled to a first portion of the electrically detachable coupler 740 and the conduit 700b may comprise a second portion of an electrical circuit coupled to a second portion of the electrically detachable coupler 740 (with the first and second portions of the electrically detachable coupler 740 comprising parts of the loop). The conduits 700a, 700b may both extend along the elongate shaft. Other configurations of couplers 740, including other locations of coupling, may be utilized as desired.

Figure 58:
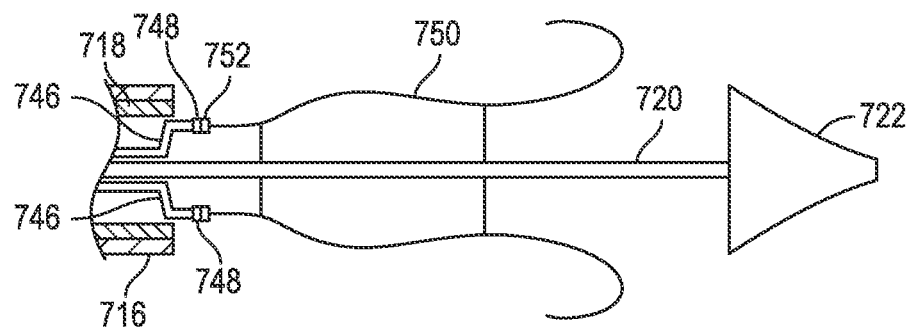
FIG. 58 illustrates a schematic cross-sectional view of an implant retention area of a delivery system.
Figure 59:
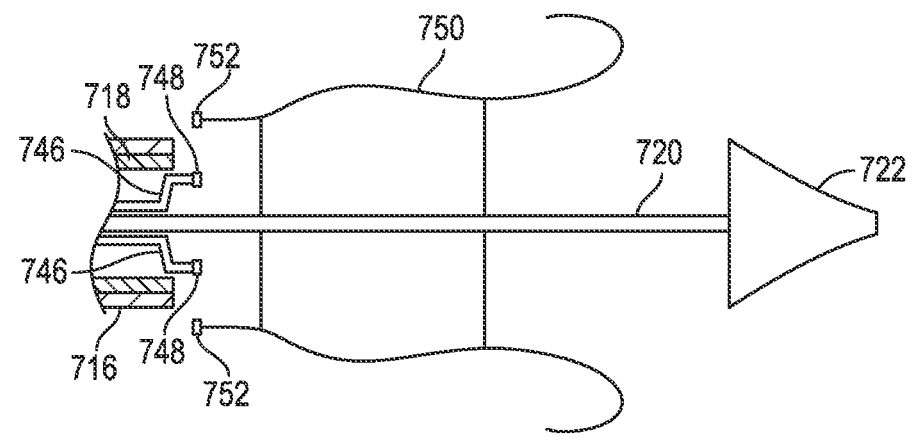
FIG. 59 illustrates a schematic cross-sectional view of the implant retention area shown in FIG. 58.

FIGS. 58-59 illustrate an embodiment of an electrically detachable coupler 746 including one or more electromagnets 748. The electromagnets 748 may be configured to magnetically attract a portion of an implant 750, which may be configured similarly as the implant 70, yet may include magnetically responsive materials 752 that couple to the electromagnets 748. The one or more electromagnets 748 may be coupled to electrical conduits that may be configured similarly as the conduits 700a, 700b and that extend along the elongate shaft. As shown in FIG. 59, upon deactivation of power to the one or more electromagnets 748, the electrically detachable coupler 746 may detach from the implant 750.

The electrically detachable couplers disclosed herein may be utilized with any embodiment of delivery system disclosed herein. The electrically detachable couplers, for example, may be utilized with a delivery apparatus having an elongate shaft. The elongate shaft may include a rail shaft configured to be steerable and a shaft configured to move relative to the rail shaft. The shaft may be coupled to the electrically detachable coupler. The elongate shaft in embodiments may include an outer sheath having an outer lumen and a proximal end and a distal end, with at least a portion of the outer sheath surrounding the implant retention area, and wherein the shaft is positioned within the outer lumen and the rail shaft is positioned within the outer lumen. The outer sheath may be configured to retract relative to the shaft to uncover at least a portion of the implant. The electrically detachable couplers may be utilized in lieu of, and in the same position as, the inner retention ring 40 as shown in FIGS. 2A-2C for example.

The electrically detachable couplers may be controlled by a processor, as disclosed herein, which may operate to actuate the electrically detachable couplers and thus detach at least a portion of the implant from the electrically detachable couplers. Such operation may occur in response to a user's input, via a control device or the like, or the processor may automatically actuate the electrically detachable couplers as desired. For example, the processor may actuate the electrically detachable couplers in response to a sensor reading (for example one of the sensors as disclosed herein), or in response to a program, indicating that the electrically detachable couplers are to be actuated. The processor may be configured to automatically actuate the electrically detachable couplers and deploy the implant.

The power supply for the electrically detachable couplers may be integrated with a controller, for example a controller 530 as shown in FIG. 18. The electrical conduits for the electrically detachable couplers may extend to the controller. The processor may be configured to control the power supply to control the electrically detachable couplers.

A method that may utilize the embodiments of FIGS. 49-59 may include extending a delivery apparatus within a portion of a patient's body to deliver an implant to a body location. At least a portion of the implant may be detached from an electrically detachable coupler within the patient's body. The implant may be any form of implant disclosed herein, including a prosthetic replacement heart valve, including an expandable prosthetic replacement heart valve. The implant may be a self-expanding prosthetic replacement heart valve, and may be a prosthetic mitral valve. Other forms of implants (including implants for repair or replacement of a heart valve) may be utilized as desired. The electrically detachable coupler may retain at least a portion of the expandable prosthetic replacement heart valve in a compressed state. The electrically detachable coupler may be coupled to a proximal end of the expandable prosthetic replacement heart valve. Detaching at least the portion of the implant from the electrically detachable coupler may allow the portion of the implant to expand. The implant may be deployed to the body location as disclosed herein.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally,"

and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method of advancing a prosthetic replacement heart valve through a patient's vasculature in an atraumatic manner, the method comprising:
    advancing a guide wire through the patient's vasculature and into a heart chamber;
    advancing an elongate shaft of a catheter through the patient's vasculature over the guide wire to deliver the prosthetic replacement heart valve to a native heart valve, the prosthetic replacement heart valve being disposed along a distal end portion of the elongate shaft, the catheter including at least one motor for deflecting the distal end portion of the elongate shaft of the catheter within the patient's vasculature with one or more pull wires during advancement through the patient's vasculature for reducing contact with an inner wall of a blood vessel, wherein one or more proximity sensors are positioned along a nose cone for sensing a lateral distance between the nose cone and the inner wall of the blood vessel, wherein the nose cone has a tapered shape and is disposed distal to the elongate shaft during advancement;
    providing, with a processor, control of the at least one motor to deflect the distal end portion of the elongate shaft of the catheter with the one or more pull wires while continuing to advance the elongate shaft through the patient's vasculature for steering the elongate shaft through the patient's vasculature in an atraumatic manner, wherein the at least one motor deflects the distal end portion with the one or more pull wires based on signals from the one or more proximity sensors of the lateral distance between the nose cone and the inner wall of the blood vessel while the elongate shaft of the catheter continues to be advanced, the signals provided as feedback to the processor; and
    radially expanding the prosthetic replacement heart valve within the native heart valve to deploy the prosthetic replacement heart valve to the native heart valve from the distal end portion of the elongate shaft of the catheter.

2. The method of claim 1, wherein the processor provides an output that is provided as an indicator on an output device,
    wherein the output device comprises one or more of a display screen, a light, a speaker, or a haptic device, and
    wherein the indicator indicates a condition of the catheter or a condition of the patient's body.

3. The method of claim 1, wherein the processor provides an output comprising a log of data for an implantation procedure with the catheter, and further comprising storing the log of data in a memory.

4. The method of claim 1, wherein the catheter further comprises one or more sensors on the elongate shaft that sense a condition of the patient's body comprising one or more of a blood pressure within the patient's body or a blood flow within the patient's body, and
    wherein the processor controls the at least one motor to deploy the prosthetic replacement heart valve to the native heart valve.

5. The method of claim 1, wherein the catheter includes a handle coupled to a proximal end of the elongate shaft, and
    wherein the catheter comprises a self-contained unit including the processor, the at least one motor, and a power source for providing power to the processor and the at least one motor.

6. The method of claim 1, wherein the catheter autonomously delivers the prosthetic replacement heart valve to the native heart valve.

7. The method of claim 1, further comprising:
    providing an input with a control device to the processor to cause the processor to actuate at least a portion of the catheter; and
    adjusting the input utilizing the processor to avoid or retract from the inner wall of the blood vessel based on the signals from the one or more proximity sensors of the lateral distance between the nose cone and the inner wall of the blood vessel.

8. The method of claim 1, wherein the processor controls the at least one motor to deflect the distal end portion of the elongate shaft of the catheter with the one or more pull wires utilizing a machine learning algorithm utilizing data from past implantation procedures or from characteristics of the patient.

9. The method of claim 1, wherein the native heart valve is the mitral heart valve, and advancing the elongate shaft of the catheter through the patient's vasculature includes passing the elongate shaft of the catheter through an atrial septum of the patient's heart.

10. The method of claim 1, wherein the native heart valve is the aortic heart valve, and advancing the elongate shaft of the catheter through the patient's vasculature includes passing the elongate shaft of the catheter through an aortic arch of the patient's heart, and
    wherein the processor controls the at least one motor to deflect the distal end portion of the elongate shaft of the catheter with the one or more pull wires within the aortic arch based on the signals from the one or more proximity sensors of the lateral distance between the nose cone and an inner wall of the aortic arch.

11. The method of claim 1, wherein the one or more proximity sensors sense the lateral distance between the nose cone and the inner wall of the blood vessel utilizing ultrasound signals.

12. The method of claim 1, wherein the one or more proximity sensors sense the lateral distance between the nose cone and the inner wall of the blood vessel utilizing echo signals.

13. The method of claim 1, wherein the one or more proximity sensors sense the lateral distance between the nose cone and the inner wall of the blood vessel utilizing visual identification.

14. The method of claim 1, wherein one or more imaging devices are located on the elongate shaft for imaging the patient's vasculature within the patient's vasculature.

15. The method of claim 1, further comprising utilizing the one or more proximity sensors on the nose cone to sense a distance between the distal end portion of the elongate shaft and the native heart valve.

16. The method of claim 1, further comprising utilizing the one or more proximity sensors on the nose cone to sense a distance between the distal end portion of the elongate shaft and the native heart valve while deploying the prosthetic replacement heart valve to the native heart valve from the distal end portion of the elongate shaft of the catheter.

17. The method of claim 1, further comprising utilizing the one or more proximity sensors on the nose cone to sense a distance between the distal end portion of the elongate shaft and the native heart valve to align the distal end portion of the elongate shaft with an annulus of the native heart valve.

18. The method of claim 1, further comprising gripping a handle coupled to a proximal end portion of the elongate shaft and manually advancing the elongate shaft of the catheter through the blood vessel.

19. The method of claim 18, further comprising manually manipulating one or more control devices on the handle to deflect the distal end portion of the elongate shaft.

20. The method of claim 18, wherein a power source is positioned within the handle.

21. The method of claim 1, wherein the one or more proximity sensors are a first one or more proximity sensors, and a second one or more proximity sensors are positioned on a retractable capsule of the elongate shaft surrounding the prosthetic replacement heart valve, the second one or more proximity sensors for sensing a distance between the distal end portion of the elongate shaft and the inner wall of the patient's vasculature.

22. The method of claim 1, wherein the prosthetic replacement heart valve comprises an expandable frame and a tissue-based valve body supported by the expandable frame, wherein the tissue-based valve body provides one-way blood flow for replacing a function of the native heart valve.

* * * * *